US008868155B2

(12) United States Patent
 Debuc

(10) Patent No.: US 8,868,155 B2
(45) Date of Patent: Oct. 21, 2014

(54) SYSTEM AND METHOD FOR EARLY DETECTION OF DIABETIC RETINOPATHY USING OPTICAL COHERENCE TOMOGRAPHY

(75) Inventor: Delia Debuc, Pembroke Pines, FL (US)

(73) Assignee: University of Miami, Miami, FL (US)

( * ) Notice: Subject to any disclaimer, the term of this patent is extended or adjusted under 35 U.S.C. 154(b) by 290 days.

(21) Appl. No.: 13/130,387

(22) PCT Filed: Dec. 18, 2009

(86) PCT No.: PCT/US2009/068653
 § 371 (c)(1),
 (2), (4) Date: Jul. 25, 2011

(87) PCT Pub. No.: WO2010/080576
 PCT Pub. Date: Jul. 15, 2010

(65) Prior Publication Data
 US 2011/0275931 A1 Nov. 10, 2011

Related U.S. Application Data

(60) Provisional application No. 61/139,082, filed on Dec. 19, 2008.

(51) Int. Cl.
 *A61B 3/00* (2006.01)
 *G01B 9/02* (2006.01)
 *A61B 3/12* (2006.01)
 *A61B 3/10* (2006.01)
 *G06T 7/00* (2006.01)

(52) U.S. Cl.
 CPC ........... *A61B 3/1225* (2013.01); *G06T 2200/24* (2013.01); *G06T 2207/10101* (2013.01); *A61B 3/102* (2013.01); *G06T 2207/30041* (2013.01); *G06T 2207/20036* (2013.01); *G06T 7/0014* (2013.01)
 USPC ........... 600/425; 600/427; 600/407; 356/479; 356/497; 351/206

(58) Field of Classification Search
 None
 See application file for complete search history.

(56) References Cited

U.S. PATENT DOCUMENTS

| 7,982,071 | B2 | 7/2011 | Scott et al. |
| 8,081,808 | B2 * | 12/2011 | Huang et al. .................. 382/128 |
| 2003/0103212 | A1 | 6/2003 | Westphal et al. |
| 2003/0165486 | A1 | 9/2003 | Karageozian |
| 2004/0127843 | A1 | 7/2004 | Tu et al. |
| 2007/0216909 | A1 | 9/2007 | Everett et al. |

OTHER PUBLICATIONS

International Search Report issued in International Application No. PCT/US/2009/068653 dated Mar. 9, 2010 (2 pages).

(Continued)

*Primary Examiner* — Long V. Le
*Assistant Examiner* — Farshad Negarestan
(74) *Attorney, Agent, or Firm* — Novak Druce Connolly Bove + Quigg LLP

(57) ABSTRACT

A system for the imaging, processing and evaluation of tissues provides prognostic and diagnostic details regarding diseased tissue. A set of quantitative measures were developed and integrated in an image-base analysis software tool designed for OCT images. The system and methods in this invention is significant because it allows assessing the optical properties and structure morphology differences between normal healthy subjects and diabetic patients with retinopathy up to ETDRS level 35 and without retinopathy.

5 Claims, 14 Drawing Sheets

(56) References Cited

OTHER PUBLICATIONS

Ranganathan, "A Computer-aided System for Interactive Image Analysis of Retinal Pathologies Using Optical Coherence Tomography," Thesis, University of Miami, Mar. 17, 2008, p. 4-7; p. 15, para 1; p. 21, para 1; p. 44, para 1; p. 46, para 3; p. 46, para 3; p. 57, para 3; p. 64-69; p. 72-77; p. 97-98; p. 101, para 1; Fig. 4.15, 4.16(A)-4.16(B) (130 pages).

Bartko et al., "On the methods and theory of reliability", J Nerv Ment Dis (1976) 163(5): 307-317. (abstract only).

Bland et al., "Statistical methods for assessing agreement between two methods of clinical measurement", Lancet (1986) 1: 307-310.

British Standards Institution, "Accuracy (trueness and precision) of measurement methods and results—Part 2: Basic method for the determination of repeatability and reproducibility of a standard measurement method", BS ISO 5725 Part 2 (1994). London.

Cabrera et al., "Automated detection of retinal layer structures on optical coherence tomography images", Opt Express (2005) 13: 10200-10216.

Cheung et al., "Diabetic retinopathy and systemic vascular complications", Progress in Retinal and Eye Research (2008) 27: 161-176.

Frohman et al., "Optical coherence tomography: A window into the mechanisms of multiple sclerosis", Neurology (2008) 4(12): 664-675.

Longmuir et al., "Optical coherence tomography (OCT) in neuro-opthamology: A clinical perspective", Neuro-Opthamology (2008) 32: 115-125.

Polito et al., "Effect of posture on the dirunal variation in clinically significant diabetic macular edema", Arch Opthalmol (2005) 123: 1330-1337.

Salinas et al., "Comparison of PDE-based nonlinear diffusion approaches for image enhancement and denoising in optical coherence tomography", IEEE Transactions on Medical Imaging (2007) 26(6): 761-771.

Wolf-Schnurrbush et al., "Ethnic differences in macular pigment density and distribution", Invest Opthalmol Vis Sci (2007) 48(8): 3783-3787.

* cited by examiner

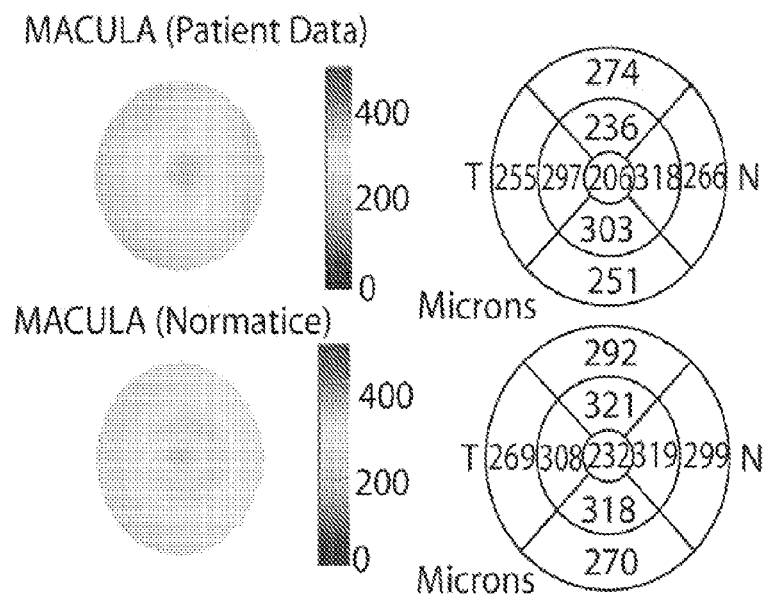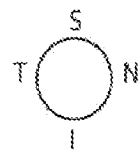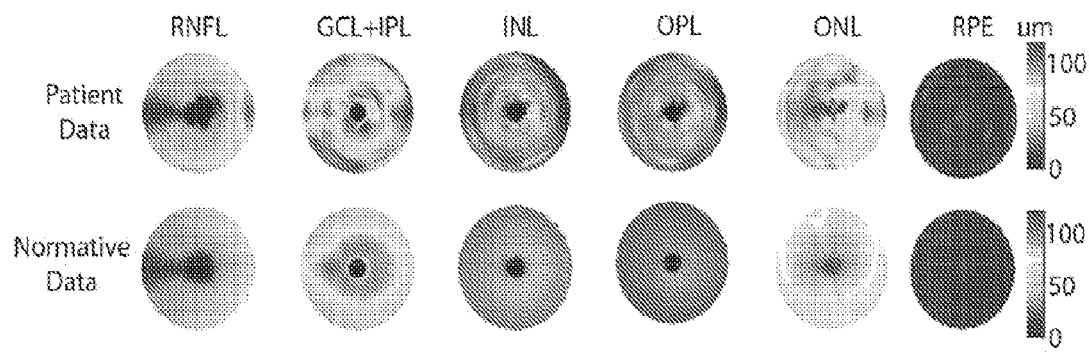
Fig. 5B

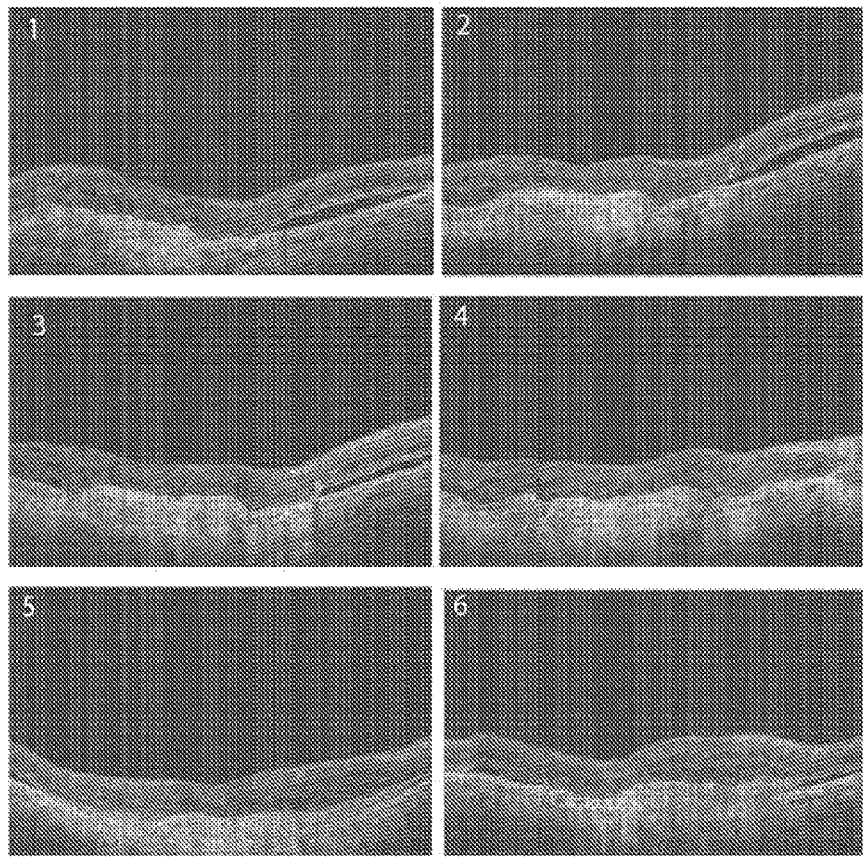
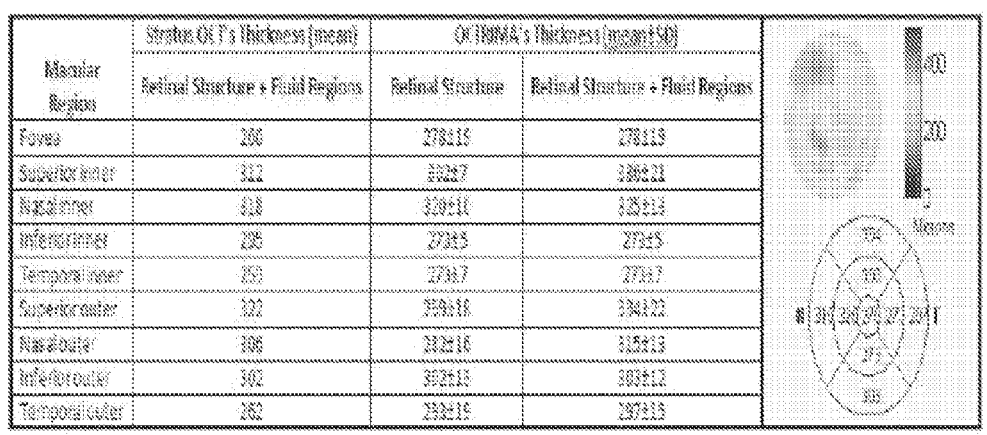
FIG.6A

SYSTEM AND METHOD FOR EARLY DETECTION OF DIABETIC RETINOPATHY USING OPTICAL COHERENCE TOMOGRAPHY

CROSS-REFERENCE TO RELATED APPLICATIONS

This application is a §371 national phase entry of International Application No. PCT/US2009/068653, filed Dec. 18, 2009, which claims priority to U.S. Provisional Patent Application No. 61/139,082, filed Dec. 19, 2008, the entire contents of which are incorporated herein by reference.

FIELD OF THE INVENTION

Embodiments of the invention relate to the field of ophthalmology. More particularly, the present invention relates to a system for detecting images and methods for assessing early signs of diabetic retinopathy in an image.

BACKGROUND

Diabetes mellitus is a leading cause of vision loss in industrialized and developed countries. Diabetic retinopathy (DR) is a common complication of type 1 diabetes, affecting up to 60% of individuals with type 1 diabetes with a duration of ≥15 years at any point in time. The Diabetes Control and Complications Trial (DCCT) demonstrated that 10% of patients with good metabolic control (glycated hemoglobin ≤6.87%) developed retinopathy, whereas 43% of patients with poor metabolic control (glycated hemoglobin ≥9.49%) did not develop retinopathy. These data suggest that although poor glycemic control is an important predictor of retinopathy, there are many individuals who develop retinopathy despite good glycemic control. Identifying additional predictors of retinopathy is therefore important in screening for the development of this complication.

In diseases in which diagnosis is based mainly on an image, as in DR, not only the contribution of new imaging technologies is essential, but also the development of quantitative computed-assisted tools to aid in the diagnoses is fundamental for the establishment of methods in clinical practice to assist physicians and for improving the quality of medical care. Even though, detailed and well-documented diagnostic protocols have been developed over the last 20 years, there are still constrains in the underlying data generation mechanisms found in actual diabetic screening. Image quality has also been identified as a limited factor.

SUMMARY

This Summary is provided to briefly indicate the nature and substance of the invention. It is submitted with the understanding that it will not be used to interpret or limit the scope or meaning of the claims.

The aspects and embodiments of the invention disclosed herein relate to a computer-aided diagnostic system and methods for the early detection and diagnosis of DR and other ocular diseases or disorders.

In preferred embodiments, the optical properties and structure morphology differences between normal healthy subjects and diabetic patients with retinopathy up to ETDRS level 35 and without retinopathy are assessed.

In another preferred embodiment, a method of quantifying the various cellular layers of the retina in a subject comprises a computer implemented system. The system comprises an input for receiving source data from an OCT device, and a processing unit configured to perform a methodology according to embodiments of the present invention.

In another preferred embodiment, a method of screening a population for diabetic retinopathy comprises analyzing early local abnormalities in the structure of the intraretinal layers of individuals in the population using the system and methods according to embodiments of the present invention. In one aspect, the present invention also provides a computer readable medium encoding instructions for performing an image analysis method according to embodiments of the present invention.

Other aspects are described infra.

BRIEF DESCRIPTION OF THE DRAWINGS

FIG. 2A Automatic mode showing original raw image (B-scan) with overlaid retinal boundaries labeled. FIG. 2B Manual mode displaying the manual toolbar when the "Start Manual Corrections Tool" button is clicked.

FIG. 3A: visible segmentation errors such as small peaks, linear offsets, curve offsets and false segmentations. Manual error removal results for: FIG. 3B shows the false segmentation. Note the falsely detected outer boundaries of the RNFL which is often barely visible on the temporal side of the macula, like in this case; FIG. 3C: Small peaks. Note the tiny overshoots or undershoots visible along the boundaries outlined in yellow and cyan, resulting in inaccurate segmentation; FIG. 3D: Foveal center control. A predefined control is also in place for the inner retinal layers in a 1.5 mm diameter zone in the fovea (see results after manual correction), where retinal reflections are minimally visible. The control forces the ILM, the inner and outer side of the GCL+IPL complex, and the outer side of the INL and OPL to be coincident in this region; FIG. 3E: Linear offsets. These are parts of a boundary that form a straight line segment but are incorrectly detected as a peak or an elevated or depressed line segment by the automated algorithm (e.g. see the errors in the outer boundary of the OPL (outlined in green); FIG. 3F: Curved offsets. Curve offset is a term given to the curved portion of a boundary that has not been recognized as a curve, instead, has been incorrectly segmented as an elevated or depressed curve (e.g. see the manual corrections for the inner and outer boundaries of the INL (outlined in yellow and cyan, respectively). The border outlined in blue corresponds to the outer boundary of the choriocapillaries (ChCap) segment that can be extracted manually using the semi-automated approach in OCTRIMA.

FIG. 5B shows the OCTRIMA thickness maps for the patient data shown in FIG. 5A. The middle panel shows the total retinal thickness map. The lower panel shows the thickness map for the intraretinal layers. An OCTRIMA macular map is divided into nine zones that correspond to the ETDRS regions: fovea within a diameter of 1 mm centered on the foveola; pericentral ring, the circular band from the central 1 mm to 3 mm, divided into four quadrants i.e. superior, inferior, temporal, and nasal; and peripheral ring from 3 mm up to 6 mm, divided into the same quadrants.

FIG. 6A shows the OCTRIMA segmentation results for a patient with neovascular AMD (non aligned raw data) showing the fluid-filled regions outlined. The ONL outer border was used as the outer retinal border in order to compare results with Stratus OCT algorithms (see Table at the bottom). The retinal thickness map along with the ETDRS topographic map including the retinal structure and fluid-filled regions are shown at the right-bottom section.

FIG. 7A: Main program window of the GUI in its first stage of development. FIG. 7B: Scattering coefficient and co-occurrence based classifier results for a consecutive image in the data set after registration.

DETAILED DESCRIPTION

Figure 1:
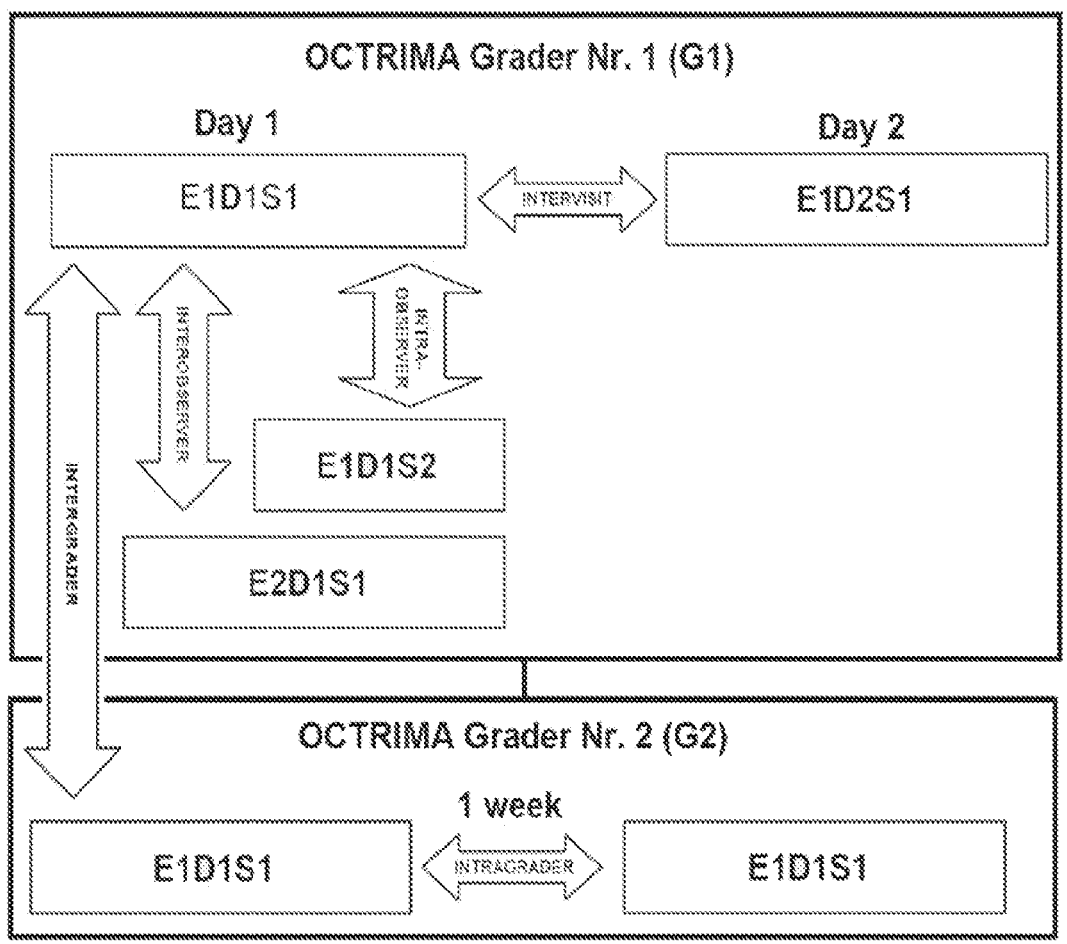
FIG. 1 is a schematic representation showing the study which was setup for the reproducibility of OCTRIMA measurements. A total of 10 healthy eyes were scanned during 4 sessions (E1D1S1, E1D1S2, E2D1S1 and E1D2S1) in 2 consecutive days (D1, D2) by two OCT examiners (E1, E2) and analyzed by two independent experienced graders (G1, G2). The first grader (G1) segmented all the B-scans from all sessions (E1D1S1, E1D1S2, E2D1S1 and E1D2S1) using OCTRIMA. All the B-scans from the first session (E1D1S1) were also segmented by the second grader (G2) and results were used in the intergrader reproducibility analysis. The OCT B-scans from the first session (E1D1S1) were graded twice by one grader (G2) one week after the initial assessment to assess intragrader reproducibility of OCTRIMA.

An objective quantitative tool for the early diagnosis and evaluation of treatment in diabetic retinopathy (DR) and other ocular disorders is provided. Optical Coherence Tomography (OCT) performs high resolution imaging of retinal structure non-invasively and in real time. OCT images can either be used to qualitatively assess retinal features and pathologies or to objectively make quantitative measurements. OCT can facilitate decisions on the treatment protocol (surgical or medical) and follow-up of diabetic patients, which is especially important in the early stages of diabetic maculopathy when the structural changes are not yet evident with slit-lamp biomicroscopy or angiographically.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Throughout this application, the term "about" is used to indicate that a value includes the standard deviation of error for the device or method being employed to determine the value.

The word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is if, X employs A; X employs B; or X employs both A and B, then "X employs A or B" is satisfied under any of the foregoing instances.

Optical Coherence Tomography

Computer based analysis of medical images pertaining to ascertaining retinal structure allows for the diagnosis of retinal diseases and function. Identifying and measuring the various cellular layers of the retina allows a medical expert to access disease states and prescribe therapeutic regimens. In embodiments of the invention, a set of quantitative measures were developed that have been integrated in an image-base analysis software tool specifically designed for OCT images. The system and methods in this invention is significant because it allows for the assessing of optical properties and structure morphology differences between normal healthy subjects and diabetic patients with retinopathy up to ETDRS level 35 and without retinopathy. At the same time, the quantitative measures facilitate the management of progressive changes before and after treatment of DR once a good evidence base for treatment is detected. Moreover, it is also possible to determine which cellular layer(s) of the retinal structure is (are) involved in DR and whether is there any rule concerning which layer(s) get damaged first.

Embodiments of the invention offer many advantages. One of the advantages is that local abnormalities in the structure of the various cellular layers of the retina can be detected using OCT images. This advantage arises from the quantitative measures and methods disclosed herein. Specifically, the computer-aided diagnostic system and methods disclosed herein enable the measurement of total retinal thickness along with the local thickness and optical properties of the intraretinal layers, which could provide a potential improvement in the clinical application of the OCT technology to early detect and diagnose DR. The computer-aided diagnostic system and methods described herein can be used to analyze OCT data from different OCT systems and device configurations. Exemplary OCT systems include, but are not limited to: time domain and spectral domain OCT. In addition, the preceding step of manifest DR may be a neurodegeneration of the retina which seems to be detectable by OCT mapping of the local retinal abnormalities. This aspect of diabetic retinal changes is not yet a part of the common thinking about diabetes, but future studies using the system and methods described herein, elaborating histological and functional changes of the macula in diabetic patients would shed light on this very first step possibly leading to the further sequelae of DR.

Figure 9:
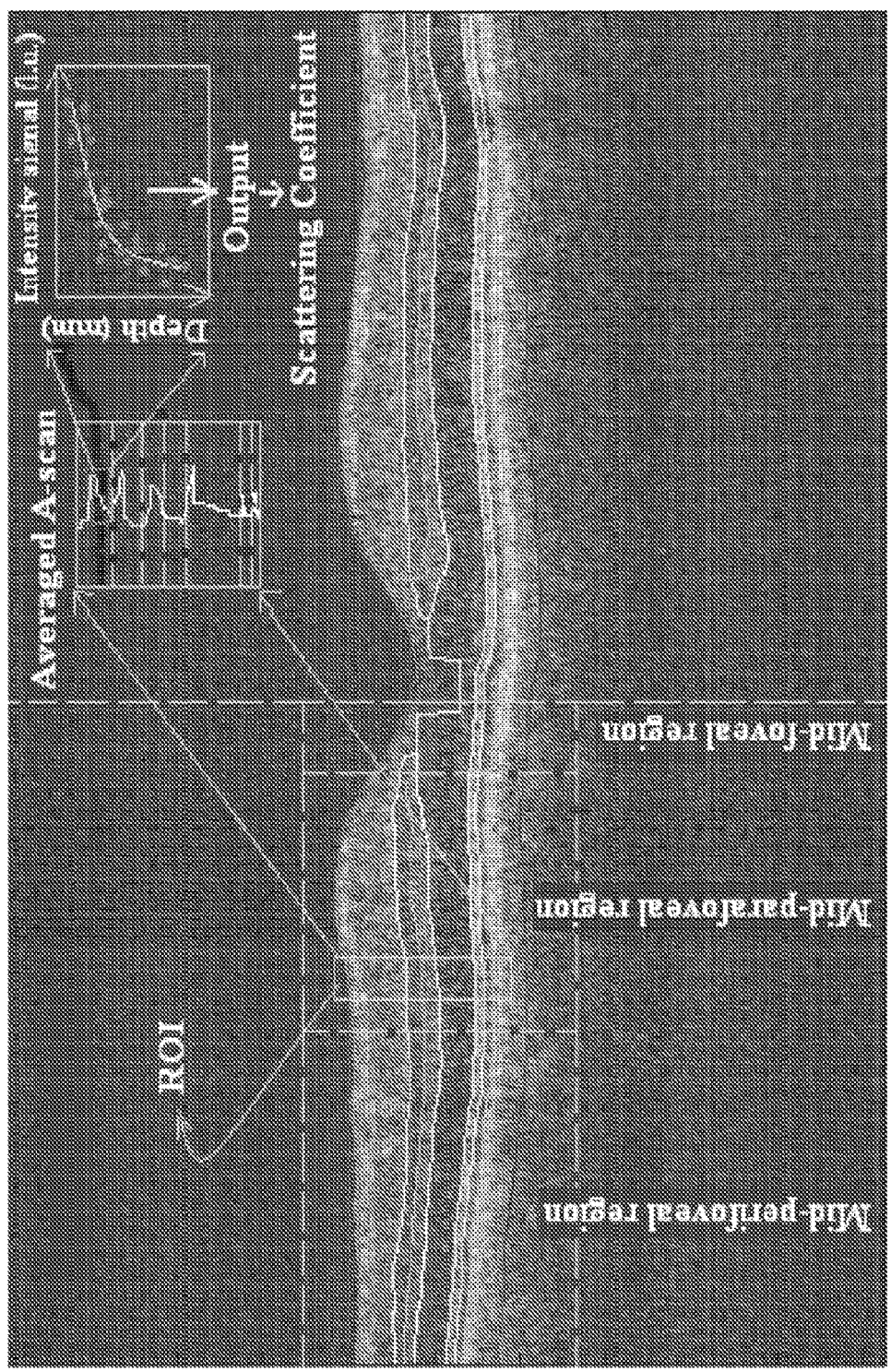
FIG. 9 is a schematic representation of the principles of the extraction algorithm. Note that three macular regions are defined: mid-foveal, mid-perifoveal and mid-parafoveal (see orange dashed insets). A transverse ROI (light blue dashed inset) is selected and an averaged A-scan is obtained. Then the curve-fitting is performed on this resulting averaged A-scan for every segmented layer. Note that in this demonstrative example, the curve-fitting process has been only shown for one of the segmented layers.

In a preferred embodiment, the present invention provides a method for measuring thickness, extracting optical properties and classifying the tissue of the various cellular layers of the retina of a subject in order to identify local abnormalities in the retinal structure. The extraction of optical properties comprises the local measurement of tissue reflectivity along with the estimation of tissue scattering coefficients from OCT images through mathematical processing (see, for example, FIG. 9). Tissue classification comprises the classification of retinal tissue into one of two possibilities (normal/abnormal) through texture analysis algorithms.

In general, methods according the embodiments of the present invention comprise the steps of comparing the thickness, optical properties and tissue classification of the various cellular layers of the retina of a subject with normal reference data to identify local abnormalities in the retinal structure, wherein the normal reference data is compiled from thickness and optical properties of the various cellular layers of the retina of a population with normal eyes, and wherein data extracted from the subject is abnormal if it meets predetermined comparison criteria.

The normal reference data may be preferably generated from optical coherence tomograms. Reference thickness and reflectance data may be obtained by averaging retinal thickness and reflectance data of the intraretinal layers of a population of healthy individuals with normal eyes. An exemplary reference retinal thickness data that is also known as a thickness map may contain average thickness values of each coordinate on the map and the corresponding standard deviations.

In a preferred embodiment, a reference data or map of the present invention generally may be compiled as follows:

Subjects are assigned to normal group if both eyes had intraocular pressure (TOP) of less than 21 mm Hg, a normal visual field (VF) (defined as having a mean deviation and pattern standard deviation within 95% limits of the normal reference and a glaucoma hemifield test within 97% limits), a normal foveal thickness (mean thickness in the central 1000-μm diameter area) and normal central foveal thickness (mean thickness at the point of intersection of 6 radial scans), a normal-appearing optic nerve head, and a normal nerve fiber layer and normal retina in macular region and if the participant did not have a history of chronic ocular or systemic corticosteroid use.

The step of comparing the retinal thickness map of each intraretinal layer of a subject to a reference map comprises making a comparison of the thickness value at each corresponding region or coordinate of the maps. If the value of the subject's retinal thickness map exceeds the value of the reference map at the corresponding map coordinate by a preset multiple of standard deviation (SD), an abnormal thickness is indicated and it is included in the "abnormal classification". Selection of this preset "cut-off" threshold depends on the desired confidence level. Preferably, the preset threshold is about 2.33 standard deviations and above (99 percentile). Other useful threshold values include 1.65 standard deviations (95 percentile) or any other values between 1.65 and 2.33 standard deviations. The same methodology is followed to compare the optical properties and tissue classification measures.

In some embodiments, a method of the present invention further comprises a step of identifying an abnormal pattern by finding one or more regions on the subject's intraretinal thickness map whose value is greater or smaller than a predetermined multiple of standard deviations above the mean value at the same location of the normal reference map. The cut-off threshold for identifying the abnormal pattern is preferably 2.60 standard deviations and above (99.5 percentile). Other suitable pattern thresholds include 3.09 standard deviations (99.9 percentile) to 2.33 standard deviations (99 percentile). To identify an abnormal pattern, a method of the present invention may further comprise searching and identifying an abnormal thickness for a specific intraretinal layer by assessing the regional thickness of the particular layer and classifying it as abnormal if it has a thickness greater or smaller than a predetermined thickness. The threshold level for the abnormal region should be lower or higher than that for the reference. 2SDs were used to define cutoffs for the upper and lower levels of normative values. Normal values were applicable for both control subjects and diabetic patients without evidence of DR. Borderline values were suitable for diabetic patients with early signs of retinopathy. Based on the identified abnormal pattern, methods of the present invention may further make diagnosis of early diabetic retinopathy if the abnormal layer fits a predetermined set of criteria:

Criterion 1: Borderline thickness values
Criterion 2: Borderline reflectance values
Criterion 3: Borderline scattering coefficients
Criterion 4: Borderline texture measures A good predictor of early diabetic retinopathy (PEDR) is implemented by constructing a weighted function resulting from the combination of the above criteria with the use of weight coefficients:

$$PEDR(M_D, M_C) = \min \sum_{i=1}^{N} w_i \times d(M_{Di}, M_{Ci}) \quad (1)$$

Where $w_i$ are the weight coefficients ($w_i \geq 0$, $i=1 \ldots N$), d is the distance function and $M_{Di}$, $M_{Ci}$ are the measured values (i.e. thickness, reflectance, scattering coefficient, texture measures) for diabetic patients and subjects in the control group, respectively. N is the number of objective functions or criteria considered in the analysis (N=4). PEDR is a natural distance measure for similarity search where $w_i$ is the extent to which measure $M_{Di}$ is matched to $M_{Ci}$.

The weighted function is then used to differentiate diabetic eyes with early signs of retinopathy from both normal eyes and diabetic patients without retinopathy. The PEDR provides a simple and accurate index for early detection and diagnosis of DR. Therefore, OCT would be a valuable additional tool not only in the follow-up of diabetic retinopathy but also in screening programs for DR.

Other suitable criteria are also embodied in embodiments of the invention. For example, three quantitative measures (QM) may be used to identify pathological changes in the retinal structures from a local point of view. Since OCT measures the intensity of light returning from within a sample, then samples having a higher heterogeneity of optical index of refraction have a larger variance. Thus, diseased retina might have multiple strong back reflections resulting in a relatively high OCT signal variance. Then, the normalized standard deviation within a region of interest (ROI) could be defined as the first QM:

$$QM1 = \frac{\sqrt{\frac{1}{N-1} \times \sum_{ROI_{high}} \sum_{ROI_{width}} (I(x,y) - \bar{I})^2}}{(I_{max} - I_{min})} \quad (2)$$

Note that in order to correct the data for variations in the OCT system settings, the standard deviation should be normalized by the maximum and minimum OCT signal present in the OCT image. The number of pixels in the ROI is denoted by N. Moreover, I(x,y) is the OCT signal as a function of x and y locations within the ROI; and $\bar{I}$ is the average OCT signal within the ROI.

Assuming a ROI corresponding to an (n-m) segment in depth and an (r-l) segment in lateral displacement, an integrated backscattered index can be defined as the second QM:

$$QM2 = \frac{1}{(x_r - x_l)(y_n - y_m)} \sum_{j=r}^{l} \sum_{i=n}^{m} |I(x_j, x_i)| \quad (3)$$

In order to identify local abnormalities in the diabetic retinal structure, these quantitative measures may be obtained per ROI for every diabetic patient and compared with the QM norm values obtained for subjects in the control group. The criteria can also be adjusted according to future studies on the treatment of diabetic retinopathy or other forms of retinopathy.

Assuming that peak reflectance intensity of the OCT signal changes significantly in layers or ROIs with early retinopathy signs, an early diabetic retinopathy (EDR) index can be defined as the third QM:

$$QM3 = \frac{NMR}{NRS} \quad (4)$$

Where NMR is the normalized mean reflectance and NRS is the normalized reflectance of saturation (i.e. the lowest reflectance of the upper 50 pixels on each A-scan line). The normalization procedure compensates for variation in absolute reflectance intensity between images, caused by eye and head movement, tear film quality, pupil size, and laser detector alignment. The QM3 norm per layer and specific predefined ROIs obtained from subjects in the control group is used to calculate the borderline value that determines the EDR index (QM3).

In another preferred embodiment, a computer-aided system designed to extract almost cellular-like pathophysiological information from the retinal tissue in vivo is provided. In general, this system comprises a software tool for OCT retinal image analysis (OCTRIMA) which is an interactive, user-friendly stand-alone application for analyzing OCT retinal images. The application essentially provides dual functionality in a single software package by combining image enhancement and speckle denoising of OCT images along with intraretinal segmentation and error correction using direct visual evaluation of the detected boundaries. OCTRIMA is also able to minimize segmentation errors, give quantitative information of intraretinal structures and also facilitates the analysis of other retinal features that may be of diagnostic and prognostic value, such as morphology and reflectivity. A final report is generated and the complete data resulting from the analysis are also available for further analysis. The processing unit may be a general purpose computing unit such as a PC, a workstation, or any other suitable processing unit known in the art. Various software tools may be used to configure the processing unit. For example, the processing unit may be equipped with customized machine codes to perform methods of the present invention to achieve maximum speed. Other software tools that may be used include, but not limited to pre-packed software tools such as MatLab, or application software developed in programming languages such as C, C++, JAVA, or any other programming language commonly known in the art.

The OCTRIMA tool is configured to perform an analysis method having the general steps of (i) receiving the tomogram; (ii) image enhancement and speckle denoising; (iii)

automatic and semi-automatic segmentation of the intraretinal layers; (iv) computing total retinal and intraretinal thickness maps from the tomogram; (v) computing the intensity at each point of a specific A-scan relative to the value of the highest intensity value along the length of the entire A-scan from the vitreous to the choroids and (vi) identifying which intraretinal layers are abnormal by comparing the thickness map, reflectance data, scattering coefficients and texture measures with the mean and standard deviation of the thickness, reflectance, scattering coefficients and texture measures in similar layers in a population of eyes considered as the control group.

Figure 10:
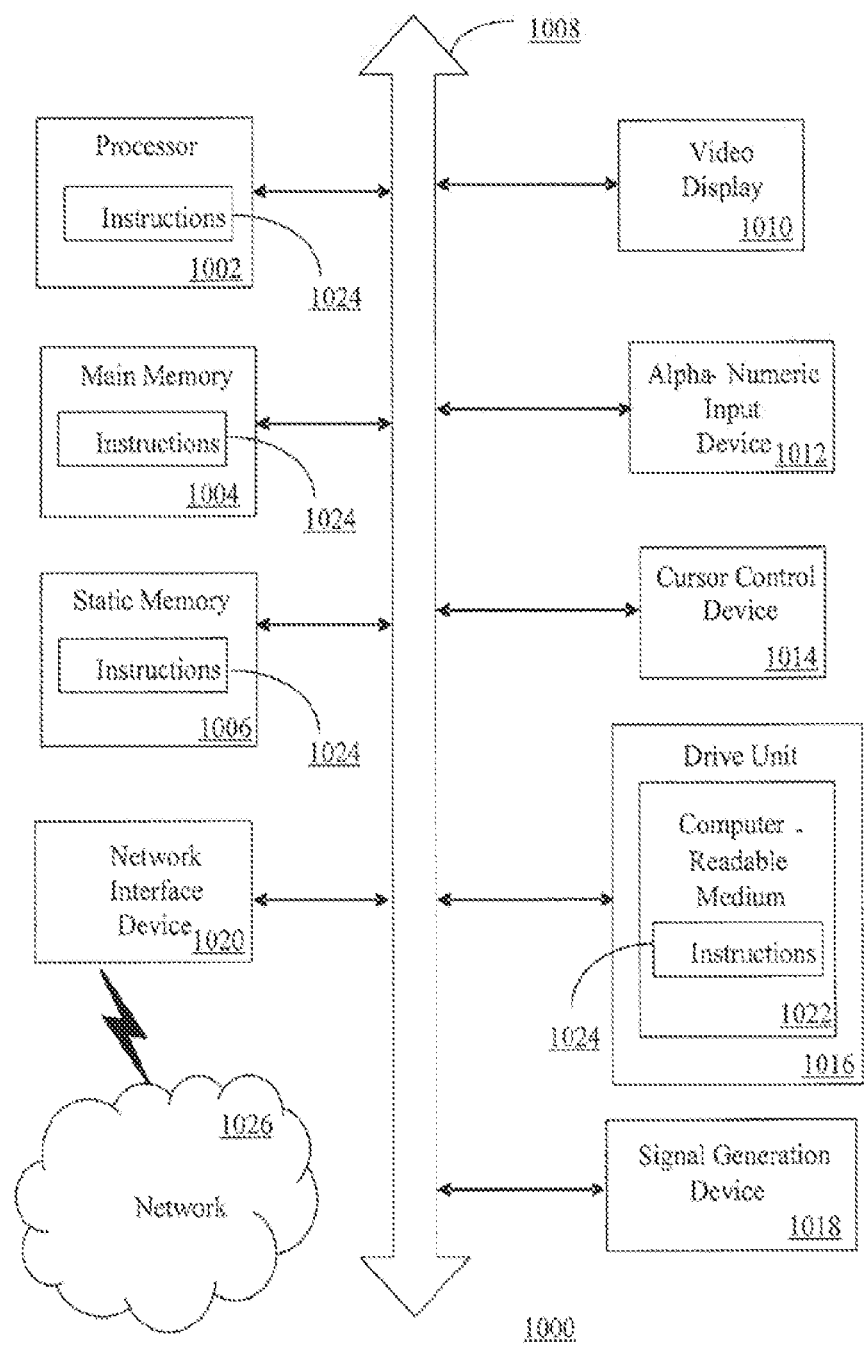
FIG. 10 is a schematic diagram of a computer system 1000 for executing a set of instructions that, when executed, can cause the computer system to perform one or more of the methodologies and procedures described above. For example, a computer system 1000 can be implemented to perform the various tasks of the systems 400, 500, 600, 700, 800. In some embodiments, the computer system 1000 operates as a single standalone device. In other embodiments, the computer system 1000 can be connected (e.g., using a network) to other computing devices to perform various tasks in a distributed fashion. In a networked deployment, the computer system 1000 can operate in the capacity of a server or a client developer machine in server-client developer network environment, or as a peer machine in a peer-to-peer (or distributed) network environment.
Figure 11:
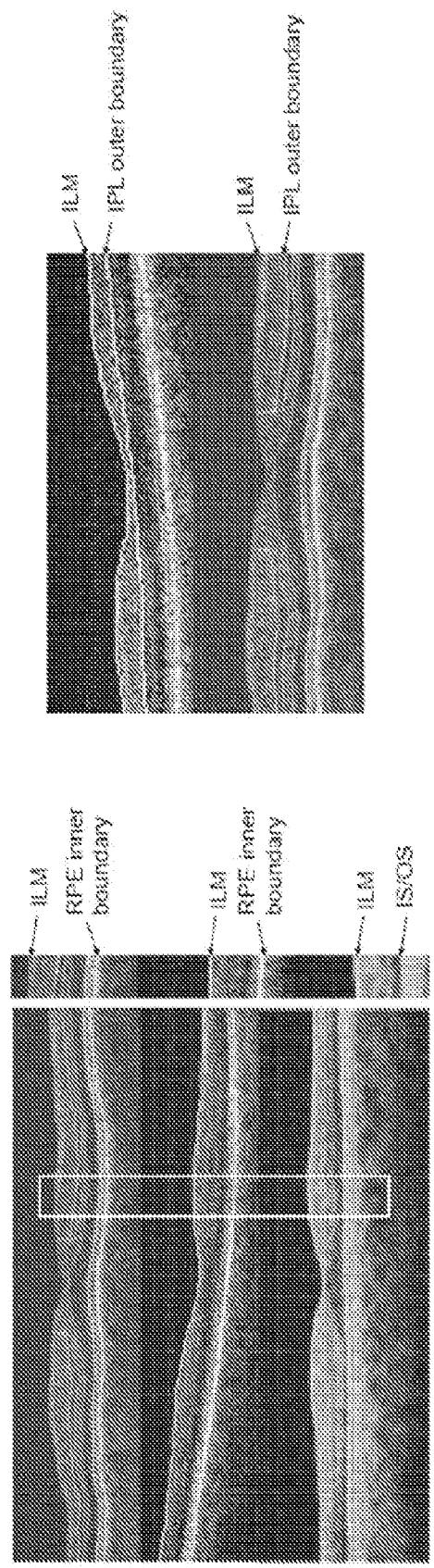
FIG. 11 shows the comparison of the inner and outer boundary detection between OCTRIMA, RTVue and Stratus (left, from top to bottom) and the GCC boundary detection between RTVue and OCTRIMA (right).
Figure 12:
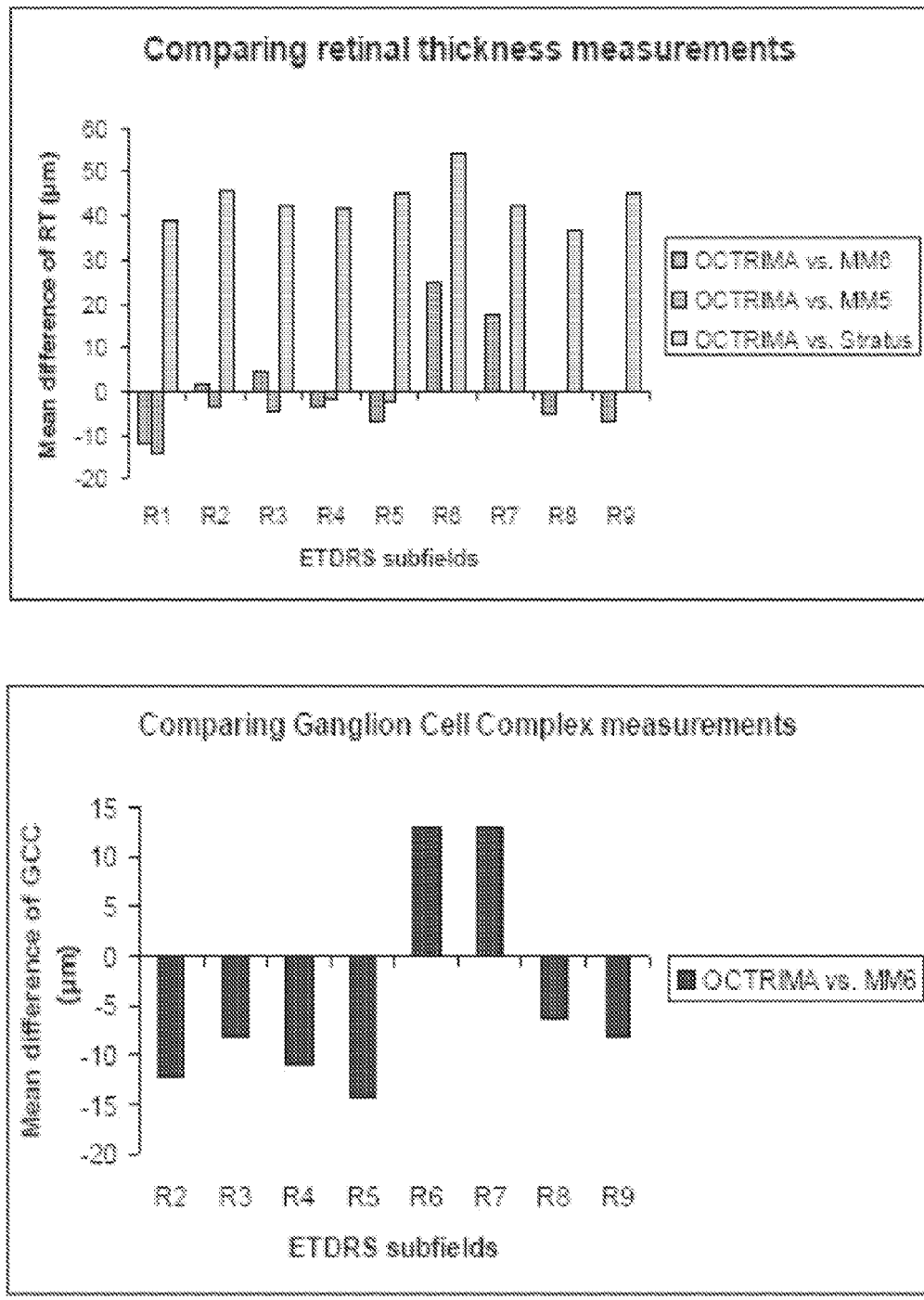
FIG. 12 are graphs showing the comparison of RT (left) and GCC measurements (right) between OCTRIMA and the softwares of the OCT devices.

A person skilled in the relevant art will readily recognize that the various aspects of computerization and automation represent different exemplary implementations and utilizations of methods according to the present invention. In a clinical setting, automation and computerization of diagnosis methods and data analysis methods have many advantages. Automation of a diagnosis or analysis method minimizes human involvement, thereby, reduces the chance of human error. In a clinical setting, computerization also enhances data acquisition precision and quality from patient to patient, thereby, allowing a clinic to deliver a more uniform and higher standard of service. For example, FIG. 10 shows a schematic diagram of a computer system 1000 for executing a set of instructions that, when executed, can cause the computer system to perform one or more of the methodologies and procedures described above.

In this illustration, a computer system 1000 can be implemented to perform the various tasks of the systems 400, 500, 600, 700, 800. In some embodiments, the computer system 1000 operates as a single standalone device. In other embodiments, the computer system 1000 can be connected (e.g., using a network) to other computing devices to perform various tasks in a distributed fashion. In a networked deployment, the computer system 1000 can operate in the capacity of a server or a client developer machine in server-client developer network environment, or as a peer machine in a peer-to-peer (or distributed) network environment.

The computer system 1000 can comprise various types of computing systems and devices, including a server computer, a client user computer, a personal computer (PC), a tablet PC, a laptop computer, a desktop computer, a control system, a network router, switch or bridge, or any other device capable of executing a set of instructions (sequential or otherwise) that specifies actions to be taken by that device. It is to be understood that a device of the present disclosure also includes any electronic device that provides voice, video or data communication. Further, while a single computer is illustrated, the phrase "computer system" shall be understood to include any collection of computing devices that individually or jointly execute a set (or multiple sets) of instructions to perform any one or more of the methodologies discussed herein.

The computer system 1000 can include a processor 1002 (such as a central processing unit (CPU), a graphics processing unit (GPU, or both), a main memory 1004 and a static memory 1006, which communicate with each other via a bus 1008. The computer system 1000 can further include a display unit 1010, such as a video display (e.g., a liquid crystal display or LCD), a flat panel, a solid state display, or a cathode ray tube (CRT)). The computer system 1000 can include an input device 1012 (e.g., a keyboard), a cursor control device 1014 (e.g., a mouse), a disk drive unit 1016, a signal generation device 1018 (e.g., a speaker or remote control) and a network interface device 1020.

The disk drive unit 1016 can include a computer-readable storage medium 1022 on which is stored one or more sets of instructions 1024 (e.g., software code) configured to implement one or more of the methodologies, procedures, or functions described herein. The instructions 1024 can also reside, completely or at least partially, within the main memory 1004, the static memory 1006, and/or within the processor 1002 during execution thereof by the computer system 1000. The main memory 1004 and the processor 1002 also can constitute machine-readable media.

Dedicated hardware implementations including, but not limited to, application-specific integrated circuits, programmable logic arrays, and other hardware devices can likewise be constructed to implement the methods described herein. Applications that can include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the exemplary system is applicable to software, firmware, and hardware implementations.

In accordance with various embodiments of the present disclosure, the methods described herein can be stored as software programs in a computer-readable storage medium and can be configured for running on a computer processor. Furthermore, software implementations can include, but are not limited to, distributed processing, component/object distributed processing, parallel processing, virtual machine processing, which can also be constructed to implement the methods described herein.

The present disclosure contemplates a computer-readable storage medium containing instructions 1024 or that receives and executes instructions 1024 from a propagated signal so that a device connected to a network environment 1026 can send or receive voice and/or video data, and that can communicate over the network 1026 using the instructions 1024. The instructions 1024 can further be transmitted or received over a network 1026 via the network interface device 1020.

While the computer-readable storage medium 1022 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable medium" shall accordingly be taken to include, but not be limited to, solid-state memories such as a memory card or other package that houses one or more read-only (non-volatile) memories, random access memories, or other re-writable (volatile) memories; magneto-optical or optical medium such as a disk or tape; as well as carrier wave signals such as a signal embodying computer instructions in a transmission medium; and/or a digital file attachment to e-mail or other self-contained information archive or set of archives considered to be a distribution medium equivalent to a tangible storage medium. Accordingly, the disclosure is considered to include any one or more of a computer-readable medium or a distribution medium, as listed herein and to include recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

In light of the forgoing description of the invention, it should be recognized that the present invention can be realized in hardware, software, or a combination of hardware and software. A method for determining a reference signal according to the present invention can be realized in a centralized fashion in one processing system, or in a distributed fashion where different elements are spread across several interconnected processing systems. Any kind of computer system, or other apparatus adapted for carrying out the methods described herein, is suited. A typical combination of hardware and software could be a general purpose computer processor, with a computer program that, when being loaded and executed, controls the computer processor such that it carries out the methods described herein. Of course, an application specific integrated circuit (ASIC), and/or a field programmable gate array (FPGA) could also be used to achieve a similar result.

Applicants present certain theoretical aspects above that are believed to be accurate that appear to explain observations made regarding embodiments of the present invention. However, embodiments of the present invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Given the exemplary embodiments described above, other implementations and modifications not explicitly described are also possible.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The following examples serve to illustrate the invention without limiting it thereby. It will be understood that variations and modifications can be made without departing from the spirit and scope of the invention.

Embodiments of the invention may be practiced without the theoretical aspects presented. Moreover, the theoretical aspects are presented with the understanding that Applicants do not seek to be bound by the theory presented.

Example 1

OCTRIMA: a Novel Tool for Automated Analysis and Interactive Quantitative Evaluation of Clinical Stratus OCT Data Software Implementation:

OCTRIMA was developed using the Matlab graphical user interface design environment (GUIDE) tool that allows interactive design of a graphical window along with variables and commands linked to it (The Mathworks, Natick, Mass.). Specifically, OCTRIMA is a research software application package that integrates the automated and semi-automated segmentation algorithm along with the manual correction tool into a user-friendly graphical user interface (GUI). The OCTRIMA software originally written in Matlab code is converted into C and requires the MatLab Component Runtime (MCR), which must also be installed on the end-user's computer. It also requires a PC with the WINDOWS™ operating system installed (Microsoft Corp., Redmond, Wash.). The application essentially provides dual functionality in a single software package by combining image enhancement and speckle denoising of Stratus OCT images along with intraretinal segmentation and error correction using direct visual evaluation of the detected boundaries. Moreover, the software has the capability to perform calculations based on measured values of corrected thickness and reflectance of the various cellular layers of the retina and the whole macula.

Software Description:

The design of OCTRIMA is partially based on the principles of encapsulation, which is the process of hiding all of the details of an object that do not contribute to its essential characteristics; typically the structure of an object is hidden, as well as the implementation of its methods. This is beneficial to both, the user and the developer, since the user does not need to know the internal architecture and the functionality of an object and the developer can improve implementation details without altering the interface. The user interface was mainly organized into panels that group GUI components and make the GUI easier to understand by visually grouping related controls. The GUI guides the user in an organized manner by activating only relevant functions and disabling other functions at any given time, achieved by effectively using the Matlab handles structure.

Data Import:

The input of the OCTRIMA software simply consists of two types of data files:
  the data file with the patient information (i.e. a text file exported from the Stratus OCT system)
  the raw scan data (i.e. the image file).
OCTRIMA facilitates the analysis of OCT images from two OCT scanning protocols: regular high-resolution and fast low-density mode. The built-in export function on the Stratus OCT system facilitates that a set of 6 files for each B-scan can be exported to a portable storage device:

Filename.txt (Patient information in ASCII text format)
Filename.raw (Raw scan or B-scan data in binary format)
Filename.bmp (Processed scan image in bitmap format)
Filename.vil (Fundus video image in bitmap format)
Filename.spd (Raw scan data in ASCII text format)
Filename.rnf (RNFL Thickness result in ASCII text format)

As previously mentioned, OCTRIMA only uses two types of data files: "Filename.txt" and "Filename.raw".

Detailed Menu Design

The file, view, data and help menus provide various options for:
 file management
 image data and segmentation results viewing
 image processing and quantitative analysis
 generating and exporting the results in various format
 comprehensive visual help.

As a general rule, the user has to choose an option from a pre-defined menu in OCTRIMA. This may include opening or loading image files and other data files to display an image on the screen or to perform calculations using information from the data file. For example, the various options in the file, view, data and help menus are available to the user and certain functions get activated during particular operations so that the user is well guided to choose a valid option from the limited active set of functions. Additionally, the user can choose to accept or reject the result generated by the program. Different interaction techniques are adopted to implement the choice from pre-defined options, such as push buttons, check boxes, text boxes, list boxes, popup menus and radio buttons.

File Menu:

The File menu provides options for OCT file operations such as loading, saving and viewing raw data (i.e. B-scans); printing options and the exit function to quit the GUI.

OCT scan files can be loaded in two different ways: 1. A new OCT B-scan that is yet to be segmented must be opened using the "New Segmentation Analysis" option, for preprocessing and segmenting the image. 2. A formerly segmented OCT B-scan that has corresponding saved segmentation data can be loaded using the second option for review. Once the scan to be reviewed is opened, the GUI automatically prompts the user to load the saved segmentation data file.

Multiple OCT B-scans can be loaded at once and viewed one at a time by using the review option in the file menu. In addition, the automated and semi-automated segmentation algorithm as well as the manual correction tool are able to process and modify the same OCT B-scan. Thus avoiding redundant steps such as loading the OCT B-scan file twice or saving the same data multiple times.

View Menu:

The user may choose to view the coherence enhanced image or the raw image from the View menu once the image has been preprocessed (see the demos in the video attached). The coherence enhanced image is obtained as result of filtering the image and also provides an additional visual tool to evaluate the quality of the corrections during the manual correction mode. The segmented layers can be viewed in an aligned manner with respect to the ONL, which gives the user an organized view of the OCT B-scan as well as the detected boundaries of the various cellular layers of the retina. The user is given the option to delete all the detected boundaries, if necessary, and restart the segmentation function or clear the segmentation for the RNFL on the left side or right side, if required. The delete operations as well as aligning of layers are each accompanied by an undo option in this menu.

Data Menu:

The Data menu consist of functions that use custom built algorithms developed for generating the report for quantitative analysis, exporting the numerical results (i.e. thickness and reflectance data) to a MS Excel spreadsheet and generating topographic and fractional loss maps for the retinal thickness of the overall macula and each intraretinal layer. In addition, a final report in PDF format can be also generated.

Help Menu:

The Help menu allows the user to view the OCTRIMA user guide, which explains in detail the functionalities of the software.

Figure 2:
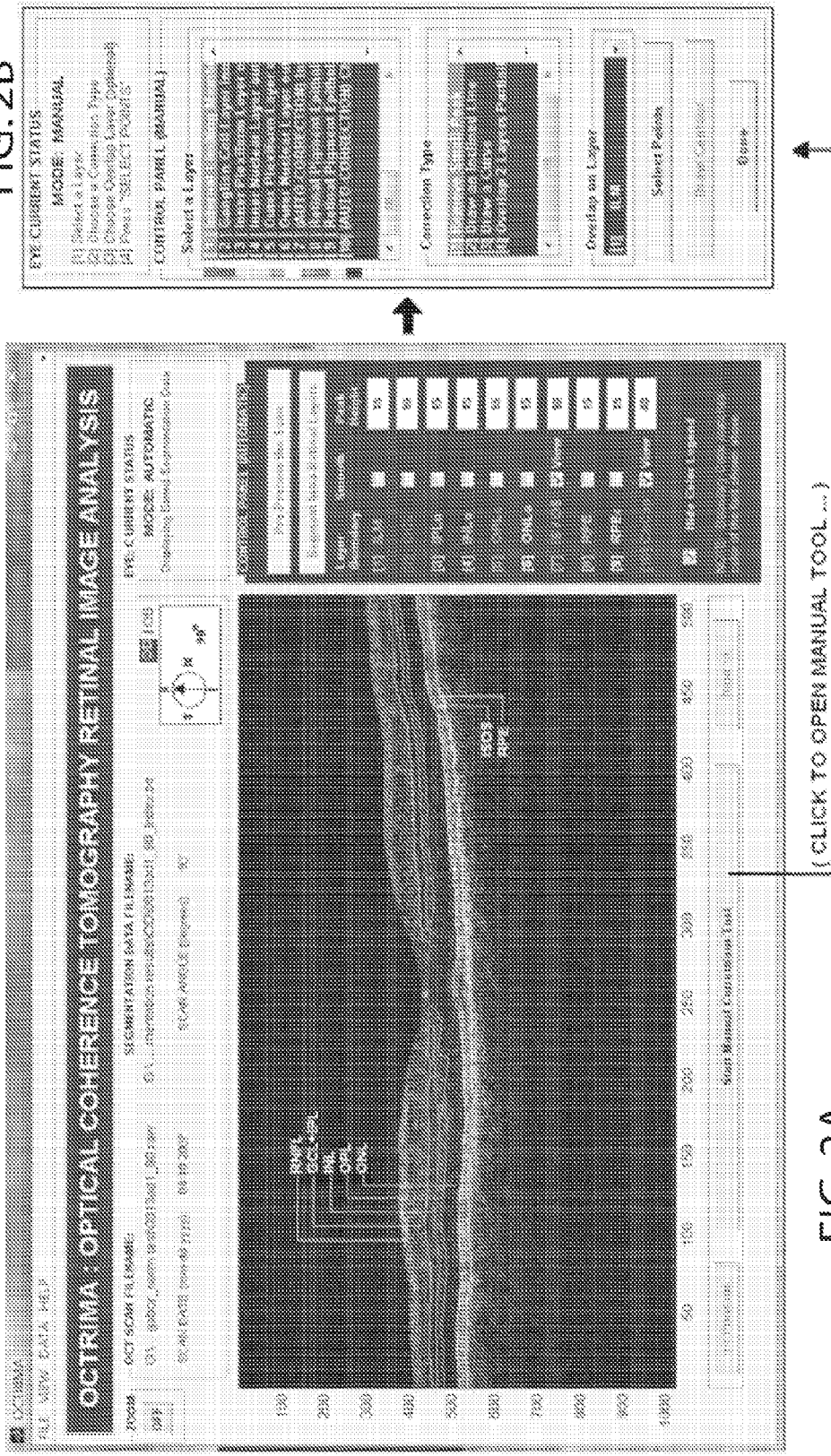
FIGS. 2A and 2B show photographs of an OCTRIMA screenshot.

OCTRIMA in Automated Mode:

FIGS. 2A and 2B show the OCTRIMA startup screen in the automated mode. The general information panel displays the name of the displayed OCT B-scan and its saved segmentation results as well as important subject and OCT B-scan information such as left eye (OS) or right eye (OD), scan date, the scan angle orientation (in degrees) and its pictorial representation. The subject and OCT B-scan information is automatically extracted from the text file which is exported along with the raw scan file from the Stratus OCT system. The detailed screen design for OCTRIMA in automated mode is as follows:

Main axes object: Displays the OCT B-scan data on the image grid.
 The "Status Panel" as well as message dialogue windows indicates the current status or prompts the user to execute the next processing step. The goal is to keep the user always updated about any process completions or results generated.
 The "Control Panel" in automatic mode facilitates the following functionalities: 1. Pre-processing of OCT raw data. The filtering of the speckle noise is performed during the preprocessing step. The pre-processing algorithm parameters are a set of invariant numerical values that already have been optimized and hence it is encapsulated and invisible to the user. More details of the denoising process can be found in Salinas et al. (*IEEE Transaction on Medical Imaging*, Vol. 26, Issue 06, pp. 761-71, 2007). 2. Automated segmentation of the various cellular layers of the retina. Segmentation is achieved by finding peaks on each sampling line using the structure coherence matrix. A total of eight intraretinal boundaries are automatically detected while the outer boundary of the IS/OS and a Choriocapillaris section are assumed at fixed distances using anatomical knowledge. Thus, a total of 10 boundaries are extracted. More details of the segmentation process can be found in Cabrera et al. (*Opt. Express* 13, 10200-16 (2005)). 3. Semi-automatic correction of discontinuities in each detected boundary after automated segmentation. This correction is performed by activating the following functions:
 "Smooth" Check boxes: Use input peak heights to correct error peaks in each corresponding boundary (see the Control Panel section in FIG. 2A). This function is used to correct discontinuous segments in a retinal boundary. A discontinuity is in place when two transversely adjacent pixels in the boundary are separated in longitudinal distance by more than 20 pixels. For example, spikes are typical discontinuities observed in OCT B-scans after automated segmentation. These discontinuities are corrected by approximating the boundary in the region of the discontinuity using linear interpolation (i.e. a straight line is drawn between the discontinuities in the region).

"Peak Height" Text boxes: Accept user input of peak heights for each boundary (see the Control Panel section in FIG. 2A). This functionality is used to select the discontinuous segments in each corresponding boundary that need to be corrected after automatic segmentation. The selection requires the information about the peak's heights the user wants to correct. Accordingly, the user has the choice to select the peaks or discontinuities per boundary that need to be corrected using the height information.

Zoom ON/OFF push button: Used for zooming in or out.

OCTRIMA in Manual Correction Mode

Segmentation of the object of interest is considered a difficult step in the analysis of medical images. Fully automatic methods sometimes fail, producing incorrect results and requiring the intervention of a human operator. This is often true in ophthalmic applications such as OCT where image segmentation is particularly difficult due to restrictions imposed by image acquisition, ocular pathology and biological variation. Consequently, the intervention of a human operator is often needed to correct the segmentation result manually. Strategies that allow a trained human expert to correct segmentation errors may provide a suitable mechanism for increasing the precision of retinal measurements for monitoring patients with macular disease, particularly in clinical trials.

Computer aided manual correction of OCT segmentation may be useful for correcting thickness measurements in cases with errors of automated retinal boundary detection and, may also be useful for quantitative analysis of clinically relevant features, such as the volume of subretinal fluid and intraretinal fluid-filled regions. It is well known that the lines drawn by the detection algorithms in the current commercial Stratus OCT system are frequently and dramatically erroneously drawn, which can lead to inaccurate measurements of retinal thickness. Thus, there is a need for developing efficient, user-friendly software tools that will supplement fairly accurate automated boundary detection algorithms to generate more precise segmentation of the various cellular layers of the retina. For example, an interactive procedure could be activated, by means of which the user edits the segmentation directly or provides extra information to reconfigure the computational part. If the result generated by the computational part is wrong, the user can correct it directly using a manual editor.

In OCTRIMA, the manual corrections tool is initialized by clicking the push button located below the main figure in the automated mode (see FIG. 2A). The button to start the manual corrections tool, when clicked, is programmed to display the manual control panel and hide the automated control panel while maintaining the current state of the GUI. The menu options and scan information panel remain unchanged while the options for layer selection and corrections are displayed in the manual control panel (see FIG. 2B). The current status panel indicates the general flow of steps while using the manual tool. Opening a new OCT B-scan file or clicking the "Done" button causes the GUI to switch back to automated mode primarily by changing the control panel display.

The detailed screen design for OCTRIMA in manual correction mode is as follows:

Main axes object: Displays the OCT B-scan data on the image grid

"Previous" and "Next" Push buttons: Allow navigation between multiple scans for any specific subject Zoom ON/OFF push button: Used for zooming in or out.

The control panel in manual mode facilitates the different manual corrections: 1. "Select a Layer" List box: Choose a layer to correct errors, if any. Semi-automated boundaries, such as the IS/OS junction and the Choriocapillaris cannot be manually corrected in this OCTRIMA software version since they are assumed to be located at constant distances from the ONL and the RPE outer boundary respectively (see FIGS. 2A, 2B). 2. "Correction type" List box: Choose a correction type. 3. "Overlap on Boundary" Popup menu: Select an overlapping boundary. 4. "Draw Contour" Push button: Trace the boundary of specific regions in pathological cases such as macular holes, subretinal fluid and macular cysts using a customized curve plotting algorithm. This functionality is also used in cases with a complete absence of a retinal boundary in some portion of the image. This condition would usually occur with 1) blood vessels or hard exudates which caused shadowing and loss of the reflections from the RPE and choroid, or 2) patient blinks which caused a complete loss of signal during the blink.

"Done" Push button: Return to automatic mode.

Overview of the Manual Corrective Functions:

Various functions were implemented to assist the user in correcting retinal segmentation errors resulting from the automated and semi-automated segmentation process. All the functions and algorithms used in the manual correction process display the delineation of the retinal boundaries on the screen, enabling the user to instantly evaluate its location on the image grid. Different visualization schemes are adopted, such as to show the detected layers as well as the corrections in color for better discrimination from the grey image in the background.

Figure 3:
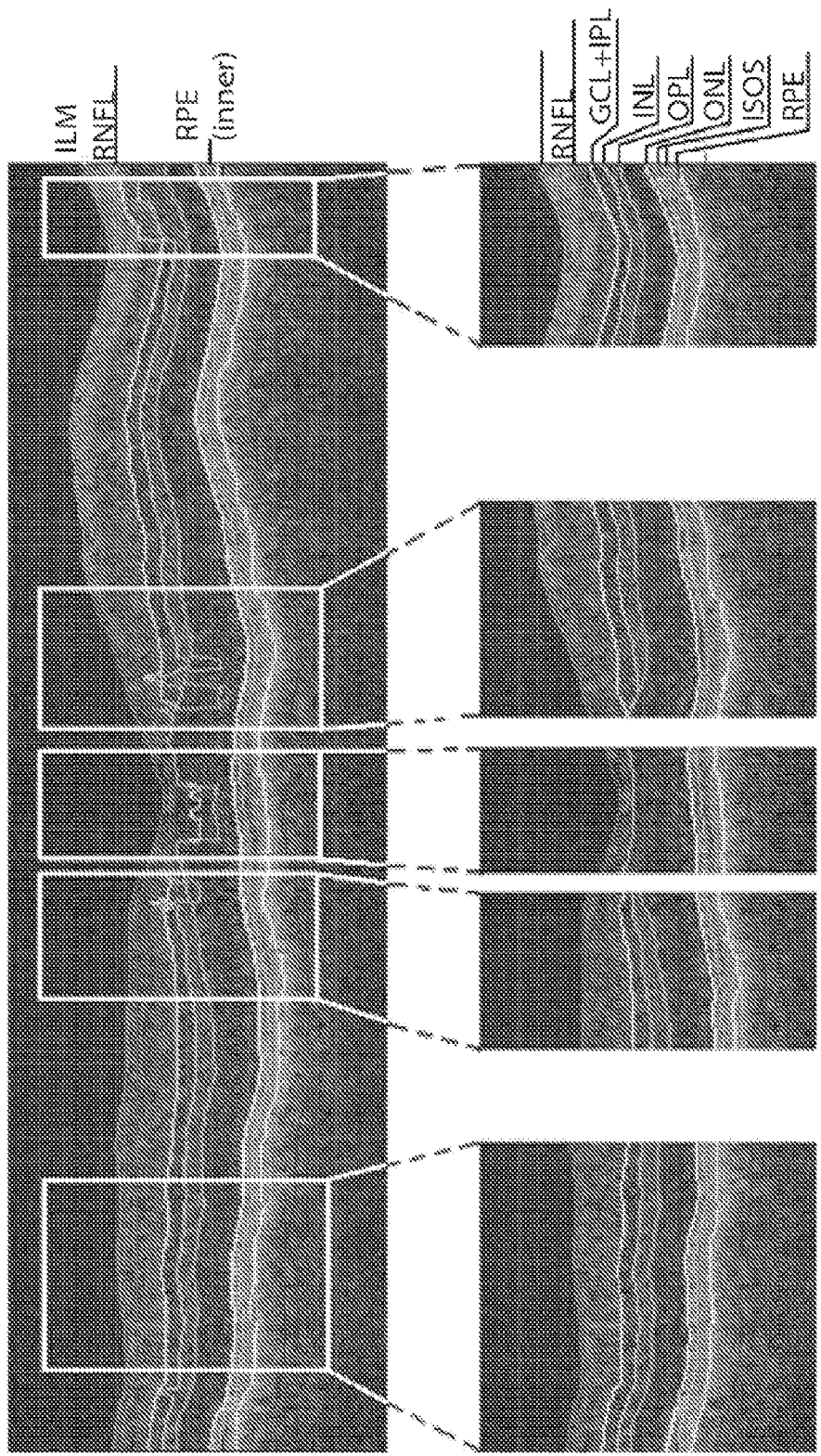
FIGS. 3A to 3F are photographs showing a segmented B-scan (horizontal radial line scan, right eye) before and after applying manual corrections.
Figure 4:
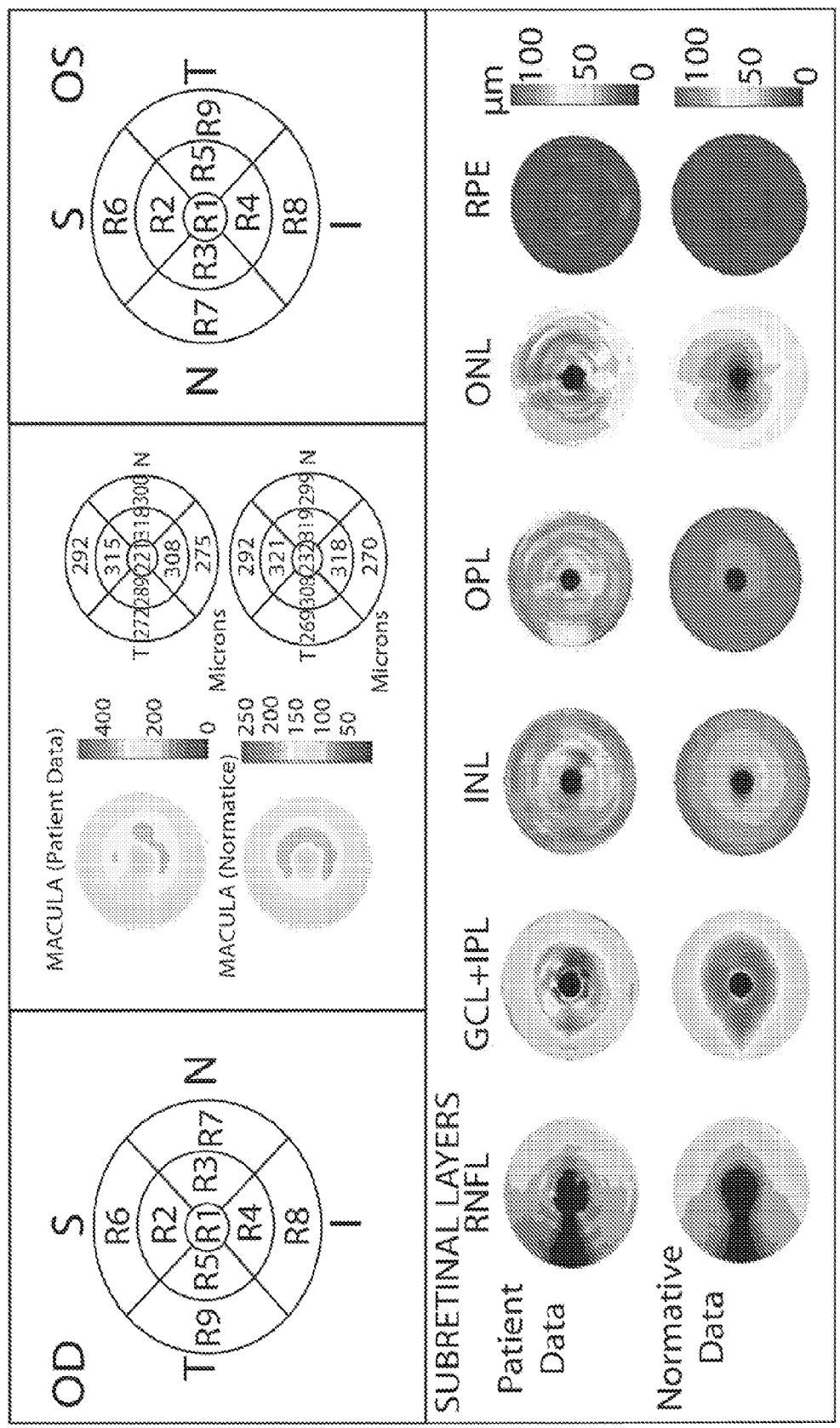
FIG. 4 is a photograph showing an OCTRIMA software screenshot showing the quantitative analysis results for a diabetic patient (OD). Thickness maps are shown for the macula (i.e. total retina) and intraretinal layers. The normative data was composed using OCT data from 74 healthy eyes (34±16 years). The nine ETDRS macular regions are: R1—Fovea, R2—Superior Timer Macula, R3—Nasal Inner Macula, R4—Inferior Inner Macula, R5—Temporal Inner Macula, R6—Superior Outer Macula, R7—Nasal Outer Macula, R8—Inferior Outer Macula and R9—Temporal Outer Macula.

These errors are mainly due to both the presence of high reflectivity regions in the inner retina and loss of retinal structure information in local regions along the retinal cross-section as visualized by the commercial OCT system. The errors are classified as: (a) False Segmentation—It refers to the falsely detected inner and/or outer boundaries of an intraretinal layer. This particular error is most commonly found during the RNFL detection. This happens because the reflectance of the RNFL is highly directional and depends strongly on the angles of illumination and viewing. Specifically, there are certain cases in which the true anatomical thickness of the RNFL layer (or some regions of the RNFL layer) might be negligible. In other cases, one side of the RNFL layer is completely invisible in the OCT image, like for example in the horizontal B-scans. In such cases, a correction is required to overlap the inner and outer boundaries of the RNFL layer in the regions of negligible thickness (see, FIGS. 3C and 3D). However, sometimes the boundary detection algorithm fails in such specific cases when localized bright spots of high intensity appear on some regions of the RNFL layer; and falsely displays the outer boundary of the RNFL layer as a result of the peak search algorithm which looks for zero crossings in the structure. Hence, the RNFL outer boundary must be manually corrected to appear overlap the inner boundary in the invisible part of the layer. As can be seen in FIG. 3B, the ILM boundary on the inner side of the RNFL is detected but no boundary is detected on the outer left side since the RNFL is not visible on this side for this particular scan, whereas the RNFL is bright and clearly visible on the right side of the scan (see FIGS. 3A and 3B).

Additionally, a predefined control is also in place for the inner retinal layers in a 1.5 mm diameter zone in the fovea, where retinal reflections are minimally visible. The control forces the ILM, the inner and outer side of the GCL+IPL complex, and the outer side of the INL and OPL to be coincident in this region (see FIG. 3A). Sometimes, small peaks appear at the periphery of this controlled foveal region. In such a case, it appears that the coincident layers deviate from the true foveal visible boundary and need to be corrected so that they overlap in the periphery of the controlled foveal region. Thus, the overlap function of the manual correction software tool is useful to rectify the segmentation at the fovea (see FIG. 3D).

Small Peaks:

Small peaks refer to tiny overshoots or undershoots visible along an intraretinal boundary, resulting in inaccurate segmentation (e.g. FIG. 3A shows small peaks in the boundaries outlined in yellow and cyan). The user's visual information about the peak height (in pixels) is used to remove the peaks after the automated segmentation results are obtained. However, the peak height once selected by the user is assumed the same along the entire length of each independent layer. As a result, not all peaks along the boundary can be removed at once. Thus, additional manual interaction is required in order to completely correct the small peak errors. The "small peak" corrective function of the manual correction software tool removes the overshoots or undershoots in the individual boundaries. For example, FIG. 3C shows the manually corrected outer boundary of the IPL (outlined in yellow). In this case, the user is required to manually select the starting and ending points of the peak and these two points are joined to remove the peak.

Linear Offsets:

These are parts of a boundary that form a straight line segment but are incorrectly detected as a peak or an elevated or depressed line segment by the automated segmentation algorithm. To resolve this class of errors, the user has to manually select two points to draw a straight line segment on the specific boundary containing the offset. For example, a straight line segment was manually drawn to correct the linear offset in the outer boundary of the OPL (see the boundary outlined in green in FIG. 3E).

Curve Offsets:

Curve offset is a term given to the curved portion of a boundary that has not been recognized as a curve, instead, has been incorrectly segmented as an elevated or depressed curve. For example, FIG. 3F shows the manual corrections for the inner and outer boundaries of the INL (outlined in yellow and cyan, respectively) which had segmentation errors as a result of curve offsets (see FIG. 3A). The curve offsets have been rectified using a function based on a customized contour model which was originally introduced to identify non-convex shapes in OCT images. This function allows the user to select multiple closely spaced points that will be joined to trace a curve and remove the offset. FIG. 3F shows the result of the curve plotting function applied to correct the inner and outer boundaries of the INL (outlined in yellow and cyan, respectively).

Manual Detection of Visible Convex Shaped Structures:

The manual correction software tool is designed to overcome the limitations of the automated and semi-automated segmentation algorithm, not only in terms of error correction in detected intraretinal boundaries but also to allow the user to trace the internal boundary of visible non-convex shaped structures such as intraretinal and subretinal fluid-filled regions, if present and visible on the OCT B-scan.

Data Export:

All the analyzed results can be saved as tab delimited text files for user's convenience. These results are also mapped to specific cells in a Microsoft Excel template. Once the data is loaded in the template, the file is saved with a user specified filename. The template consists of four data analysis fields: 1) analysis per scan, 2) analysis per region; 3) analysis of the overall macula per scan, and 4) analysis of the overall macula per region. The output data includes three main quantitative measures: thickness, volume and reflectance. Additionally, topographic maps of the extracted thickness for the overall macula and each intraretinal layer can be created by selecting the "Generate Topographic Maps" option under the Data menu. These maps are obtained according to the standards set by the Early Treatment Diabetic Retinopathy Study (ETDRS) similarly to the Stratus OCT analysis software and can be easily exported to a PDF document along with the numerical results in tabulated format. A topographic map of the thickness fractional loss in percent is also available. This particular map provides the deviation from the norm. The OCTRIMA's norm was obtained from 74 healthy eyes (34±16 years).

It is noted that the analysis of the overall macula per scan and per region is based on mean values of thickness measured between the ILM and the inner boundary of the RPE layer, which follows the true anatomical position of the inner and outer border of the retina. Moreover, once the intraretinal layers are automatically segmented, the relative reflectance and thickness of these layers at the individual points (i.e. at each of the 512 A-scans) are averaged to yield a mean "raw" measurement of thickness and reflectance per layer. Since the absolute reflectivity can vary according to a wide variety of factors, such as media opacity or scan technique, each reflectivity value is a percentage of the local maximum. In this way, it is possible to compare different scans in the same patient or subject or even among different patients, different operators or OCT machines.

Additional OCTRIMA-Based Measures:

OCTRIMA also offers objective and intuitive additional functions for evaluating and comparing the efficacy of different therapeutic modalities. Since normative data for OCT analysis are crucial to compare various treatment strategies, OCTRIMA facilitates normative data and also allows the user to create a new norm. Specifically, the OCTRIMA's norm is based on data from 74 healthy subjects (34±16 years).

In addition, OCTRIMA provides a standardized method for reporting changes in thickness as a percentage of total possible change based on normative OCT data. The "Calculate standardized thickness change" function calculates the total percentage improvement observed in the patient using the segmentation results before and after treatment. These two OCTRIMA-based measures can be found under the Data menu.

Example 2

Early Detection of Retinal Thickness Changes in Diabetes Using Optical Coherence Tomography The purpose of this study was to explore the ability of intraretinal layer segmentation to locally detect early retinal changes in diabetic patients using OCT, and determine whether OCT can be used to understand the early histological changes of the macula in diabetes by comparing the thickness of the various cellular layers of the retina in diabetic patients who have no retinopathy with the thickness in patients with minimal DR.

Materials and Methods

Subjects:

A total of 50 eyes of 38 patients with diabetes mellitus (DM) with no or minimal diabetic retinopathy (MDR) (39 eyes no DR [DM; 36±10 years] and 11 eyes with minimal DR [MDR; 61±20]) on biomicroscopy were included in this study. Glycosylated hemoglobin (HbA1c) level for DM patients was 7±1 (mean±SD); and the presumed duration of DM (from the time of diagnosis to the time of examination) was 22±8 years. DM patients underwent a complete ophthalmologic examination and fundus photography. The inclusion criteria considered diabetic patients with no DR or with the presence of at least one microaneurysm or hemorrhage in the central retina but no other diabetic lesions (i.e. minimal retinopathy), but in all cases without clinical signs of macular edema (CSME). Exclusion criteria were the presence of proliferative disease, CSME, anatomic abnormalities and media opacities that could distort macular architecture, such as vitreoretinal traction, cataract and epiretinal membranes. In addition, patients with visual acuity less than 20/25 and with previous diagnosis of glaucoma, uveitis, or retinal disease were excluded from the study. Written informed consent was obtained from all participants. Procedures followed the tenets of the Declaration of Helsinki, and were approved by the institutional ethics committee.

Figure 5A:
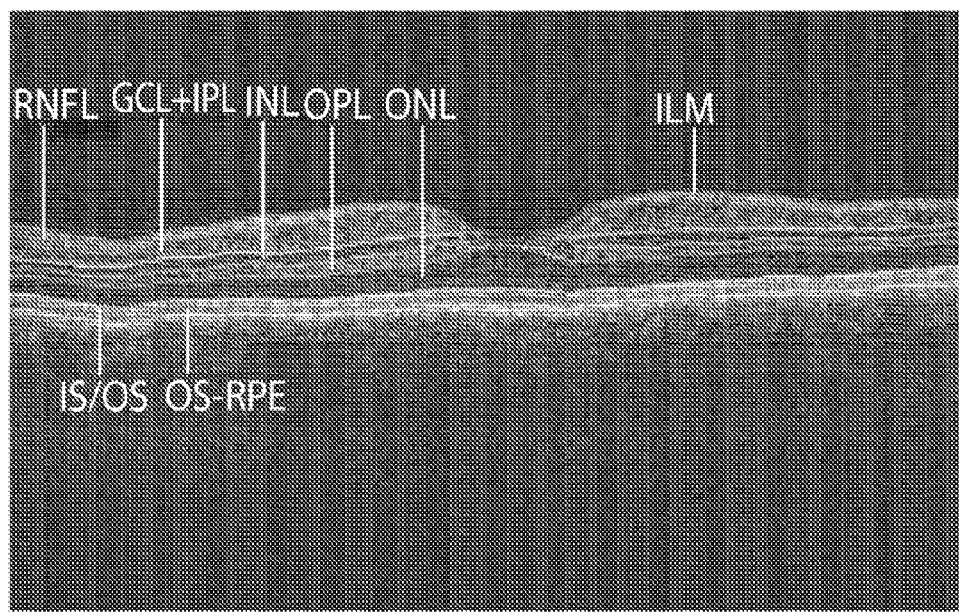
FIG. 5A shows the automatic segmentation results obtained for a 6 mm diameter retinal scan at 90 degrees (radial lines protocol) through the fovea for a diabetic patient (51 years old, OD) with mild retinopathy. The boundaries detected are superimposed on the original OCT image, for the abbreviations see the text. Segmentation results were performed using OCTRIMA software.

Optical Coherence Tomography Imaging and Data Analysis:

For imaging purposes the commercially available Stratus OCT unit (software version 4.0; Carl Zeiss Meditec, Inc., Dublin, Calif.) was used. This imaging system is based on the principle of optical low-coherence interferometry that measures the echo time delay and intensity of backscattered light and thus resolves the position of reflective or optical backscattering sites within a tissue sample. OCT is a fiber-optic based, non-contact and non-invasive imaging system with a high resolution of <10 μm which is one to two orders of magnitude finer than standard ophthalmic ultrasound. The radial lines protocol was used for each subject. The OCT raw data were exported for automatic/semiautomatic subanalysis and quantification of intraretinal layers using a custom-built OCT retinal image analysis software (OCTRIMA) written in Matlab 7.4 (MathWorks, Natick, Mass.). OCTRIMA is a powerful computer-aided system designed to facilitate viewing and automatic/semiautomatic OCT retinal image analysis (Cabrera Fernandez D, et al., Invest. Ophthalmol. Vis. Sci. 49, 2008; pp. 2751). The application provides dual functionality in a single software package by combining image enhancement and speckle denoising of Stratus OCT images along with intraretinal segmentation and error correction using direct visual evaluation of the detected boundaries. Moreover, the software has the capability to provide quantitative analysis based on measured values of corrected thickness, volume and reflectance of the various cellular layers of the retina. A total of seven intraretinal layers can be extracted using OCTRIMA, namely, the retinal nerve fiber layer (RNFL), the ganglion cell layer along with the inner plexiform layer (GCL+IPL), the inner nuclear layer (INL), the outer plexiform layer (OPL), the outer nuclear layer (ONL), the photoreceptor inner/outer segment (IS/OS) junction; and the photoreceptor outer segment/retinal pigment epithelium (OS/RPE) junction (see FIG. 5A). Since the border between GCL and IPL could not be differentiated on most scans, the combined thickness was measured as GCL+IPL. In addition, topographic maps of the extracted thickness in 9 ETDRS (Early Treatment Diabetic Retinopathy Study) areas for the overall macula and each intraretinal layer can be obtained similarly to the Stratus OCT analysis software (see FIG. 5B). ETDRS areas include a central 1-mm disc, representing the foveal area, and inner and outer rings of 3 and 6 mm, respectively. The inner and outer rings are divided into four quadrants: superior, nasal, inferior, and temporal.

Stratus OCT uses segmentation algorithms to mark the ILM as the inner boundary and the photoreceptor inner segment/outer segment (IS/OS) junction as the outer boundary. Particularly, the Stratus OCT system images the outer retinal layers (RPE-photoreceptor complex) as two hyperreflective bands: 1) the photoreceptor inner/outer segment junction and 2) RPE-choriocapillaris complex. The segmentation software of the Stratus OCT system uses the anterior border of the most inner hyperreflective band (i.e. photoreceptor inner segment/outer segment junction) as the border of the outer retina for calculating the total retinal thickness. OCTRIMA detects the outer retinal boundary as the anterior border of the second hyperreflective band, which is thought to represent the tip of the cone outer segment in the fovea. Thus, OCTRIMA calculates the total retinal thickness as the distance between the vitreoretinal interface (ILM) and the anterior boundary of the second hyperreflective band corresponding to the OS/RPE junction (see FIG. 5A).

After each B-scan was denoised, the inner and outer borders of the retinal structure were identified between the ILM and OS/RPE junction (inner boundary); and a total of seven intraretinal layers were extracted using OCTRIMA. All scans in the study had signal strength of 9 or 10. Although OCTRIMA is also able to analyze images from SDOCT devices, the algorithm used in this study was optimized for Stratus OCT images. Algorithm performance was visually evaluated to detect algorithm errors. Criteria for algorithm error included evident disruption of the detected boundary (e.g. small peaks, linear and curve offsets), and/or detected boundary jumping to and from different anatomical structures (i.e. false segmentation). The average number of manual corrections needed per scan was three.

Statistical Analysis:

Mean values of retinal thickness of the macula and intraretinal layers in the central, pericentral and peripheral macular regions in the diabetic patients with no DR were compared with those in patients with MDR. Regional total retinal thickness was also recorded and compared for the DM and MDR groups. Comparisons between groups were made using Mann-Whitney U test. Because of the number of statistical comparisons made in the study, a modified p value of <0.001 was considered statistically significant. Statistical analyses were performed using Statistica 8.1 (Statsoft Inc., Tusla, Okla.)

Results

Fundus photography showed either no abnormalities or only few microaneurysms in the posterior pole in DM patients. It was confirmed that the measured local thickness of the intraretinal layers was consistent with known retinal anatomy for the diabetic patients. For example, in the diabetic patients with no DR, the GCL+IPL showed maxima in thickness just outside the fovea, while the RNFL increased in thickness between the foveal center and the optic disc. In addition, these layers were decreased in thickness in patients with MDR. Table 1 shows the mean total macular thickness and standard deviation for each study group as measured by OCTRIMA for each ETDRS region separately. A decrease in average total macular thickness was measured with the OCTRIMA software in all areas (R1-R9) for eyes with minimal DR.

Mean intraretinal layer thickness values and total macular thickness (μm) that showed a statistically significant difference (p<0.001) between diabetic eyes with no DR and eyes with MDR are shown in Table 2. When comparing eyes with MDR to diabetic eyes with no DR, a reduced RNFL thickness was found in the pericentral and peripheral macular regions, and reduced thickness of the GCL+IPL in the pericentral region of the macula (p<0.001). Particularly, a 33% and 21% decrease in RNFL was found in the pericentral and peripheral macular regions, respectively, while the GCL+IPL decreased by 13% only in the pericentral region. Total macular thickness was also reduced in the pericentral and peripheral region of the macula (see Table 2). The central part of the macula (mainly corresponding to the fovea) was not affected by early diabetes (see Tables 1 and 2). RPE thickness of the central region may be somewhat affected in the MDR group when compared with the DM group, however this difference did not reach the significance level set in the study.

Discussion

A custom-built algorithm (OCTRIMA) was used to measure the local thickness of the intraretinal layers seen in Stratus OCT images of patients with no and minimal DR. The main interest of this study was in the thickness differences between diabetic patients with no and minimal DR. In particular, the question was whether it was feasible to measure early changes of the macula in diabetes using OCT. In general, the results are encouraging. The present study demonstrates that a software algorithm designed to automatically segment and quantify intraretinal layers of clinical interest on two dimensional OCT images is feasible for locally detecting early retinal changes in diabetic patients using OCT.

In this study it was found that the RNFL and GCL+IPL complex was thinner in DM and MDR eyes than in normal healthy eyes. However, a different assessment was performed in this study by comparing thickness measurements of diabetic eyes without the presence of retinopathy to eyes with minimal diabetic retinopathy. Particularly, it was found that local measurement of the retinal thickness by OCT may provide useful information about the changes of the intraretinal layers in diabetic patients. These results evidence that the RNFL and GCL+IPL complex are more susceptible to initial damage when comparing MDR with DM eyes. This may reflect neurodegenerative changes in the diabetic retina. The trend observed for the thickness of the RNFL and GCL+IPL in MDR eyes might be associated with pathological metabolic changes in the retina. These findings also have possible implications for early detection of macular damage in diabetes. Because the macular region is rich in retinal ganglion cells, it could be that diabetic damage of this central region might occur early in the disease process. In fact, animal models of DR show significant loss of macular ganglion cells.

The strength of this study compared to other studies using Stratus OCT data is the OCTRIMA subanalysis and quantification of the local variations of the intraretinal layers. However, a larger study to evaluate these findings on a greater scale and a more homogeneous data set is required in the future. Despite the worse resolution and scanning time of Stratus OCT systems, comparable thickness measurement differences could be obtained with the recent introduced SDOCT devices. Algorithms have been proposed for segmenting the various cellular layers of the retina and analyzing images from any SDOCT device. However, it is possible to obtain local thickness measurements of the intraretinal layers observed in SDOCT images using OCTRIMA. In summary, the results herein, support this hypothesis and also sustain the view of neurodegeneration in diabetes in the early stage of DR which seems to involve the ganglion cells and cells of the inner plexiform layers mostly, leading to reduced total retinal thickness.

Conclusions

The in vivo human data, may underline the findings of neural apoptosis due to diabetes and may also support the view of diabetic retinopathy as an—at least partly—neurodegenerative disease. This study comparing thickness measurements between diabetic eyes with no DR to MDR eyes demonstrates that local measurement of the retinal thickness by OCT appears to be a proper index for early DR detection and neuroprotection. The local changes in the retinal structure of the diabetic retina could be helpful in finding a surrogate for following development of retinopathy affecting vision. Moreover, it may also be possible to determine which cellular layer(s) of the retinal structure is (are) involved in diabetic retinopathy and whether there is any rule concerning which layer(s) will get damaged first. A larger study will be conducted to evaluate the present findings on a greater scale. In addition, intraretinal layer segmentation may eventually be useful in testing new drugs once it could be demonstrated that changes in the diabetic retina could be used as surrogates for subsequent progress of retinopathy inducing visual defects.

Intraretinal layer quantification on OCT images may greatly help the understanding of macular pathophysiology in health and disease and may soon become a daily diagnostic tool of the comprehensive ophthalmologist with the future development of both OCT hardware and software.

As this study revealed, the preceding step of manifest DR may be a neurodegeneration of the retina which seems to be detectable in vivo by OCT mapping of the local retinal abnormalities and corresponds to previous experimental results. This aspect of diabetic retinal changes is not yet a part of the common thinking about diabetes, but future studies using OCT image segmentation techniques, elaborating histological and functional changes of the macula in diabetic patients may shed light on this very first step possibly leading to the further sequelae of DR.

TABLE 1

Descriptives and total macular thickness (mean ± SD: [min-max]) measurements obtained for each study group (Mann Whitney U test, ‡ $p < 0.001$, and missed significance † $p < 0.05$).

| Descriptives | Study Groups | |
| --- | --- | --- |
| | DM | MDR |
| Number of eyes | 39 | 11 |
| Mean age (SD), yr | 36 ± 10 | 61 ± 20 |
| Female | 19 | 6 |
| Male | 20 | 5 |
| Total macular thickness (µm) | mean ± SD [min-max] | |
| Foveal center (ETDRS central region: R1) | 248 ± 23 [213-326] | 240 ± 18 [208-278] |
| Inner circle (ETDRS pericentral region range: R2-R5) | | |
| Superior (R2)‡ | 326 ± 11 [283-364] | 302 ± 11 [261-329] |
| Temporal (R5)† | 312 ± 10 [276-352] | 296 ± 6 [262-322] |
| Inferior (R4)† | 321 ± 9 [277-356] | 298 ± 7 [256-325] |
| Nasal (R3)† | 327 ± 11 [285-368] | 305 ± 10 [268-343] |
| Outer circle (ETDRS peripheral region range: R6-R9) | | |
| Superior (R6)† | 289 ± 15 [251-325] | 277 ± 13 [251-312] |
| Temporal (R9)† | 269 ± 20 [233-295] | 258 ± 18 [240-294] |
| Inferior (R8)† | 269 ± 18 [232-288] | 254 ± 17 [233-279] |
| Nasal (R7)† | 298 ± 14 [261-328] | 280 ± 14 [252-304] |

DM: diabetic eyes with no DR,
MDR: eyes with minimal diabetic retinopathy.

TABLE 2

Mean intraretinal layer thickness values and total macular thickness (μm) that showed a statistically significant difference (Mann-Whitney U test, ‡ p < 0.001, and missed significance † p < 0.05) between diabetic eyes with no DR (DM) and eyes with minimal diabetic retinopathy (MDR). Values reported are mean ± SD [range].

| Macular Region | Intraretinal Layer | DM | MDR |
|---|---|---|---|
| Central | OS/RPE junction | 16 ± 2 [13-22] | 15 ± 2† [11-17] |
| Pericentral | RNFL | 27 ± 2 [21-32] | 18 ± 5‡ [11-24] |
| | GCL + IPL | 92 ± 7 [78-104] | 80 ± 10‡ [61-94] |
| | Macula | 322 ± 16 [280-360] | 298 ± 20‡ [262-321] |
| Peripheral | RNFL | 42 ± 3 [35-48] | 33 ± 9‡ [20-48] |
| | Macula | 282 ± 13 [244-309] | 267 ± 14‡ [246-295] |

Example 3

Assessment of Intraretinal Light-Backscatter in Eyes with No or Minimal Diabetic Retinopathy Using Optical Coherence Tomography Purpose:
To assess the light-backscatter of intraretinal layers in normal and diabetic eyes with no or minimal diabetic retinopathy using Optical Coherence Tomography (OCT).

Methods:
Standard macular mapping by Stratus OCT were performed in 74 healthy eyes (34±16 years) and 26 eyes with diabetes mellitus (DM) with no or minimal diabetic retinopathy (19 eyes no DR [DM; 32±9 years] and 7 eyes with minimal DR [MDR; 63±18]) on biomicroscopy. Automatic layer segmentation was performed using a custom-built algorithm. Mean values of thickness and relative light-backscatter of the RNFL, GCL+IPL, INL, OPL, ONL, IS/OS and RPE in healthy normal, DM and MDR eyes were compared using ANOVA followed by Newman-Keuls post hoc analysis. A p value of <0.05 was considered statistically significant.

Results:
Relative light-backscatter was significantly less in DM eyes than in normal (p<0.05 for all the layers except ISOS). However, thickness of the RNFL, ONL and ISOS was not significantly less in DM than in controls. Relative light-backscatter was significantly less in MDR eyes than in normal for only the RNFL, ISOS and RPE (p<0.05). Nevertheless, thickness of the GCL+IPL, OPL and ONL was significantly less in MDR than in healthy eyes. Relative light-backscatter and thickness in the GCL+IPL, INL, OPL and ONL was significantly more in MDR than in DM eyes (p<0.05). No significant differences in light-backscattering between DM and MDR eyes were obtained for ISOS and RPE. There was no difference in RNFL relative light-backscatter and thickness between DM and MDR eyes (45±8% vs. 45±6%, p=0.96; and 41±3 μm vs. 42±4 μm, p=0.38; respectively). On the contrary, RNFL's light-backscatter was significantly less in eyes with DM and MDR than in normal eyes. Moreover, GCL+IPL's thickness in MDR eyes showed a tendency towards thinning as compared with normal and DM eyes. Conversely, ONL and OPL's thickness showed an increasing trend in the MDR group.

Conclusions:
Our results suggest that the GCL+IPL complex is more susceptible to initial damage than RNFL when comparing MDR with DM eyes. This may reflect neurodegenerative changes in the diabetic retina. The trend observed for the GCL+IPL's thickness and its relative light-backscattering in MDR eyes might be associated with pathological metabolic changes in the retina. Light-backscattering along with thickness information of the various cellular layers of the retina may provide useful information about the pathological changes in retinal morphology.

Example 4

Evaluation of Intraretinal Scattering Measurements in Eyes of Healthy and Type 1 Diabetic Subjects with No Retinopathy Using Optical Coherence Tomography Purpose:
To assess the scattering measurements of the intraretinal layers in healthy normal and type 1 diabetic eyes using optical coherence tomography (OCT).

Methods:
Unprocessed raw scan data were exported from the Stratus OCT machine after performing standard macular mapping in 74 healthy eyes (34±16 yrs, 51 female, 23 male) and 39 eyes with type 1 diabetes mellitus (DM) with no retinopathy (36±10 yrs, 19 female, 20 male) on biomicroscopy. Automatic layer segmentation was performed using a custom-built algorithm (OCTRIMA). Mean values of relative internal reflectivity (RIR) and reflectivity with normalization to the RPE reflectance (NRPE) were used in the comparisons. Mean light-backscattering, contrast measures and scattering coefficients of the RNFL, GCL+IPL, INL, OPL, ONL, IS/OS and OS/RPE junction were calculated. The scattering coefficients were calculated using a finite difference method. Mann-Whitney U test was used to test for differences between the two groups. A modified p value of <0.001 was considered statistically significant. Missed significance (MS, 0.001<p<0.05) was also recorded.

Results:
Scattering coefficients were significantly different between DM and healthy eyes for the IS/OS and OS/RPE junction for both types of normalization used (RIR: 9.84±2.05 mm$^{-1}$ versus 8.49±1.12 mm$^{-1}$ and 10.44±1.59 mm$^{-1}$ versus 9.84±1.41 mm$^{-1}$, ‡p<0.001, respectively and; NRPE: 12.80±1.94 mm$^{-1}$ versus 14.19±3.02 mm$^{-1}$ and 14.69±2.34 mm$^{-1}$ versus 15.18±2.71 mm$^{-1}$, ‡p<0.001, respectively). The mean light-backscattering and contrast measures between DM and healthy eyes were not significantly different.

Conclusions:
These results evidence that the optical properties of the intraretinal layers may provide useful information about the extent of intraretinal layer injury in diabetes. Diabetes inflicts structural damage to the inner retinal segment supported by the thinning of the ganglion cell complex (RNFL+GCL+IPL). However, it appears that diabetes also inflicts additional damage to the outer retinal segment demonstrated by the optical changes of the IS/OS and OS/RPE junction.

Example 5

Comparing Intraretinal Scattering Measurements Between Eyes of Healthy Subjects and Type 1 Diabetic Patients with No or Minimal Diabetic Retinopathy Using Optical Coherence Tomography Purpose:
To assess the scattering measurements of the intraretinal layers in healthy normal and type 1 diabetic eyes using optical coherence tomography (OCT).

Methods:

Unprocessed raw scan data were exported from the Stratus OCT machine after performing standard macular mapping in 74 healthy eyes (34±16 yrs, 51 female, 23 male), 39 eyes with type 1 diabetes mellitus (DM) with no retinopathy (36±10 yrs, 19 female, 20 male) and 11 eyes with type 1 diabetes mellitus with minimal (MDR) retinopathy (61±20 yrs, 6 female, 5 male) on biomicroscopy. Automatic layer segmentation was performed using a custom-built algorithm (OCT-RIMA). Mean values of relative internal reflectivity were used in the comparisons. Mean light-backscattering and scattering coefficients of the RNFL, GCL+IPL, INL, OPL, ONL, IS/OS and OS/RPE junction were calculated. The scattering coefficients were calculated using a finite difference method. Newman-Keuls test was used to test for differences between the three groups. A modified p value of <0.001 was considered statistically significant. Missed significance (MS, 0.001<p<0.05) was also recorded.

Results:

Scattering coefficients were significantly different between MDR and healthy eyes for the IS/OS and OS/RPE junction (7.59±1.71 mm$^{-1}$ versus 8.49±1.12 mm$^{-1}$ and 12.14±1.97 mm$^{-1}$ versus 9.84±1.41 mm$^{-1}$, $^{\ddagger}$p<0.001, respectively). Significant differences were also found between MDR and DM eyes for the IS/OS and OS/RPE junction (7.59±1.71 mm$^{-1}$ versus 9.24±1.74 mm$^{-1}$ and 12.14±1.97 mm$^{-1}$ versus 9.94±1.69 mm-1, $^{\ddagger}$p<0.001, respectively).

Conclusions:

These results evidence that the optical properties of the intraretinal layers may provide useful information about the extent of intraretinal layer injury in diabetes. Diabetes inflicts structural damage to the inner retinal segment supported by the thinning of the ganglion cell complex (RNFL+GCL+IPL). However, it appears that diabetes also inflicts additional damage to the outer retinal segment demonstrated by the optical changes of the IS/OS and OS/RPE junction.

Example 6

Assessment of Macular and Intraretinal Thickness Measurements in Eyes of Healthy Volunteers and Subjects with Type 1 Diabetes with No Retinopathy Using Optical Coherence Tomography Purpose:

To assess the thickness measurements of the macula and intraretinal layers in patients with type 1 diabetes mellitus and no retinopathy using optical coherence tomography (OCT); and to compare these findings with those of age-matched healthy volunteers.

Methods:

Standard macular mapping by Stratus OCT was performed in 74 healthy eyes (34±16 yrs, 51 female, 23 male) and 39 eyes with type 1 diabetes mellitus (DM) with no retinopathy (36±10 yrs, 19 female, 20 male) on biomicroscopy. Automatic layer segmentation was performed using a custom-built software for OCT retinal image analysis (OCTRIMA). Mean values of thickness of the macula and RNFL, GCL+IPL, INL, OPL, ONL, IS/OS and OS/RPE junction in healthy volunteers and DM eyes were compared using Mann-Whitney U test. Because of the number of statistical comparisons made in the study, a modified p value of <0.001 was considered statistically significant. Missed significance (MS, 0.001<p<0.05) was also recorded.

Results:

Stratus OCT-measured thickness of the total retina in the central subfield (R1) of DM eyes was higher than those from healthy volunteers (242±23 versus 232±24, $^{\ddagger}$p<0.001). Intraretinal thickness was significantly different between DM and healthy eyes for RNFL, which was thinner in the pericentral regions in DM eyes (R2$^{\ddagger}$, R3$^{\ddagger}$, R4$^{\dagger}$ and R5$^{\dagger}$, $^{\ddagger}$p<0.001 and $^{\dagger}$MS); GCL+IPL complex in R4$^{\dagger}$, R6$^{\dagger}$, R7$^{\dagger}$ and R8$^{\dagger}$, which was also thinner in DM eyes; INL in R2$^{\dagger}$ and R3$^{\dagger}$. (thicker in DM eyes); OPL only in R8$^{\dagger}$ (thicker in DM eyes) and; OS/RPE junction in R1$^{\ddagger}$, R4$^{\ddagger}$, R5$^{\dagger}$, R8$^{\dagger}$ and R9$^{\dagger}$ (thicker in DM eyes). This study also showed no significant differences in macular and intraretinal layer thickness measurements within regions between females and males in the DM group.

Conclusions:

In contrast to previous results reported in the literature for subjects with diabetes but minimal or no retinopathy, our results suggest that macular and intraretinal layer thickness measurements in DM subjects are not similar to thickness measurements obtained from age-matched healthy subjects without diabetes. In addition, the differences of the macular and intraretinal layer thickness measurements between men and women in the DM group were not significant.

Example 7

Comparison of Retinal Thickness by Fourier-Domain Optical Coherence Tomography and OCTRIMA Segmentation Analysis Derived from Stratus OCT Images Purpose:

To compare thickness measurements and segmentation performance between Fourier-domain optical coherence tomography (FD-OCT) image analysis and time-domain OCT images analyzed with a custom-built OCT retinal image analysis software (OCTRIMA).

Materials and Methods

Patients and Methods:

A total of eleven eyes from eleven subjects (9 women and 2 men) were included in this study. Taking into consideration that image quality could be affected by media opacities, elderly subjects were included who had underwent uneventful phacoemulsification surgery with posterior chamber lens (PCL) implantation 6-12 months prior to enrollment. The mean patient age was 70±7 years (range, 65-88 years). The inclusion and exclusion criteria for all participants are listed in Table 3 along with the performed clinical examinations. All subjects were treated in accordance with the tenets of the Declaration of Helsinki. Informed consent was obtained from all participants in this study.

TABLE 3

The inclusion and exclusion criteria for all participants and the performed clinical examinations.

Inculsion criteria

Best-corrected Snellen visual acuity of 20/20
Preoperative spherical and cylindrical correction within ±3.0 diopters (D)
Exclusion criteria The presence of any retinal disease including glaucoma
The presence of systemic diseases except for controlled hypertension
Clinical examinations Best corrected visual acuity (BCVA)
Assessment of intraocular pressure (IOP)
Slit lamp biomicroscopy
Binocular ophthalmoscopy after pupil dilatation Stratus Stratus OCT and RTVue examinations were performed on each eye by the same examiner and with intervals of approximately 10 minutes. For Stratus OCT measurements Macular Thickness Map (MTM) protocol was performed consisting of six evenly spaced radial lines centered on the fovea, each having a 6 mm transverse length. In order to obtain the best image quality focusing, optimization settings and scans were controlled and were accepted only if signal strength was above 6 (preferably 9-10). Scans with foveal decentration (i.e. with center point thickness SD>10%) were repeated. The mean SD percentage of the center point thickness of the accepted scans was 4.96±2.58%. Stratus OCT raw data were exported and analyzed using OCTRIMA. Algorithm performance using OCTRIMA was subjectively evaluated by a human expert to detect algorithm errors. These errors were manually corrected using the manual correction tool provided by OCTRIMA. For RTVue measurements, MM5 and MM6 protocols were performed. MM5 protocol consists of a dense 5×5-mm grid of linear scans around the macula. MM6 protocol consists of 12 evenly spaced radial lines centered on the fovea with a 6 mm transverse length, similar to the Stratus MTM protocol. According to the AIGS Study recommendations, RTVue scans were included with an SSI≥45, having a range between 48.9 and 82.7.

The Stratus OCT system images the outer retinal layers (RPE-photoreceptor complex) as two hyperreflective bands: 1) the photoreceptor inner/outer segment junction and 2) outer segments interdigitising with the microvilli of the RPE (i.e. the OS/RPE junction). The segmentation software of the Stratus OCT system uses the anterior border of the first or innermost hyperreflective band (i.e. photoreceptor inner segment) as the border of the outer retina for calculating the total retinal thickness. OCTRIMA detects the outer retinal boundary as the anterior border of the second hyperreflective band, which is thought to represent the tip of the cone outer segment in the fovea. Thus, OCTRIMA calculates the total RT as the distance between the vitreoretinal interface (ILM) and the anterior boundary of the second hyperreflective band corresponding to the OS/RPE junction. On the other hand, total RT measurements of RTVue are taken between the ILM and the edge defined by the mean value of the maximum reflectance of the second hyperreflective band (i.e. the OS/RPE junction), which defines the outer retinal border below the protoreceptor inner/outer segment junction (information from the manufacturer, Optovue Inc, Fremont, Calif.).

Retinal thickness measured by Stratus OCT, MM5 and MM6 protocols was compared for each of the nine ETDRS subfields with corresponding OCTRIMA results by analysis of variance (ANOVA) followed by Dunnet post-hoc test with comparisons made to OCTRIMA results. The exact location of regions R1-9 is described in detail in Table 4.

TABLE 4

Retinal thickness values in each ETDRS subfield by each software and the differences between the measurements

| | Mean regional thickness | | | | Mean difference of regional thickness | | | |
|---|---|---|---|---|---|---|---|---|
| | OCTRIMA | RTVue MM6 | RTVue MM5 | Stratus | OCTRIMA minus Stratus | OCTRIMA minus RTVue MM6 | OCTRIMA minus RTVue MM5‡ | RTVue MM6 minus Stratus |
| R1 (fovea) | 245 ± 19 | 257 ± 20 | 259 ± 19 | 206 ± 21 | 39 ± 4† | −12 ± 8 | −14 ± 7 | 51 ± 9† |
| R2 (inner superior) | 314 ± 16 | 312 ± 18 | 318 ± 14 | 269 ± 17 | 45 ± 2† | 2 ± 10 | −4 ± 11 | 44 ± 10† |
| R3 (inner nasal) | 316 ± 16 | 312 ± 17 | 321 ± 17 | 274 ± 17 | 42 ± 5† | 4 ± 6 | −5 ± 5 | 38 ± 10† |
| R4 (inner inferior) | 310 ± 20 | 314 ± 12 | 312 ± 20 | 269 ± 24 | 42 ± 5† | −4 ± 10 | −2 ± 4 | 46 ± 14† |
| R5 (inner temporal) | 302 ± 16 | 309 ± 15 | 304 ± 18 | 257 ± 17 | 45 ± 4† | −7 ± 7 | −2 ± 6 | 52 ± 7† |
| R6 (outer superior) | 282 ± 18 | 257 ± 18 | — | 226 ± 21 | 54 ± 8† | 25 ± 9† | — | 29 ± 11† |
| R7 (outer nasal) | 286 ± 14 | 268 ± 14 | — | 243 ± 16 | 42 ± 6† | 18 ± 7* | — | 25 ± 11† |
| R8 (outer inferior) | 260 ± 16 | 265 ± 11 | — | 223 ± 16 | 36 ± 8† | −5 ± 8 | — | 42 ± 12† |
| R9 (outer temporal) | 258 ± 17 | 265 ± 14 | — | 213 ± 17 | 45 ± 4† | −7 ± 6 | — | 52 ± 6† |
| Mean thickness | 286 ± 15 | 284 ± 13 | 303 ± 15 | 242 ± 15 | 43 ± 8† | 2 ± 13 | 48 ± 9 | 42 ± 14† |
| WMT | 279 ± 15 | 274 ± 13 | — | 235 ± 16 | 44 ± 3† | 5 ± 4 | — | 39 ± 6† |

(*p < 0.05, †p < 0.01 by Dunnett post-hoc test).
Data are represented as mean ± SD (Gm).
SD: standard deviation.
‡OCTRIMA and RTVue MM5 average thickness results were not compared because of the different number of regions analyzed.
WMT: weighted mean thickness.

Because of the scan length (5 mm) used in the MM5 protocol only the foveal and pericentral regional (R1-R5) data were used in the analyses. Wilcoxon matched-pairs test was performed to compare the thickness of the GCC measured by RTVue using the MM6 protocol and OCTRIMA with the exclusion of R1 as ganglion cells are not present in the area of the foveal pit. Pearson correlation coefficients were calculated for the above pairwise comparisons. Statistical analyses were performed using Statistica 8.0 Software (Statsoft Inc., Tusla, Okla., USA). The level of significance was set at 5%. Since the sampling is different at each ETDRS region because of different radial spoke patterns used in the scanning protocols of Stratus and RTVue (MM6 protocol), the retinal thickness results measured in the 9 regions were not simply averaged but calculated a weighted mean thickness (WMT). For each eye, WMT was generated, representing an interpolated weighted average. The WMT was calculated using the following equation:

$$WMT = \frac{R1}{36} + \frac{R2 + R3 + R4 + R5}{18} + \frac{(R6 + R7 + R8 + R9) \times 3}{16}$$

Bland Altman plots were constructed to assess agreement in WMT measurements.

Results

A high correlation was observed for RT when comparing OCTRIMA with RTVue MM5 and MM6 protocols (Pearson correlation coefficients range: 0.93-0.97 and 0.82-0.94, respectively). Similarly, a high correlation was obtained for the GCC measurements when comparing OCTRIMA with RTVue MM6 protocol (Pearson correlation coefficients range: 0.73-0.88). Analyses of variance (ANOVA) followed by Dunnett post-hoc test have shown no significant differences in regional thickness measurements between OCTRIMA and RTVue except for ETDRS regions R6 and R7 by the MM6 protocol. The mean difference in RT measurements between OCTRIMA, MM6 and MM5 protocols was less than 7 μm in each ETDRS region except for R1, R6 and R7 (see Table 4). OCTRIMA produced significantly thicker measurements for R6 and R7 (25.00±8.84 μm and 17.64±7.46 μm, mean difference SD, respectively). In the case of the GCC thickness measurements, the mean difference range was from 6.3 to 12.4 μm (see Table 5). GCC measurements were significantly thicker for the MM6 protocol, except for R6 and R7 where MM6 produced thinner results.

TABLE 5

Mean GCC thickness values measured in each ETDRS subfield by OCTRIMA and RTVue MM6 protocol.

|   | OCTRIMA | RTVue MM6 | OCTRIMA minus RTVue MM6 |
| --- | --- | --- | --- |
| R2 | 114 ± 13 | 126 ± 12 | −12 ± 8† |
| R3 | 114 ± 12 | 122 ± 12 | −8 ± 7* |
| R4 | 114 ± 16 | 125 ± 11 | −11 ± 9† |
| R5 | 105 ± 13 | 119 ± 11 | −14 ± 9† |
| R6 | 106 ± 14 | 93 ± 10 | 13 ± 8† |
| R7 | 112 ± 13 | 99 ± 8 | 13 ± 9† |
| R8 | 90 ± 12 | 96 ± 7 | −6 ± 8* |
| R9 | 87 ± 10 | 95 ± 7 | −8 ± 7* |
| WMT | 99 ± 13 | 99 ± 10 | 0 ± 5 |

Data are represented as mean ± SD (μm).
SD: standard deviation.
(* $p < 0.05$, † $p < 0.01$ by Wilcoxon test compared to OCTRIMA measurements)
WMT: weighted mean thickness.

Bland-Altman plots for the difference in weighted mean total retinal thickness between OCTRIMA and RTVue MM6 protocol, average total retinal thickness between OCTRIMA and RTVue MM5 protocol, and for the difference in weighted mean GCC thickness between OCTRIMA and RTVue MM6 protocol, show high correlation of the measurements.

Discussion

Optical coherence tomography has become an integral part of ophthalmic clinical practice and plays an increasing role in the diagnosis and management of retinal diseases. Recent studies have shown that currently available FD-OCT devices are giving significantly higher RT measurements than Stratus OCT due to different assumptions considered for the detection of the outer retinal boundary, making it difficult to compare data obtained by different devices. These differences also make it difficult to adequately evaluate the performance of FD-OCT to detect the progression of disease.

The algorithm of Stratus OCT use the anterior border of the innermost hyperreflective band (i.e. photoreceptor IS) as the border of the outer retina for calculating the total retinal thickness. In contrast, FD-OCT devices image the outer retinal layers (RPEphotoreceptor complex) as three hyperreflective bands: 1) IS/OS junctional complex, 2) outer segments interdigitising with the microvilli of the RPE (i.e. the OS/RPE junction) and 3) RPE cell bodies, although reflections from the choriocapillaries might also be included. This gives rise for a high variability in retinal thickness measurements. In previous studies, the largest difference in total RT measurements in normal subjects compared to Stratus OCT results was found for Spectralis OCT (Heidelberg Engineering, Heidelberg, Germany), as Spectralis calculates the RT between the ILM and the outer border of the RPE layer. The Cirrus OCT (Carl Zeiss Meditec, Inc., Dublin, Calif.) system uses the inner border of the second hyperreflective band as the outer border of the retina. Accordingly, recent studies have found that Cirrus measured the retina 41.9-65 μm thicker than Stratus. SOCT Copernicus (Optopol Technology SA, Zawiercie, Poland), Spectral OCT/SLO (OTI, now a division of OPKO, Miami, Fla.) and RTVue show similar differences (30.9-41.9 μm) in the RT compared to Stratus OCT measurements which can indicate that the outer retinal border detection of these devices is similar.

Total retinal thickness on RTVue images is calculated between the ILM and the edge defined by the mean value of the maximum reflectance of the OS/RPE junction in order to avoid detection errors at the junction's outer border. In this study, RTVue's MM6 protocol was found to measure the retina 42±14 μm thicker compared to Stratus OCT results. These results are comparable to the results obtained by Wolf-Schnurrbusch et al. (*Invest Ophthalmol Vis Sci* 2009). In contrast, Menke et al. (*Ophthalmologica* 2009; 223:352-356) and Huang et al. (*Retina* 2009; 29:980-987) reported a difference of only 14 μm and 8 μm respectively, after comparing Stratus and RTVue measurements. The reason for this difference is unclear.

The software of Topcon 3D OCT-1000 (Topcon Inc., Tokyo, Japan) allows users to set their thickness measurements from the ILM to RPE layer, as defined in the traditional histopathology, or measure the thickness from the ILM to the inner border of the IS/OS photoreceptor junction, for consistency with the legacy time domain system. However, no information is provided about which boundary of the RPE layer (i.e. inner or outer) is detected.

On the contrary, OCTRIMA measures RT as the distance between the ILM and the inner boundary of the OS/RPE junction defined as "true retinal thickness". The data herein show a 43±8 μm mean difference between RT values measured by OCTRIMA derived from Stratus OCT images which is very similar to the mean difference between RTVue and Stratus OCT. Bland-Altman plots showed that WMT measured by OCTRIMA is on average 5 μm higher than that measured by RTVue using the MM6 protocol and is on average 5 μm lower than that measured by RTVue using the MM5 protocol which both are below the axial resolution of the devices. The explanation for the comparable differences might be that the location of the mean value of the maximum reflectance of the second hyperreflective band calculated by RTVue and used to define the outer border of the retina is closely located to the actual inner border of the second hyperreflective band (i.e. the OS/RPE junction). Thus, the small differences between the two measurement methods of RTVue and OCTRIMA are hardly distinguishable. A high correspondence for the RT measurements was obtained, herein, when these measurements were compared between OCTRIMA and RTVue using MM5 and MM6 protocols. The observed good correlation emphasizes the capability of comparable retinal measurements by Fourier-domain OCT and Stratus OCT-derived segmentation using the OCTRIMA software.

It should be noted that RT measurements obtained in R1 by the MM5 and MM6 protocols of RTVue were approximately 12-14 µm higher than measurements obtained with OCTRIMA, however not reaching a statistical difference. The reason for this difference is not clear as Stratus OCT scans were carefully centered, the mean SD % of the center point thickness of the accepted scans was 4.96±2.58%, therefore the difference is unlikely to have been caused by decentration artifact. Moreover, the OCTRIMA algorithm used in this study is optimized for Stratus OCT images and segmentation errors were manually corrected by an experienced operator. Theoretically, FD-OCT should produce fewer segmentation failures because of higher resolution. Although RTVue allows manual correction of the automated segmentation, the manual adjustment was not used to change the segmentation results, while differences in axial resolution and calibration might also contribute to thickness measurement differences.

Besides, mean retinal thickness values were generated with different scan protocols with the sampling density being higher in the outer ETDRS areas by the RTVue MM6 protocol (12 radial scans) compared to Stratus OCT (6 radial scans) which might also contribute to the difference between the thickness measurements in R1. In the outer superior and outer nasal subfields (i.e. R6 and R7), the RTVue results obtained with the MM6 protocol produced significantly thinner results than OCTRIMA, by approximately 18-25 µm. A possible explanation for the above differences could be related to incorrect boundary detection, however OCTRIMA segmentation errors were manually corrected by an experienced operator. Particularly, minor errors in the segmentation of the outer border of the retina were observed at the periphery in some RTVue scans. Taking into consideration the known anatomical properties of the regions in the peripheral ring (the nasal macula being thicker than the temporal) it was supposed that thickness values measured by the RTVue device should have been higher in subfields 6 and 7. Thus, it was inferred that RTVue's thinner measurements in R6 and R7 were possibly due to the low quality observed in some OCT scans, which could be a direct result of image acquisition pitfalls leading to segmentation errors.

In this study, RTVue peripheral regions R6-R9 (using the MM6 protocol) had all comparable thickness values as opposed to Stratus OCT data being distributed as described above. Similar results were found by Huang et al. when comparing regional thickness measurements between Stratus OCT and RTVue OCT. They found that RTVue produced significantly higher RT measurements in each ETDRS region except for the outer inferior region (R8) where the difference was not significant and the outer nasal region (R7) where Stratus OCT produced thicker measurements than RTVue, however, no explanation was found for these differences.

It is also of great interest that the software of the RTVue device enables the segmentation of the ganglion cell complex (GCC) in the macula by detecting the IPL outer boundary, which might facilitate a more rigorous glaucoma analysis. (Tan O, et al. IONS 2007; 48:ARVO E Abstract 512). Certainly, OCTRIMA is also able to extract the GCC, therefore the potentialities of the two algorithms were compared. A good correspondence between OCTRIMA and RTVue MM6 protocol was found, however, thickness values measured by the RTVue device were 6-10 µm higher in all but two regions. Interestingly, GCC in subfields R6 and R7 was approximately 12 µm thinner by the RTVue using the MM6 protocol than by OCTRIMA measurements, similarly to total retinal thickness values. This difference was less than that observed for the total RT, therefore it was assumed it was not an isolated GCC or outer retinal boundary detection error. Although the above difference in GCC measurements is relatively small, it could be of great importance in clinical settings as for example in glaucoma diagnostics. The small average difference of 1 µm shown by the Bland-Altman plot might be due to the results in R6, R7 influencing the calculation of the mean.

In summary, it was found that measurements with the Stratus OCT showed the lowest RT values, whereas measurements with the RTVue OCT and Stratus OCT-derived images assessed by OCTRIMA yielded the highest ones. These discrepancies were based on differences in retinal segmentation algorithms. In addition, a high correspondence of RT measurements between Fourier-Domain OCT and Stratus OCT-derived images assessed by OCTRIMA was demonstrated. Despite the worse resolution of TD-OCT we could achieve a high correspondence of retinal layer segmentation with FD-OCT in elderly subjects who are supposed to have bad fixation cooperation. Weighted mean total retinal thickness data were shown to have high correlation, while regional differences might still exist. The measurements of the GCC should also be compared with care as there is a marked difference between OCTRIMA and RTVue using the MM6 protocol. These differences were most probably based on differences in retinal segmentation algorithms, sampling, calibration and axial resolution.

An agreement between ophthalmologists and developers is needed in order to standardize OCT RT measurements, however, the use of custom-built segmentation software along with open-source image files enabling their easy access could also facilitate the transformation of data obtained by different devices. In view of the higher price of FD-OCT systems and the widespread use of TD-OCT worldwide, we believe our OCTRIMA software can be of substantial value in future studies of macular pathophysiology and it might also perform well for FD-OCT images in the future.

Example 8

Reliability and Reproducibility of Macular Segmentation Using a Custom-Built Optical Coherence Tomography Retinal Image Analysis Software Methods (Analysis Per Scan: Uninterpolated Data)
Subjects:
Ten undilated eyes of five healthy subjects ranging in age from 25 to 34 yr (mean age 29 yr), were involved in this study. Inclusion criteria included best-corrected visual acuity of 20/25 or better, no history of any current ocular or systematic disease, and a normal appearing macula on contact lens biomicroscopy. All subjects underwent visual acuity testing with refraction and a complete slit-lamp examination. All subjects were treated in accordance with the tenets of the Declaration of Helsinki.
OCT Measurements:
For imaging purposes the commercially available Stratus OCT unit (software version 4.0; Carl Zeiss Meditec, Inc., Dublin, Calif.) was used. Subjects underwent three OCT scanning sessions during the first visit on day (D1) by two experienced examiners (E1, E2) with intervals of approximately 5 min between scans (sessions 1 and 2, corresponding to S1 and S2, respectively). Thus, two scans (E1D1S1, E1D1S2) were performed by the same examiner (E1) to determine intraobserver repeatability (i.e., E1D1S1 versus E1D1S2). A third scan was performed by a second examiner (E2) and the results were compared with those of the first scan (S1) to determine interobserver reproducibility (i.e., E1D1S1 versus E2D1S1). To assess inter-visit reproducibility (i.e., E1D1S1 versus E1D2S1), an additional scan session was performed by one of the examiners (E1) during a second visit (D2) the next day. Between the examiners, the OCT instrument alignment and controls were randomly changed, so all alignment and focusing had to be restarted. Only scans with a signal strength of 6 or more were accepted.

The Radial Lines protocol was used for the OCT studies. This protocol acquires six retinal B-scans each of scan length 6 mm, each scan oriented 30 deg apart from each other, and centered at the fovea. Each B-scan consists of 512 aligned A-scans. Each A-scan consists of 1024 pixels with a total scan depth of 2 mm in tissue. Thus, each B-scan acquired in this protocol consists of a total 1024×512 pixels. If the subject moved or blinked during the scan, the image was repeated. In addition, the quality of B-scans was evaluated with OCT-RIMA. Generally, the standard deviation of the foveal center point thickness is used as a measure of the scan variance. A high standard deviation (>10% of center point thickness) indicates high variability, usually due to patient movement or boundary line error, and therefore incorrect center point thickness. Good quality images have a standard deviation <10% of center point, good clarity of the layers, and are also well centered. Substantially decentered scans could have a low standard deviation. Therefore, a scan quality factor (SQF) based on the standard deviation calculation (in percent) of the foveal center point (FCP) for the six radial line scans included in the OCTRIMA software was used to control the variability of measurements associated to image acquisition pitfalls. A good scan has an SQF=1, indicating that the percentage standard deviation of the foveal center point is ≤10. Data for each measurement were exported to disk using the export feature available in the Stratus OCT version 4.0 analysis software.

Computer-Aided OCT Image Analysis Software:

OCTRIMA is a powerful computer-aided system designed to facilitate viewing and automatic/semiautomatic OCT retinal image analysis. The application essentially provides dual functionality in a single software package by combining image enhancement and speckle denoising of Stratus OCT images along with intraretinal segmentation and error correction using direct visual evaluation of the detected boundaries. Moreover, the software has the capability to provide quantitative analysis based on measured values of corrected thickness, volume, and reflectance of the various cellular layers of the retina. A total of seven intraretinal layers can be extracted using OCTRIMA, namely, the retinal nerve fiber layer (RNFL), the ganglion cell layer along with the inner plexiform layer (GCL+IPL), the inner nuclear layer (INL), the outer plexiform layer (OPL), the outer nuclear layer (ONL), the photoreceptor inner/outer segment (IS/OS) junction, and the outer segment/retinal pigment epithelium (OS/RPE) junction.

Quantitative Analysis:

As a result of repeatedly scanning a total of 10 healthy eyes during four sessions on two consecutive days by two OCT examiners, a total of 240 OCT B-scans were collected and analyzed by an experienced grader. Specifically, the grader segmented all the B-scans from all sessions (E1D1S1, E1D1S2, E2D1S1, and E1D2S1) using OCTRIMA for testing the intraobserver, interobserver, and intervisit variability of repeated measurements performed by the same examiner, by different examiners, and at different visits.

After each B-scan was denoised, the inner and outer borders of the retinal structure were identified between the internal limiting membrane (ILM) and the inner boundary of the OS/RPE junction; and a total of seven intraretinal layers were extracted using OCTRIMA. Note that visualizing and quantifying microstructural changes within the photoreceptor and RPE, layers is difficult using Stratus OCT images due to weakened signal energy after penetrating the neuroretina, RPE, and choriocapillaries. Thus, the three outermost hyperreflective layers clearly observed with Fourier domain OCT systems are not certainly visible in Stratus OCT images. Only two hyperreflective layers and one hyporeflective band are observed with the Stratus OCT device. These layers have been identified as the IS/OS junctional complex, which is the first hyperreflective layer, the hyporeflective band below this junction, which is clearly wider in the fovea and attributed to the photoreceptor OSs, and the second hyperreflective layer corresponding to the outer segments interdigitizing with the microvilli of the RPE (i.e., the OS/RPE junction). In time domain OCT images, the RPE and photoreceptor OSs are too close to be resolved and often appeared as a single hyperreflective band. Thus, the second and third hyperreflective layers have been conventionally assigned to the RPE in previous studies using Stratus OCT images. However, the third hyperreflective layer only visible in SDOCT images and identified as the RPE, is probably due to a signal from the RPE cell bodies, although reflections from choriocapillaries might also be included. Accordingly, OCTRIMA measurements of the total retinal thickness were made from the innermost point of the retina (ILM) to the inner border of the second hyperreflective band, which has been attributed to the OS/RPE junction in agreement with histological studies. Note that this thickness differs from the thickness measured with Stratus OCT, which calculates the distance between the inner border (ILM) of the retina and the inner border of the highly reflective photoreceptor IS/OS junction (i.e., the first hyperreflective band). Therefore, in contrast to OCTRIMA, thickness calculated with the Stratus OCT algorithm does not take into account the thickness of the junctions of the inner/outer photoreceptor segment and the outer photoreceptor segments (i.e., the hyporeflective band) in the fovea.

All scans in the study had a signal strength of 9 or 10 and were perfectly centered (SQF=1). Algorithm performance was visually evaluated by the experienced grader to detect algorithm errors. Criteria for algorithm error included evident disruption of the detected boundary (e.g., small peaks, linear and curve offsets), and/or detected boundary jumping to and from different anatomical structures. The average number of manual corrections needed per scan was three. Since the thickness of the inner and outer photoreceptor segments has been found to be relatively constant, which is consistent with an anatomically uniform thickness, the outer border of the photoreceptor segment junction (IS/OS) can be extracted manually using the semiautomated approach in OCTRIMA. Thus, the outer border of the IS/OS is located 10 pixels from the outer border of the ONL, which gives a constant thickness of 20 μm. Accordingly, the thickness measurements for the IS/OS were not included in this study. Thus, the thickness measurements of the total retina and six intraretinal layers (RNFL, GCL+IPL, INL, OPL, ONL, and OS/RPE junction) were actually used in the analysis. Note that the repeatability and reproducibility analysis was performed for the uninterpolated measurements at every A-scan location for all six B-scans (i.e., uninterpolated raw data).

Statistical Methods: The coefficients of repeatability and reproducibility were calculated along with the intraclass correlation coefficients (ICCs) with the methods outlined by Bland and Altman for each of the uninterpolated averaged thickness measurements obtained for the total retina and intraretinal layer (British Standards Institution, "Accuracy (trueness and precision) of measurement methods and results: basic methods for the determination of repeatability and reproducibility of a standard measurement method," BS ISO 5725 part 2, British Standards Institution, London (1994); J. M. Bland and D. G. Altman, "Statistical methods for assessing agreement between two methods of clinical measurement," Lancet 1, 307-310 (1986)). The coefficients of repeatability and reproducibility were computed from the standard deviations (SDs) of the differences between measurements made at each session. The Wilcoxon signed rank test (5% significance level) was performed to determine any statistically significant difference between the measurements obtained by different examiners or during different visits. The ICC was calculated on the basis of a two-way mixed model for analysis of variance (ANOVA) as proposed by Bartko and Carpenter (J. Nerv. Ment. Dis. 163, 307-317 (1976)). The statistical analysis was performed using the software package SPSS version 16 (SPSS Inc., Chicago, Ill.).

Results:

Retinal thickness measurements at every A-scan location for all six B-scans of all 10 eyes was performed for the total retina and six intraretinal layers. As a result, the average thickness per layer was calculated using the OCTRIMA software for each macular scan group of all 10 eyes for each session. Coefficients of repeatability and reproducibility for the total retina and six intraretinal layers are given in Table 6.

TABLE 6

Thickness measurements (mean ± SDs), coefficients of repeatability/reproducibility (CRs), ICCs, and Wilcoxon test results obtained for the total retina and six intraretinal layers.

| | Mean ± SD (µm) | CR (µm) | CR (%) | ICC | ρ Value |
|---|---|---|---|---|---|
| Measures of Repeatability (Intraobserver Test) | | | | | |
| RNFL | 40.66 ± 1.74 | 1.88 | 4.62 | 0.86 | 0.65 |
| GCL + IPL | 73.45 ± 7.73 | 3.41 | 4.64 | 0.98 | 0.39 |
| INL | 34.13 ± 1.12 | 2.10 | 6.15 | 0.63 | 0.17 |
| OPL | 32.53 ± 0.63 | 1.66 | 5.11 | 0.37 | 0.07 |
| ONL | 88.30 ± 4.92 | 2.91 | 3.29 | 0.96 | 0.24 |
| OS/RPE | 12.72 ± 1.38 | 1.25 | 9.80 | 0.90 | 0.39 |
| Total Retina | 282.23 ± 13.36 | 8.62 | 3.06 | 0.94 | 0.24 |
| Measures of Reproducibility (Interobserver Test) | | | | | |
| RNFL | 40.87 ± 2.11 | 1.88 | 4.61 | 0.90 | 0.33 |
| GCL + IPL | 72.89 ± 8.30 | 4.54 | 6.23 | 0.96 | 0.09 |
| INL | 34.29 ± 1.07 | 1.81 | 5.29 | 0.69 | 0.05 |
| OPL | 32.44 ± 0.78 | 1.68 | 5.18 | 0.54 | 0.17 |
| ONL | 88.11 ± 5.16 | 5.33 | 6.05 | 0.87 | 0.45 |
| OS/RPE | 12.85 ± 1.30 | 3.94 | 30.69 | 0.25 | 0.96 |
| Total Retina | 281.33 ± 15.66 | 12.83 | 4.57 | 0.63 | 0.72 |
| Measures of Reproducibility (Intervisit Test) | | | | | |
| RNFL | 40.91 ± 1.84 | 2.54 | 6.20 | 0.78 | 0.45 |
| GCL + IPL | 73.67 ± 7.66 | 2.22 | 3.02 | 0.99 | 0.96 |
| INL | 34.03 ± 1.12 | 1.61 | 4.72 | 0.76 | 0.39 |
| OPL | 32.45 ± 0.67 | 1.49 | 4.59 | 0.51 | 0.09 |
| ONL | 88.35 ± 4.81 | 3.21 | 3.63 | 0.94 | 0.58 |
| OS/RPE | 12.76 ± 1.46 | 2.00 | 15.68 | 0.78 | 0.58 |
| Total Retina | 281.94 ± 13.58 | 6.69 | 2.38 | 0.97 | 0.29 |

The means and SDs of the differences between measurements obtained under different conditions, ICCs, and Wilcoxon test results are also shown in Table 6. Repeatability coefficients to test intraobserver variability were less than 4% for the total retina and less than 7% for all intraretinal layers except the OS/RPE junction (~10%). Reproducibility coefficients to test interobserver variability were less than 5% for the total retina and less than 7% for all intraretinal layers except the OS/RPE junction (~31%); and for intervisit variability it was less than 3% for the total retina and less than 7% for all intraretinal layers except the OS/RPE junction (~16%) (see Table 6). The ICCs obtained for the intraobserver and intervisit variability tests were greater than 0.75 for the total retina and all intraretinal layers, except INL (intraobserver and interobserver test) and OPL (intraobserver, interobserver, and intervisit test). The lowest ICC values for the total retina were obtained for the interobserver variability test (see Table 6). In addition, the Wilcoxon paired measurements test (5% significance level) showed that there were no statistically significant differences between measurements obtained by different examiners or during different visits.

Discussion:

Although a layer-editing tool to manually adjust the retinal layer boundaries for macula and RNFL was recently incorporated in the current Stratus OCT software, its quantitative analysis does not provide thickness measurements of the various intraretinal layers. This limitation in the Stratus OCT system has stimulated interest in developing segmentation algorithms to better detect the local changes in the retinal structure to improve retinal disease detection and its progression.

In this study, the reliability and reproducibility of macular segmentation mapping is reported using the OCTRIMA software, which overcomes the limitation of the Stratus OCT software and provides additional quantitative information that can be extracted from OCT data. The uninterpolated average thickness measurements recorded for all 10 healthy eyes showed that the coefficient of repeatability was less than 4% for the total retina and less than 7% for intraretinal layers except the OS/RPE junction (~10%). These values indicate high repeatability of the results of measurements generated by the OCTRIMA software (see Table 6). The high variability in the thickness measurements of the OS/RPE junction is due to the fact that the outer boundary of this layer is not clearly visualized in Stratus OCT images because of the low contrast between the OS/RPE junction (outer border) and the RPE inner boundary, which can be attributed to the limitation of the Stratus OCT system to penetrate deeper structures in the retina. Moreover, the interobserver coefficients of reproducibility calculated for the total retina and intraretinal layers (except for the RNFL) were higher than corresponding values for intervisit reproducibility, which may possibly be explained by the fact that subject fatigue and normal drying of the eye during repeated sessions the same day induced more noise into the overall measurements.

In addition the scans were not aligned between visits because the Stratus OCT did not provide this feature. Thus, this limitation affected the intervisit variability results. Furthermore, there was less than 5% interobserver variability for the total retinal thickness measurements (see Table 6). This is a reassuring finding for an analysis software tool applied to data obtained with a diagnostic instrument, because comparisons of measurements taken for the same subject over a period of time may be compared even when measurements are obtained by different experienced examiners. In summary, intraobserver, interobserver, and intervisit variability combined accounted for less than 5% of total variability for the total retinal thickness measurements and less than 7% for the intraretinal layers except the OS/RPE junction.

Conclusions:

It was ascertained that retinal thickness measurements for the total retina and intraretinal layers (except the OS/RPE junction) performed using OCTRIMA are very repeatable and reproducible. High measurement repeatability and reproducibility is a prerequisite for quantitative application of OCTRIMA in research and clinical work. These findings are particularly useful because they indicate that any retinal thickness change of greater than 5% (or layer average thickness change greater than 7%) in the macular area in healthy undilated subjects are likely to be caused by changes in retinal thickness rather than by inconsistencies in either the OCTRIMA software or in measurements given by the OCT system.

Although the OCTRIMA quantitative analysis of Stratus OCT images described in this paper is potentially useful, new OCT technologies, such as spectral domain, ultrahigh resolution, and adaptive-optics-based OCT technology, are likely to partially afford better solutions to the limitation of existing OCT software by providing images with higher resolution along with a dense map of the retina with precise registration and localization. However, automatic segmentation algorithms for OCT data have a tendency to give erroneous segmentation results especially in pathological cases, which is actually a result of the algorithm performance independently of how well the OCT image could be reproduced with a high level of detail. Consequently, to improve the practicability of OCT technology in ophthalmology, effective data processing requires robust and accurate segmentation algorithms integrated into intelligent software solutions. In addition, computer-aided detection and diagnosis based on automatic/semiautomatic robust algorithms will be essential in clinical studies where large data sets will be impractical for manual grading approaches.

Even though the results presented are based on Stratus OCT images, the main purpose was to establish the feasibility of the quantitative methodology or OCT image analysis independent of the technology used. There is no doubt that if this methodology works well for Stratus OCT images, then it should perform better for SDOCT images which have better resolution. As a matter of fact, OCTRIMA is currently able to analyze B-scans from SDOCT systems. However, a more practical interface to handle the large quantities of measured raw data generated by these systems along with the associated substantial processing is required, and it is currently under development.

In addition, recent studies have shown that retinal thickness measurements between SDOCT devices are significantly different due to different assumptions considered for the detection of the outer retinal boundary, which makes it difficult to compare data obtained by different devices. These differences also make it difficult to adequately evaluate the performance of SDOCT to detect the progression of disease. OCTRIMA could facilitate a well-defined and standardized quantitative analysis for the assessment of retinal diseases and its progression using SDOCT images. Thus, quantitative evaluation of OCT images with OCTRIMA may improve the quality of data and analysis currently being obtained with Stratus OCT and SDOCT devices. From a clinical point of view, it would be possible to understand the mechanism and time-dependence of macular dystrophies and degenerations, and neurodegenerative diseases by understanding the cellular changes of the macula by using the OCTRIMA software. OCTRIMA can be used as an in vivo tool for quantification of the early structural changes in retinal diseases.

Direct comparison of this study with previous reproducibility and repeatability studies is difficult because the age group of healthy subjects along with image segmentation and experimental and statistical methods vary between studies. As with previous findings, change of examiner did not significantly affect the reproducibility of the measurements in healthy eyes. Future studies will examine the repeatability and reproducibility of macular segmentation mapping with OCTRIMA for each of the nine Early Treatment of Diabetic Retinopathy Study (ETDRS)-like regions in healthy subjects and patients with early diabetic retinopathy and other retinal diseases.

Example 9

Assessing the Regional Reliability and Reproducibility of Intraretinal Layer Segmentation with a Custom-Built OCT Retinal Image Analysis Software This study investigated the reliability and reproducibility of the OCTRIMA software for each of the 9 ETDRS-like regions (i.e. interpolated measurements) using Stratus OCT data from normal healthy eyes.

Methods

Subjects:

A total of ten undilated eyes of five healthy subjects were involved in this study, ranging in age from 25 to 34 yr (mean age 29 yr). All subjects underwent visual acuity testing with refraction and a complete slit-lamp examination. Inclusion criteria included best-corrected visual acuity of 20/25 or better, no history of any current ocular or systematic disease, and a normal appearing macula on contact lens biomicroscopy. All subjects were treated in accordance with the tenets of the Declaration of Helsinki.

OCT Measurements:

The Stratus OCT unit (software version 4.0; Carl Zeiss Meditec, Inc., Dublin, Calif.) was used to obtain the OCT images from all the subjects. Only scans with a signal strength of six or more were accepted. Subjects underwent three OCT scanning sessions during the first visit on day (D1) by two experienced examiners (E1, E2) with intervals of approximately five minutes between scans (Session 1 and 2, corresponding to S1 and S2, respectively). Thus, two scans (E1D1S1, E1D1S2) were performed by the same examiner (E1) to determine intraobserver repeatability (i.e., E1D1S1 versus E1D1S2). A third scan was performed by a second examiner (E2) and the results were compared with those of the first scan (S1) to determine interobserver reproducibility (i.e. E1D1S1 versus E2D1S1). To assess intervisit reproducibility (i.e., E1D1S1 versus E1D2S1), an additional scan session was performed by one of the examiners (E1) during a second visit (D2) the next day. Between the examiners, the OCT instrument alignment and controls were randomly changed, so all alignment and focusing had to be restarted.

The radial lines protocol was used for the OCT studies. This protocol acquires six retinal B-scans each of scan length 6 mm, each scan oriented 30 deg apart from each other, and centered at the fovea. Each B-scan consists of 512 aligned A-scans. Each A-scan consists of 1024 pixels with a total scan depth of 2 mm in tissue. Thus each B-scan acquired in this protocol consists of a total 1024×512 pixels. If the subject moved or blinked during the scan, the image was repeated. In addition, the quality of B-scans was evaluated with OCTRIMA. Specifically, a scan quality factor (SQF) based on the standard deviation calculation (in %) of the foveal center point (FCP) for the six radial line scans included in the OCTRIMA software was used to control the variability of measurements associated to image acquisition pitfalls. A good scan has a SQF=1, indicating that the percentage standard deviation of the foveal center point is ≤10. Data for each measurement were exported to disk using the export feature available in the Stratus OCT version 4.0 analysis software.

Computer-Aided OCT Image Analysis Software:

OCTRIMA is a powerful computer-aided system designed to facilitate viewing and automatic/semiautomatic OCT retinal image analysis. The application essentially provides dual functionality in a single software package by combining image enhancement and speckle denoising of Stratus OCT images along with intraretinal segmentation and error correction using direct visual evaluation of the detected boundaries. Moreover, the software has the capability to provide quantitative analysis based on measured values of corrected thickness, volume, and reflectance of the various cellular layers of the retina. A total of seven intraretinal layers can be extracted using OCTRIMA, namely, the retinal nerve fiber layer (RNFL), the ganglion cell layer along with the inner plexiform layer (GCL+IPL), the inner nuclear layer (INL), the outer plexiform layer (OPL), the outer nuclear layer (ONL), the photoreceptor inner/outer segment (IS/OS) junction; and the outer segment/retinal pigment epithelium (OS/RPE) junction.

Quantitative Analysis:

A total of 240 OCT B-scans were collected and analyzed by an experienced grader after two OCT examiners repeatedly scanned a total of ten healthy eyes during four sessions in two consecutive days. Specifically, the grader segmented all the B-scans from all sessions (E1D1S1, E1D1S2, E2D1S1, and E1D2S1) using OCTRIMA for testing the intraobserver, interobserver, and intervisit variability of repeated measurements performed by the same examiner, by different examiners, and at different visits.

Once each B-scan was denoised, the inner and outer borders of the retinal structure were identified between the ILM and the inner boundary of the OS/RPE junction. A total of seven intraretinal layers were extracted using OCTRIMA. It is well known that it is difficult to visualize and quantify changes within the photoreceptor and RPE layers using Stratus OCT images because of these layers are too close to be resolved and often appear as a single hyperreflective band in TD-OCT images. Accordingly, OCTRIMA measurements of the total retinal thickness were made from the innermost point of the retina known as the inner limiting membrane (ILM) to the inner border of the second hyperreflective band, which has been attributed to the OS/RPE junction in agreement with histological studies. It was noted that Stratus OCT calculates the total retinal thickness between the inner border (ILM) of the retina and the inner border of the highly reflective photoreceptor IS/OS junction (i.e., the first hyperreflective band). Therefore, in contrast to OCTRIMA, thickness calculated with the Stratus OCT algorithm does not take into account the thickness of the junctions of the inner/outer photoreceptor segment and the outer photoreceptor segment (i.e. the hyporeflective band) in the fovea.

All scans in the study had a signal strength of 9 or 10. Algorithm performance was visually evaluated by experienced graders to detect algorithm errors. Criteria for algorithm error included evident disruption of the detected boundary (e.g. small peaks, linear and curve offsets), and/or detected boundary jumping to and from different anatomical structures (i.e. false segmentation). The average number of manual corrections needed per scan was three. Since the thickness of the inner and outer photoreceptor segments has been found to be relatively constant, which is consistent with an anatomically uniform thickness, the outer border of the photoreceptor segment junction (IS/OS) can be extracted manually using the semi-automated approach in OCTRIMA. Thus, the outer border of the IS/OS is located 10 pixels from the outer border of the ONL, which give a constant thickness of 20 $\mu$m. Accordingly, the thickness measurements for the IS/OS were not included in this study. As a result, the thickness measurements of the total retina and six intraretinal layers (RNFL, GCL+IPL, INL, OPL, ONL, and OS/RPE junction) were actually used in the analysis.

In addition, OCTRIMA is capable of generating topographic maps for macular thickness similar to the standards set by the Early Treatment Diabetic Retinopathy Study (ETDRS). An OCTRIMA macular map is divided into nine zones that correspond to the ETDRS regions: fovea within a diameter of 1 mm centered on the foveola; pericentral ring, the circular band from the central 1 mm to 3 mm, divided into four quadrants i.e. superior, inferior, temporal, and nasal; and peripheral ring from 3 mm up to 6 mm, divided into the same quadrants. As in the current Stratus OCT software, it was noted that the OCTRIMA software maps the macula using 6 radial lines centered on fixation. This pattern has higher sampling density in the fovea, which does not contain the following intraretinal layers: RNFL, GCL, IPL, INL, and OPL. Since these particular layers are not present in the foveal region, OCTRIMA uses a predefined control in a 1.5 diameter zone in the fovea. Specifically, the control forces the inner and outer side of the GCL+IPL complex, and the outer side of the INL, and OPL to be coincident in this region.

The repeatability and reproducibility analysis was performed for each of the 9 ETDRS-like regions (R1-R9). The macular regions were defined as R1 fovea, R2 superior inner, R3 nasal inner, R4 inferior inner, R5 temporal inner, R6 superior outer, R7 nasal outer, R8 inferior outer, R9 temporal outer. The central R1 region has a diameter of 1 mm, regions R2 to R5 are zones of a circle 3 mm in diameter, and regions R6 to R9 are zones of a circle 6 mm in diameter.

Statistical Methods:

The coefficients of repeatability and reproducibility were calculated along with the intraclass correlation coefficients (ICCs) with the methods outlined by Bland and Altman for each of the averaged thickness measurements obtained for the total retina and intraretinal layers. The coefficients of repeatability and reproducibility were computed from the standard deviations (SDs) of the differences between measurements made at each session. The Wilcoxon signed rank test (5% significance level) was performed to determine any statistically significant difference between the measurements obtained by different examiners or during different visits. The ICC was calculated on the basis of a two-way mixed model for analysis of variance (ANOVA) as proposed by Bartko and Carpenter (*J Nerv Ment Dis* 1976; 163:307-317). The statistical analysis was performed using the software package SPSS version 16 (SPSS Inc, Chicago, Ill.).

Results

The average thickness calculated using the OCTRIMA software for each of the 9 ETDRS regions of all 10 eyes for each scanning session is given in Table 7. The same grader (G1) analyzed the scans from all sessions. The repeatability and reproducibility results are shown in Table 8. The coefficient of repeatability (intraobserver variability) was less than 5% for the total retina, less than 17% for the RNFL in the pericentral (R2-R5) and peripheral (R6-R9) regions respectively (except in temporal regions R5 and R9); less than 9% and 21% for the GCL+IPL complex in the pericentral and peripheral regions respectively; less than 14% and 23% for the INL in the pericentral and peripheral regions respectively; and less than 12% and 22% for the OPL in the pericentral and peripheral regions respectively. It was also less than 7% and 6% for the ONL in the pericentral and peripheral regions respectively (see Table 8, upper section). The coefficient of reproducibility (interobserver variability) was less than 7% for the total retina; less than 20% for the RNFL in the pericentral and peripheral regions (except in the temporal regions R5 and R9); less than 11% for the GCL+IPL complex in the pericentral regions and at worst it was 22% (i.e., in R8). It was also less than 15% in the pericentral regions for the INL, OPL, and ONL; less than 15% in the peripheral regions for the ONL; and at worst it was 23-30% (i.e., in R7) for the INL and OPL (see Table 8, middle section). The coefficient of reproducibility (intervisit variability) was less than 5% for the total retina; less than 13% for the RNFL except in R4-R5 and R8-R9, less than 9% for the GCL+IPL complex in the pericentral regions and at worst it was 16% (i.e., in R8). It was also less than 15% (18%) and 17% (20%) for the INL (OPL) in the pericentral and peripheral regions respectively; and less than 8% for the ONL (see Table 8, lower section). The coefficients of repeatability and reproducibility for the intraobserver, interobserver, and intervisit variability tests for the OS/RPE junction oscillated between 17% and 63%.

The ICCs obtained for the intraobserver and intervisit variability tests were greater than 80% for the total retina, GCL+IPL, and ONL. The lowest ICC values were obtained for the interobserver variability test (see Table 9). The ICCs were also greater than 70% for the RNFL in R3, R4, R6, and R7 (intraobserver and interobserver variability test) and greater than 80% in R6 and R7 (intervisit variability test). The highest ICC values (>70%) for the OPL were obtained in R4, R5, and R7 (intraobserver variability test). The highest ICCs values (>70%) for the INL were obtained in R3 (interobserver and intervisit variability test) and R4 (intervisit variability test). The ICCs were also greater than 70% for the OS/RPE junction in R1, R3 (intraobserver variability test) and R4 (intraobserver and intervisit variability test). The Wilcoxon paired measurements test showed that there were no statistically significant differences between measurements obtained by different examiners or during different visits.

Discussion

The current Stratus OCT software provides a map of the macula and nerve fiber layer thickness along with regional averages, but it does not provide thickness measurements of the separate retinal layers. This limitation in the Stratus OCT system has stimulated interest in developing segmentation algorithms to better detect the local changes in the retinal structure to improve retinal disease detection and its progression. In this study, the regional reliability and reproducibility of macular segmentation mapping is reported using OCTRIMA. The OCTRIMA software overcomes the limitations of the Stratus OCT software and provides additional quantitative information that can be extracted from OCT data. An important aspect of any test's ability to detect change is the reproducibility and reliability of the measurements, which was investigated in this study. The OCTRIMA software provides both uninterpolated average thickness and regional thickness result data, which are useful measurements both in clinical studies and practice.

Regional reproducibility results for the RNFL showed the nasal regions (R3 and R7) to be the most reproducible (highest ICCs), whereas the temporal regions (R5 and R9) to be the least reproducible (see Table 9), with fairly good reproducibility in the superior and inferior regions. The reason for this is that—according to this study's observations and supported by histological data—the RNFL layer is often undetectable at the temporal part of the macula. In addition, the ICC value for the superior and inferior regions was smaller than the value for the nasal region. This is due to the smaller mean RNFL thickness values in the superior and inferior regions relative to the nasal part of the macula. The regional reproducibility results for the GCL+IPL complex showed the pericentral regions (R2-R5) to be more reproducible than the peripheral regions (R6-R9). It is possible that some of the variability encountered in the peripheral regions may be attributed to the fact that the number of measured points significantly decreases from the center to the periphery, where the tomograms are more spaced. The ICCs were particularly low for the INL and OPL, indicating that the combination of these layers could be a good alternative to minimize the variability of detected borders between them. The reproducibility results for the OS/RPE junction in all macular regions were the least reproducible with a relatively low ICC due to the low contrast between the OS/RPE junction (outer border) and the RPE inner boundary, which can be attributed to the limitation of the Stratus OCT system to penetrate deeper structures in the retina. The ICCs were particularly high for all 3 groups of comparisons for the total retina; GCL+IPL complex and the ONL (see Table 9).

The regional thickness measurements for the total retina showed that coefficients of repeatability ranged from 3 to 5% in healthy eyes, and coefficients of reproducibility ranged from 3 to 6% (interobserver variability) and 1 to 4% (intervisit variability). The enhanced repeatability and reproducibility coefficients observed here, are likely due to the robustness of OCTRIMA's segmentation algorithm. The improved ICCs of 85% to 98% achieved for the total retina are also comparable with the values previously reported (ICCs of 69% to 99%). Besides, lower repeatability and reproducibility coefficients were obtained for the total retina in the central region (i.e. R1) where large variations in retinal thickness occur due to the shape of the foveal depression (see Table 8). In addition, whichever observer or visit was considered, mean retinal thickness values in healthy subjects were very similar.

In general, the higher variability found in the peripheral regions may be attributed to relatively fewer sampled points. The intraobserver repeatability coefficient for the total retinal thickness was less than 7 µm for all regions, indicating that thickness changes of 14 µm can be detected over time with 95% confidence. Similarly, interobserver and intervisit reproducibility coefficients for the total retinal thickness were less than 9 µm and 6 µm for all regions, respectively; indicating that thickness abnormalities of 18 µm and 12 µm can be detected over time with 95% confidence. Furthermore, the intraobserver repeatability coefficient for intraretinal layers (except the GCL+IPL complex) was less than 4 µm (6 µm for GCL+IPL complex) for all regions, indicating that thickness changes of 8 µm (12 µm) can be detected over time with 95% confidence. Likewise, the intervisit reproducibility coefficient for intraretinal layers (except the GCL+IPL complex) was less than 4 µm (5 µm for the GCL+IPL complex) for all regions, indicating that thickness changes of 8 µm (10 µm) can be detected over time with 95% confidence. The results herein, also indicated a higher thickness of the RNFL and GCL+IPL complex within 1 mm nasal to the foveal center compared to all other regions due to an increase in the ganglion cell axon and nerve fiber layer thickness in this region. Similarly, the thickness of these layers minimized at the foveal center because of the anatomical structure of the fovea. Moreover, a higher thickness value was also obtained for the ONL at the fovea (i.e., R1) compared to all other regions due to the elongated foveal cone photoreceptors.

The results, herein, for the regional thickness analysis showed ICCs of 85-98% along with coefficients of repeatability and reproducibility less than 5 and 7%, respectively. In addition, intraobserver SDs of 1 to 6 µm, interobserver SDs of 5 to 8 µm, and intervisit SDs of 1 to 5 microns were obtained. Other groups have measured similar values for normal subjects. For example, Polito et al. (*Arch Ophthalmol* 2005; 123:1330-1337) obtained ICCs of 80-99%, SDs of 2 to 11 µm, along with coefficients of repeatability and reproducibility less than 8 and 10%, respectively. As with previous findings, change of examiner or grader did not significantly affect the reproducibility of the measurements in healthy eyes.

Conclusions

It is well known that repeatability and reproducibility of measurements is strictly dependant on how easily the optical cross sections can be consistently placed over the same points during each scan, how great the variation in retinal thickness along neighboring points is, and how many points are measured for each region. In this study, thickness measurements obtained for each of the 9 ETDRS like-regions are more repeatable and reproducible in the pericentral than in the peripheral ring. The INL, OPL, and OS/RPE junction were not very well reproducible in the regional analysis. Reproducibility could be improved for these layers by increasing the number of A-scans, which will produce an image with a high transverse pixel density, resulting in a better image quality. Conversely, this will increase the image acquisition time, which could lead to measurement errors due to eye motion. However, acquisition speed and resolution, which presented early challenges in OCT development, have experienced remarkable improvements with the introduction of a newer generation of OCT known as spectral domain OCT. These improvements are likely to partially afford the best solutions to the limitation of existing OCT software by providing images with higher resolution along with a dense map of the retina with precise registration and localization. Even though the results presented are based on Stratus OCT images, the main purpose was to establish the feasibility of our quantitative methodology for OCT image analysis independent of the technology used. OCTRIMA could facilitate a well defined and standardized quantitative analysis for the assessment of retinal diseases and its progression using OCT images obtained with Stratus OCT and SDOCT devices. This study was performed on a young group of healthy subjects (undilated eyes) and showed a high ICC for all three groups of comparisons for the total retina, the GCL+IPL complex and the ONL. Future studies will examine the repeatability and reproducibility of macular segmentation mapping with OCTRIMA in older healthy subjects and patients with early diabetic retinopathy and other retinal diseases.

TABLE 7

Mean thickness and standard deviation (SD) values for 1ten healthy eyes obtained for each ETDRS region.

| Layer | Scan 1 (E1D1S1) | Scan 2 (E1D1S2) | Scan 3 (E2D1S1) | Scan 4 (E1D2S1) |
|---|---|---|---|---|
| RNFL | | | | |
| R1 | NL | NL | NL | NL |
| R2 | 34.09 ± 2.23 | 33.51 ± 2.85 | 35.10 ± 3.76 | 34.92 ± 2.42 |
| R3 | 31.06 ± 3.57 | 31.34 ± 2.99 | 33.30 ± 5.02 | 33.26 ± 3.26 |
| R4 | 31.32 ± 2.21 | 32.4 ± 2.27 | 31.04 ± 2.12 | 31.09 ± 1.57 |
| R5 | 19.97 ± 1.58 | 20.96 ± 3.05 | 21.62 ± 2.86 | 20.39 ± 3.21 |
| R6 | 51.31 ± 4.33 | 50.99 ± 4.25 | 52.07 ± 3.99 | 51.39 ± 4.73 |
| R7 | 55.57 ± 4.96 | 56.39 ± 4.96 | 55.72 ± 5.28 | 56.77 ± 4.85 |
| R8 | 39.1 ± 2.53 | 39.28 ± 1.71 | 38.81 ± 1.93 | 39.36 ± 1.94 |
| R9 | 24.63 ± 0.91 | 25.84 ± 3.51 | 26.45 ± 3.95 | 25.74 ± 3.66 |
| GCL + IPL | | | | |
| R1 | NL | NL | NL | NL |
| R2 | 87.94 ± 10.62 | 87.85 ± 9.79 | 86.17 ± 11.07 | 87.19 ± 11.39 |
| R3 | 90.89 ± 10.24 | 90.5 ± 10.92 | 88.51 ± 11.86 | 90.51 ± 10.26 |
| R4 | 85.92 ± 9.16 | 84.75 ± 9.87 | 84.74 ± 11.39 | 85.8 ± 10.22 |
| R5 | 89.78 ± 7.99 | 87.97 ± 8.62 | 86.90 ± 11.24 | 89.36 ± 8.31 |
| R6 | 54.79 ± 8.17 | 54.52 ± 8.21 | 52.35 ± 9.58 | 54.63 ± 8.27 |
| R7 | 60.08 ± 9.92 | 60.6 ± 7.1 | 57.82 ± 10.76 | 59.77 ± 8.24 |
| R8 | 48.37 ± 7.88 | 47.29 ± 8.75 | 46.27 ± 7.57 | 49.17 ± 6.92 |
| R9 | 57.7 ± 8.46 | 55.53 ± 8.68 | 53.44 ± 9.06 | 57.28 ± 7.86 |
| INL | | | | |
| R1 | NL | NL | NL | NL |
| R2 | 36.5 ± 1.82 | 37.19 ± 2.22 | 36.62 ± 2.13 | 36.93 ± 2.1 |
| R3 | 36.52 ± 2.42 | 37.22 ± 1.93 | 37.01 ± 2.51 | 37.19 ± 2.69 |
| R4 | 36.8 ± 1.58 | 36.91 ± 1.36 | 37.41 ± 1.33 | 36.6 ± 1.66 |
| R5 | 34.15 ± 1.61 | 34.37 ± 1.88 | 34.70 ± 1.96 | 33.93 ± 2.43 |
| R6 | 28.89 ± 2.5 | 30.5 ± 3.18 | 29.77 ± 1.46 | 29.12 ± 1.65 |
| R7 | 31.25 ± 1.84 | 31.16 ± 4.02 | 31.85 ± 2.76 | 31.03 ± 2.71 |
| R8 | 29.84 ± 1.71 | 31.36 ± 2.4 | 31.51 ± 3.25 | 30.69 ± 2.69 |
| R9 | 29.6 ± 2.03 | 29.62 ± 2.26 | 30.81 ± 2.47 | 30.28 ± 1.28 |
| OPL | | | | |
| R1 | NL | NL | NL | NL |
| R2 | 33.72 ± 1.52 | 34.49 ± 1.99 | 33.54 ± 1.31 | 34.34 ± 1.46 |
| R3 | 33.85 ± 0.91 | 35.03 ± 2.06 | 34.12 ± 1.45 | 34.50 ± 1.77 |
| R4 | 33.83 ± 1.66 | 34.54 ± 1.88 | 34.07 ± 2.20 | 33.75 ± 1.13 |
| R5 | 32.62 ± 1.40 | 32.97 ± 1.47 | 32.90 ± 2.20 | 32.79 ± 2.18 |
| R6 | 29.22 ± 2.00 | 28.66 ± 1.55 | 28.27 ± 1.21 | 29.77 ± 2.39 |
| R7 | 29.31 ± 1.66 | 29.46 ± 1.60 | 29.21 ± 1.75 | 30.56 ± 3.21 |
| R8 | 29.24 ± 2.50 | 28.80 ± 2.04 | 29.74 ± 3.88 | 29.23 ± 2.00 |
| R9 | 28.71 ± 1.57 | 29.34 ± 0.96 | 30.20 ± 3.00 | 28.67 ± 1.41 |
| ONL | | | | |
| R1 | 113.21 ± 8.48 | 111.95 ± 8.15 | 111.37 ± 9.21 | 111.3 ± 8.47 |
| R2 | 88.24 ± 4.99 | 88.05 ± 5.34 | 87.51 ± 5.86 | 88.39 ± 4.05 |

TABLE 7-continued

Mean thickness and standard deviation (SD) values for 1ten healthy eyes obtained for each ETDRS region.

| Layer | Scan 1 (E1D1S1) | Scan 2 (E1D1S2) | Scan 3 (E2D1S1) | Scan 4 (E1D2S1) |
|---|---|---|---|---|
| R3 | 89.87 ± 5.12 | 88.51 ± 5.43 | 88.80 ± 6.09 | 88.98 ± 4.55 |
| R4 | 84.31 ± 4.90 | 83.81 ± 4.79 | 83.21 ± 6.81 | 85.01 ± 4.92 |
| R5 | 88.73 ± 5.29 | 88.74 ± 5.52 | 88.63 ± 6.34 | 89.06 ± 5.86 |
| R6 | 75.14 ± 4.46 | 76.21 ± 5.48 | 75.01 ± 4.10 | 75.24 ± 4.96 |
| R7 | 73.34 ± 5.60 | 72.63 ± 5.54 | 73.76 ± 6.54 | 72.83 ± 6.04 |
| R8 | 71.08 ± 4.98 | 70.68 ± 5.63 | 70.68 ± 4.87 | 70.33 ± 3.43 |
| R9 | 74.80 ± 5.28 | 74 ± 4.49 | 74.98 ± 4.89 | 73.98 ± 4.70 |
| OS/RPE | | | | |
| R1 | 16.03 ± 1.72 | 15.95 ± 1.48 | 15.39 ± 1.66 | 15.49 ± 1.29 |
| R2 | 11.54 ± 1.83 | 10.74 ± 1.35 | 12.20 ± 3.47 | 11.53 ± 1.96 |
| R3 | 10.83 ± 1.88 | 10.82 ± 1.36 | 11.39 ± 1.88 | 11.66 ± 2.19 |
| R4 | 12.53 ± 2.53 | 12.63 ± 3.12 | 12.86 ± 3.52 | 12.19 ± 2.51 |
| R5 | 10.96 ± 1.72 | 12.26 ± 2.68 | 11.83 ± 2.29 | 11.60 ± 1.77 |
| R6 | 13.97 ± 2.72 | 12.13 ± 1.73 | 13.60 ± 2.93 | 12.91 ± 2.11 |
| R7 | 13.78 ± 1.77 | 12.53 ± 2.35 | 12.57 ± 2.17 | 13.91 ± 1.87 |
| R8 | 14.17 ± 3.14 | 13.48 ± 1.52 | 13.58 ± 2.57 | 13.33 ± 3.04 |
| R9 | 13.61 ± 2.06 | 12.48 ± 2.17 | 13.33 ± 2.08 | 11.82 ± 1.81 |
| Total Retina | | | | |
| R1 | 215.09 ± 15.65 | 217.47 ± 15.8 | 219.34 ± 17.56 | 217 ± 18.25 |
| R2 | 311.5 ± 15.47 | 314.26 ± 17.63 | 311.58 ± 18.69 | 313.5 ± 17.19 |
| R3 | 313.26 ± 16.68 | 314.75 ± 17.53 | 315.23 ± 20.43 | 315.6 ± 18.23 |
| R4 | 304.13 ± 13.04 | 305.47 ± 15.04 | 303.49 ± 17.61 | 304.3 ± 15.72 |
| R5 | 298.20 ± 12.29 | 298.56 ± 12.89 | 299.08 ± 17.33 | 298.7 ± 14.10 |
| R6 | 272.49 ± 9.41 | 275.44 ± 12.67 | 271.72 ± 12.82 | 274.3 ± 10.66 |
| R7 | 281.49 ± 11.49 | 283.90 ± 12.31 | 282.78 ± 16.29 | 283 ± 13.24 |
| R8 | 250.71 ± 9.02 | 251.90 ± 10.85 | 251.37 ± 10.16 | 252.4 ± 10.47 |
| R9 | 248.8 ± 11.79 | 248.75 ± 12.36 | 250.73 ± 13.54 | 250.4 ± 10.76 |

Values shown were obtained for the total retina and six intraretinal layers during each scanning session.
E1D1S1 is the first set of scans acquired by Examiner 1 on Day 1 during Session 1;
E1D1S2 is the second set of scans acquired by Examiner 1 on Day 1 during Session 2;
E2D1S1 is the third set of scans acquired by Examiner 2 on Day 1 during Session 1 and E1D2S1 is the fourth set of scans acquired by Examiner 1 on Day 2 during Session 1.
R1 to R9 represent the 9 ETDRS-like regions of the macula.
NL indicates "No Layer" present in the region.
The mean thickness and SD values are reported in micrometers.

TABLE 8

Coefficients of repeatability and reproducibility obtained for each intraretinal layer thickness and the total retinal thickness. Values are provided for each ETDRS region.

Coefficients of Repeatability (Intraobserver Variability) (%)

| E1D1S1 - E1D1S2 | RNFL | GCL + IPL | INL | OPL | ONL | OS/ RPE | Total Retina |
|---|---|---|---|---|---|---|---|
| R1 | NL | NL | NL | NL | 2.54 | 24.33 | 4.75 |
| R2 | 10.50 | 7.64 | 10.85 | 11.28 | 4.23 | 17.32 | 3.32 |
| R3 | 8.31 | 4.79 | 11.94 | 11.31 | 7.10 | 22.13 | 3.94 |
| R4 | 16.06 | 7.91 | 8.09 | 6.71 | 5.30 | 40.74 | 3.96 |
| R5 | 23.80 | 8.61 | 13.61 | 10.05 | 6.90 | 53.02 | 3.30 |
| R6 | 10.52 | 20.34 | 22.19 | 8.99 | 5.75 | 32.62 | 3.22 |
| R7 | 10.95 | 11.47 | 14.76 | 21.46 | 5.53 | 33.04 | 3.04 |
| R8 | 16.16 | 17.24 | 12.23 | 11.42 | 5.68 | 30.12 | 3.13 |
| R9 | 24.64 | 15.14 | 13.39 | 10.54 | 5.81 | 31.37 | 3.34 |

Coefficients of Reproducibility (Interobserver Variability) (%)

| E1D1S1 - E2D1S1 | RNFL | GCL + IPL | INL | OPL | ONL | OS/ RPE | Total Retina |
|---|---|---|---|---|---|---|---|
| R1 | NL | NL | NL | NL | 5.36 | 43.50 | 6.14 |
| R2 | 18.09 | 7.21 | 5.65 | 11.65 | 7.49 | 48.41 | 4.96 |
| R3 | 9.12 | 6.77 | 8.81 | 11.44 | 10.67 | 62.84 | 4.36 |
| R4 | 18.00 | 9.87 | 6.93 | 9.85 | 7.52 | 36.85 | 5.44 |
| R5 | 19.51 | 10.45 | 13.59 | 14.54 | 7.25 | 46.76 | 3.42 |
| R6 | 7.65 | 16.41 | 17.24 | 14.68 | 10.44 | 42.27 | 5.69 |
| R7 | 7.13 | 21.74 | 22.55 | 29.95 | 14.53 | 57.49 | 3.79 |
| R8 | 19.61 | 22.25 | 15.65 | 22.84 | 7.29 | 42.87 | 4.19 |
| R9 | 29.36 | 20.54 | 15.07 | 20.24 | 7.06 | 36.01 | 5.32 |

Coefficients of Reproducibility (Intervisit Variability) (%)

| E1D1S1 - E1D2S1 | RNFL | GCL + IPL | INL | OPL | ONL | OS/ RPE | Total Retina |
|---|---|---|---|---|---|---|---|
| R1 | NL | NL | NL | NL | 4.69 | 26.59 | 4.35 |
| R2 | 11.31 | 6.07 | 10.03 | 13.41 | 5.49 | 39.11 | 3.16 |
| R3 | 12.02 | 4.65 | 7.45 | 8.64 | 7.45 | 30.64 | 3.26 |
| R4 | 18.82 | 8.17 | 9.45 | 10.70 | 6.35 | 28.45 | 3.35 |
| R5 | 22.85 | 5.31 | 14.01 | 17.32 | 4.13 | 30.79 | 3.46 |
| R6 | 9.11 | 12.15 | 16.88 | 13.44 | 5.58 | 27.31 | 3.26 |
| R7 | 8.23 | 13.80 | 16.40 | 19.20 | 5.97 | 55.05 | 1.37 |
| R8 | 16.47 | 16.07 | 4.89 | 13.47 | 5.89 | 36.10 | 1.35 |
| R9 | 25.05 | 13.92 | 9.38 | 13.63 | 5.71 | 32.33 | 1.51 |

TABLE 9

ICCs obtained for the total retina and 6 intraretinal layers.

| Regions | Intraobserver (E1D1S1-E1D1S2) | Interobserver (E1D1S1-E2D1S1) | Intervisit (E1D1S1-E1D2S1) |
|---|---|---|---|
| Total Retina | | | |
| R1 | 0.94 | 0.87 | 0.95 |
| R2 | 0.94 | 0.91 | 0.95 |
| R3 | 0.95 | 0.92 | 0.95 |
| R4 | 0.91 | 0.90 | 0.94 |
| R5 | 0.88 | 0.85 | 0.94 |
| R6 | 0.90 | 0.89 | 0.86 |
| R7 | 0.91 | 0.88 | 0.94 |
| R8 | 0.90 | 0.88 | 0.97 |
| R9 | 0.94 | 0.86 | 0.98 |
| RNFL | | | |
| R1 | NL | NL | NL |
| R2 | 0.58 | 0.63 | 0.72 |
| R3 | 0.88 | 0.70 | 0.69 |
| R4 | 0.72 | 0.71 | 0.68 |
| R5 | 0.30 | 0.23 | 0.35 |
| R6 | 0.74 | 0.87 | 0.86 |
| R7 | 0.85 | 0.93 | 0.86 |
| R8 | 0.46 | 0.59 | 0.57 |
| R9 | 0.12 | −0.05 | 0.18 |
| GCL + IPL | | | |
| R1 | NL | NL | NL |
| R2 | 0.95 | 0.93 | 0.95 |
| R3 | 0.96 | 0.94 | 0.98 |
| R4 | 0.98 | 0.94 | 0.98 |
| R5 | 0.90 | 0.88 | 0.91 |
| R6 | 0.80 | 0.72 | 0.92 |
| R7 | 0.84 | 0.93 | 0.95 |
| R8 | 0.92 | 0.59 | 0.87 |
| R9 | 0.85 | 0.68 | 0.89 |
| INL | | | |
| R1 | NL | NL | NL |
| R2 | 0.27 | 0.53 | 0.54 |
| R3 | 0.60 | 0.89 | 0.74 |
| R4 | 0.05 | 0.47 | 0.70 |
| R5 | 0.62 | 0.38 | 0.62 |
| R6 | 0.56 | 0.21 | 0.17 |
| R7 | 0.52 | 0.43 | 0.60 |
| R8 | 0.15 | −0.09 | 0.34 |
| R9 | 0.59 | 0.28 | 0.61 |
| OPL | | | |
| R1 | NL | NL | NL |
| R2 | 0.19 | 0.35 | −0.04 |
| R3 | −0.07 | 0.43 | −0.12 |
| R4 | 0.71 | 0.53 | 0.56 |
| R5 | 0.78 | 0.63 | 0.52 |
| R6 | 0.50 | −0.03 | 0.07 |
| R7 | 0.75 | 0.34 | 0.64 |
| R8 | 0.03 | 0.05 | 0.22 |
| R9 | 0.24 | 0.13 | 0.16 |
| ONL | | | |
| R1 | 0.93 | 0.89 | 0.92 |
| R2 | 0.92 | 0.87 | 0.89 |
| R3 | 0.84 | 0.78 | 0.81 |
| R4 | 0.91 | 0.70 | 0.87 |
| R5 | 0.93 | 0.83 | 0.87 |
| R6 | 0.81 | 0.74 | 0.93 |
| R7 | 0.94 | 0.78 | 0.92 |
| R8 | 0.92 | 0.43 | 0.88 |
| R9 | 0.90 | 0.88 | 0.90 |
| OS/RPE | | | |
| R1 | 0.76 | −0.11 | 0.31 |
| R2 | 0.01 | 0.20 | 0.43 |
| R3 | 0.85 | −0.27 | 0.34 |
| R4 | 0.87 | 0.37 | 0.79 |
| R5 | 0.28 | 0.30 | 0.47 |
| R6 | −0.01 | 0.45 | 0.64 |
| R7 | 0.44 | −0.15 | 0.61 |
| R8 | 0.49 | 0.00 | 0.13 |
| R9 | 0.45 | 0.34 | 0.18 |

Example 10

Improving Image Segmentation Performance and Quantitative Analysis Via a Software Tool for OCT Retinal Image Analysis Materials and Methods Data Collection to be Studied:

The study conducted in this paper followed the Health Insurance Portability and Accountability Act-compliant and was approved by the Institutional Review Board in our institutions. The research adhered to the tenets set forth in the declaration of Helsinki. A preexisting report and image repository in our institutions was retrospectively searched for individuals of all ages and both sexes who underwent Stratus OCT imaging of the macula. All study cases were obtained between Jan. 1, 2002, and Dec. 10, 2008, using the radial lines protocol (1024 samples×512 A-scans per B-scan) on a single Stratus OCT instrument (version 4.0 software). Complementary cases with clinically significant intraretinal features from Stratus OCT and SDOCT systems were also collected, for demonstration purposes only. In addition, to demonstrate intragrader and intergarder reproducibility of OCTRIMA and the comparability of STRATUS and OCTRIMA-derived regional thickness results, the same set of ten healthy eyes were used from five normal subjects as reported previously (D. Cabrera DeBuc, et al., *J. Biomed. Opt*, 14(6) (November/December 2009)) ranging in age from 25 to 34 yr (mean age 29 yr). All subjects underwent visual acuity testing with refraction and a complete slit-lamp examination. Informed consent was obtained from each subject.

Macular radial line scans of the retina for each case were exported to disc with the export feature available in the Stratus OCT device, and total retinal thickness measurements were obtained as provided by the Stratus OCT built-in algorithms as well as with the OCTRIMA software. OCTRIMA's measurements are obtained by calculating the thickness between the inner limiting membrane (ILM) and the inner boundary of the second hyperreflective band corresponding to the inner surface of the outer segment/retinal pigment epithelium (OS/RPE) junction; whereas Stratus OCT measurements are calculated between ILM and the inner boundary of the innermost hyperreflective band corresponding to the inner segment-outer segment (IS/OS) border. Stratus OCT retinal thickness measurements were compared with the OCTRIMA measurements in each of the nine macular regions defined by the Early Treatment Diabetic Retinopathy Study (ETDRS). Differences in the measurements of the macular volume measurements were also calculated. Moreover, the agreement of the thickness measured by OCTRIMA and Stratus OCT and those recently obtained with Fourier-domain OCT (FD-OCT) systems were also evaluated.

OCTRIMA System:

OCTRIMA was developed using the Matlab graphical user interface design environment (GUIDE) tool that allows interactive design of a graphical window along with variables and commands linked to it (The Mathworks, Natick, Mass.). Specifically, OCTRIMA is a research software application package that integrates an automated and semiautomated segmentation algorithm along with the manual correction tool into a user-friendly graphical user interface (GUI). The OCTRIMA software originally written in Matlab code is converted into C and requires the MatLab Component Runtime (MCR), which must also be installed on the end-user's computer. It also requires a PC with the WINDOWS™ operating system installed (Microsoft Corp., Redmond, Wash.). The application essentially provides dual functionality in a single software package by combining image enhancement and speckle denoising of Stratus OCT images along with intraretinal segmentation and error correction using direct visual evaluation of the detected boundaries. Moreover, the software has the capability to perform calculations based on measured values of corrected thickness and reflectance of the various cellular layers of the retina and the whole macula.

The user interface of OCTRIMA is mainly organized into panels that group GUI components and make the GUI easier to understand by visually grouping related controls. The GUI guides the user in an organized manner by activating only relevant functions and disabling other functions at any given time, achieved by effectively using the Matlab handles structure.

The input of the OCTRIMA software simply consists of two types of data files: 1) the data file with the patient information (i.e., a text file exported from the Stratus OCT system) and 2) the raw scan data (i.e., the image file). In addition, OCTRIMA facilitates the analysis of OCT images from two OCT scanning protocols: regular high-resolution (1024×512) and fast low-density mode (128×512). In addition, the file, view, data and help menus provide various options for file management, image data and segmentation results viewing, image processing and quantitative analysis, generating and exporting the results in various format and comprehensive visual help. Moreover, multiple OCT B-scans can be loaded at once and viewed one at a time by using the review option in the File menu. OCTRIMA also include functions that use custom built algorithms developed for generating the report for quantitative analysis, exporting the numerical results (i.e., thickness and reflectance data) to a MS Excel spreadsheet and generating topographic and fractional loss maps for the retinal thickness of the overall macula and each intraretinal layer. In addition, a final report in PDF format can be also generated.

Automated Segmentation Module:

In the OCTRIMA startup screen in the automated mode, the general information panel displays the name of the displayed OCT B-scan and its saved segmentation results as well as important subject and OCT B-scan information such as left eye (OS) or right eye (OD), scan date, the scan angle orientation (in degrees) and its pictorial representation. The "Control Panel" in automatic mode facilitates the following functionalities: 1. Preprocessing of OCT raw data. The filtering of the speckle noise is performed during the preprocessing step. The preprocessing algorithm parameters are a set of invariant numerical values that already have been optimized and hence it is encapsulated and invisible to the user. 2. Automated segmentation of the various cellular layers of the retina. Segmentation is achieved by finding peaks on each sampling line using the structure coherence matrix. A total of eight intraretinal boundaries are automatically detected while the outer boundary of the IS/OS and a Choriocapillaris section are assumed at fixed distances using anatomical knowledge. Thus, a total of ten boundaries and seven intraretinal layers are extracted. More details of the segmentation process can be found in Cabrera et al. (*Opt. Express* 13, 10200-10216 (2005)). 3. Semiautomatic correction of discontinuities in each detected boundary after automated segmentation.

Manual Correction Module:

Segmentation of the object of interest is considered a difficult step in the analysis of medical images. Fully automatic methods sometimes fail, producing incorrect results and requiring the intervention of a human operator. This is often true in ophthalmic applications such as OCT where image segmentation is particularly difficult due to restrictions imposed by image acquisition, ocular pathology and biological variation. Consequently, the intervention of a human operator is often needed to correct the segmentation result manually. Strategies that allow a trained human expert to correct segmentation errors may provide a suitable mechanism for increasing the precision of retinal measurements for monitoring patients with macular disease, particularly in clinical trials.

Computer aided manual correction of OCT segmentation may be useful for correcting thickness measurements in cases with errors of automated retinal boundary detection and may also be useful for quantitative analysis of clinically relevant features, such as the volume of subretinal fluid and intraretinal fluid-filled regions. For example, it is well known that detection algorithms fail when the retinal structure is disrupted by fluid accumulation which can lead to inaccurate measurements of retinal thickness. Thus, there is a need for developing efficient, user-friendly software tools that will supplement accurate automated boundary detection algorithms to generate more precise segmentation of the various cellular layers of the retina. For instance, an interactive procedure could be activated, by means of which the user edits the segmentation directly or provides extra information to reconfigure the computational part. If the result generated by the computational part is wrong, the user can correct it directly using a manual editor.

In OCTRIMA, various manual corrective functions are implemented to assist the user in correcting retinal segmentation errors resulting from the automated and semiautomated segmentation process. These errors are mainly due to both the presence of high reflectivity regions in the inner retina and loss of retinal structure information in local regions along the retinal cross-section as visualized by the commercial OCT system. All the functions and algorithms used in the manual correction process display the delineation of the retinal boundaries on the screen, enabling the user to instantly evaluate its location on the image grid. Different visualization schemes are adopted to show the detected layers as well as the corrections in color for better discrimination from the grey image in the background.

Additional OCTRIMA-Based Measures:

OCTRIMA also offers objective and intuitive additional functions for evaluating and comparing the efficacy of different therapeutic modalities. Since normative data for OCT analysis are crucial to compare various treatment strategies, OCTRIMA facilitates normative data from healthy controls and also allows the user to generate a new norm using healthy or pathological subjects. The OCTRIMA's norm is based on data from 74 healthy subjects (35±13 yr).

OCTRIMA also provides an indicator to evaluate the quality of the OCT B-scans. Generally, the standard deviation of the foveal center point thickness is used as a measure of the scan variance. A high standard deviation (>10% of center point thickness) indicates high variability, usually due to patient movement or boundary line error, and therefore incorrect center point thickness. Good quality images have a standard deviation <10% of center point; good clarity of the layers and are also well centered. Substantially decentered scans could have a low standard deviation. Thus, a scan quality factor (SQF) based on the standard deviation calculation (in %) of the foveal center point (FCP) for the six radial line scans is included in the OCTRIMA software. A good scan has a SQF=1, indicating that the percentage standard deviation of the foveal center point is ≤10. In addition, OCTRIMA provides a standardized method for reporting changes in thickness as a percentage of total possible change based on normative OCT data. The "Calculate standardized thickness change" function calculates the total percentage change observed in the patient using the segmentation results before and after treatment.

Statistical Methods:

The coefficients of reproducibility were calculated using the methods outlined by Bland and Altman for each of the averaged thickness measurements obtained for the total retina and intraretinal layers. The coefficients of reproducibility were computed from the standard deviations (SDs) of the differences between measurements made by each grader. The statistical analysis was performed using the software package SPSS version 16 (SPSS Inc, Chicago, Ill.).

Results

Comparison of Stratus OCT Thickness Measurements and OCTRIMA Thickness Measurements:

In contrast to Stratus OCT thickness calculations, OCTRIMA measurements of retinal thickness were obtained using the inner surface of the second hyperreflective band, that is assumed to be the OS/RPE junction. Table 10 shows the level of agreement between OCTRIMA and Stratus OCT when the two methods are applied on the same Stratus OCT images. Pearson correlation coefficients demonstrated $R^2 > 0.98$ for all ETDRS regions. Since the calculations of OCTRIMA use the inner surface of the second hyperreflective band (i.e., OS/RPE junction) as the outer retinal border, the mean thickness difference corresponded to 11% of the measured Stratus OCT retinal thickness. These thickness differences were consistent with those obtained by comparing retinal thickness measurements between Stratus OCT and FD-OCT systems. Note that the mean difference for the fovea (R1) included only 17% of the measured value obtained by the Stratus OCT system. The mean difference results for the superior, nasal, inferior and temporal inner and outer regions of the macula (R2-R9) included 8-12% of the Stratus OCT measurements (see Table 10). Total macular volume, a measure derived from thickness in all data points of the macula, was 10% higher by OCTRIMA compared to Stratus OCT results, also supporting an average difference of 10% in thickness measurements.

TABLE 10

Comparison between Stratus OCT retinal thickness measurements and the OCTRIMA measurements obtained using the inner border of the OS/RPE junction as the outer retinal boundary (i.e., the inner boundary of the RPE). Differences in the measurement of the total macular volume are also included and are expressed in cubic millimeters ($mm^3$).

| Macular Regions | Stratus OCT (μm) | OCTRIMA (μm) | Mean Absolute Difference (μm) | Percent of the STRATUS OCT measurement (%) |
|---|---|---|---|---|
| Fovea (R1) | 184.50 | 215.09 | 30.59 | 16.58 |
| Superior Inner (R2) | 283.90 | 311.50 | 27.60 | 9.72 |
| Nasal Inner (R3) | 281.00 | 313.26 | 32.26 | 11.48 |
| Inferior Inner (R4) | 280.70 | 304.13 | 23.43 | 8.35 |
| Temporal Inner (R5) | 266.20 | 298.20 | 32.00 | 12.02 |
| Superior Outer (R6) | 243.30 | 272.49 | 29.19 | 12.00 |
| Nasal Outer (R7) | 259.00 | 281.49 | 22.49 | 8.68 |
| Inferior Outer (R8) | 232.30 | 750.71 | 18.41 | 7.92 |
| Temporal Outer (R9) | 224.40 | 248.80 | 24.40 | 10.87 |
| Mean | 250.59 | 277.30 | 26.71 | 10.85 |
| Range | (184.50-283.90) | (215.09-313.26) | (18.41-32.00) | (8.35-16.58) |
| Total macular volume ($mm^3$) | 6.99 | 7.68 | 0.69 | 9.93 |

Intragrader and Intergrader Reproducibility of Thickness Measurements:

As a result of scanning a total of ten healthy eyes, a total of 60 OCT B-scans were collected and analyzed by two independent experienced graders (G1, G2). Moreover, to assess the overall performance of the OCTRIMA software, the average (between the two graders) retinal thickness in each of the nine ETDRS regions obtained by OCTRIMA analysis was compared with the automated Stratus OCT results. All scans in the study had a signal strength of 9 or 10. Algorithm performance was visually evaluated by the experienced graders to detect segmentation errors. Criteria for algorithm error included evident disruption of the detected boundary (e.g. small peaks, linear and curve offsets), and/or detected boundary jumping to and from different anatomical structures (i.e. false segmentation). The average number of manual corrections needed per scan was three. The INL and OPL were the layers that required most of the manual corrections.

Table 11 shows the reproducibility attained by one grader (G2) after analyzing each of the ten eyes at two separate times (intragrader test, one week interval between analyses) using OCTRIMA software. Thickness measurements (mean±SD) of the total retina and intraretinal layers are also shown in Table 11. The coefficient of reproducibility (CR) obtained for the thickness measurements was less than 0.2% for the total retina, less than 0.4% for the ONL and less than 3% for the remaining layers. Overall, the median of the thickness differences as a percentage of the mean thickness was less than 1%. According to the results, the measurement accuracy of the OCTRIMA algorithm ranged between 0.27-1.47 μm (see Table 11). Excellent intragrader agreement can be observed in the Bland-Altman plots of the mean difference between both grading sessions for each of the calculated intraretinal layer thickness.

TABLE 11

Intragrader reproducibility using OCTRIMA.

|  | Mean Thickness (1st Grading) (µm) | Mean Thickness (2nd Grading) (µm) | *Mean Thickness ± SD (µm) | **Mean Absolute Difference (µm) | †Median of Difference/ Mean Thickness (%) | CR (µm) | CR (%) |
|---|---|---|---|---|---|---|---|
| RNFL | 40.76 | 40.76 | 40.76 ± 1.39 | 0.17 | 0.22 | 0.47 | 1.16 |
| GCL + IPL | 72.65 | 72.79 | 72.72 ± 7.14 | 0.43 | 0.43 | 1.47 | 2.03 |
| INL | 34.30 | 34.50 | 34.40 ± 1.25 | 0.25 | 0.56 | 0.50 | 1.45 |
| OPL | 32.64 | 32.62 | 32.63 ± 0.62 | 0.22 | 0.52 | 0.57 | 1.76 |
| ONL | 88.37 | 88.35 | 88.36 ± 4.98 | 0.10 | 0.08 | 0.27 | 6.30 |
| Total Retina | 280.50 | 280.63 | 280.56 ± 12.39 | 0.21 | 0.07 | 0.46 | 0.17 |

*Mean thickness value averaged across all 10 eyes. The mean thickness value is a result of averaging the uninterpolated thickness measurements at every A-scan location for all six B-scans of all 10 eyes.
**This value is calculated by subtracting OCTRIMA thickness measurement obtained during the 1st grading from the OCTRIMA thickness measurement obtained during the 2nd grading for each eye by the same grader G2, and then taking the absolute value.
†Median of the differences between measurements expressed as a percentage of mean thickness across all 10 eyes.

Table 12 shows the level of agreement between the two graders (intergrader reproducibility test, i.e. G1 versus G2) using the OCTRIMA software. The coefficient of reproducibility obtained for the thickness measurements was less than 0.5% for the total retina, less than 0.7% for the ONL and less than 5% for the remaining layers. According to the results the measurement accuracy of our algorithm ranged between 0.6-1.76 µm (see Table 12). Overall, the median of the thickness differences as a percentage of the mean thickness was less than 2% be negligible. In other cases, one side of the RNFL layer is completely invisible in the OCT image, like for example in the temporal part of a horizontal B-scan (see FIG. 3B). In such cases, a correction is required to overlap the inner and outer boundaries of the RNFL layer in the regions of negligible thickness (see FIGS. 3C and 3D). However, sometimes the boundary detection algorithm fails in such specific cases when localized bright spots of high intensity appear on some regions of the RNFL layer; and falsely displays the outer boundary of the RNFL layer as a result of the peak search

TABLE 12

Intergrader reproducibility using OCTRIMA

|  | Mean Thickness (Grader 1) (µm) | Mean Thickness (Grader 2) (µm) | *Mean Thickness ± SD (µm) | **Mean Absolute Difference (µm) | †Median of Difference/ Mean Thickness (%) | CR (µm) | CR (%) |
|---|---|---|---|---|---|---|---|
| RNFL | 40.76 | 40.72 | 40.74 ± 1.62 | 0.67 | 1.55 | 1.70 | 4.16 |
| GCL + IPL | 72.65 | 73.63 | 73.14 ± 7.34 | 1.11 | 1.50 | 1.76 | 2.40 |
| INL | 34.30 | 33.91 | 34.11 ± 1.14 | 0.56 | 1.17 | 1.11 | 3.27 |
| OPL | 32.64 | 32.24 | 32.44 ± 0.66 | 0.48 | 1.47 | 0.84 | 2.58 |
| ONL | 88.37 | 88.56 | 88.46 ± 4.93 | 0.26 | 0.22 | 0.60 | 0.68 |
| Total Retina | 280.50 | 280.50 | 280.51 ± 12.26 | 0.49 | 0.15 | 1.24 | 0.44 |

*Mean thickness value averaged across all 10 eyes. The mean thickness value is a result of averaging the uninterpolated thickness measurements at every A-scan location for all six B-scans of all 10 eyes.
**This value is calculated by subtracting OCTRIMA thickness measurement obtained during the 1st grading from the OCTRIMA thickness measurement obtained during the 2nd grading for each eye by the same grader G2, and then taking the absolute value.
†Median of the differences between measurements expressed as a percentage of mean thickness across all 10 eyes.

Image Segmentation Performance and Error Correction Using OCTRIMA:

Illustrative cases of diseases with subretinal anomalies and representative intraretinal boundary detection errors are shown in FIGS. 3A-3F.

Mild Non Proliferative Diabetic Retinopathy without Macular Edema:

FIGS. 3A-3F shows an OCTRIMA segmented B-scan before and after applying manual corrections. In this study case, the representative B-scan was taken from a set of images obtained for a diabetic patient with mild non-proliferative diabetic retinopathy without macular edema (male, 59 yr old). Characteristic intraretinal boundary detection errors such as small peaks, linear offsets, curve offsets and false segmentations are illustrated in FIG. 3A. False segmentation refers to the falsely detected inner and/or outer boundaries of an intraretinal layer. This particular error is most commonly found during the RNFL's outer border detection. Specifically, there are certain cases in which the true anatomical thickness of the RNFL layer (or some regions of the RNFL layer) might algorithm which looks for zero crossings in the structure. Hence, the RNFL outer boundary must be manually corrected to appear overlap the inner boundary in the invisible part of the layer. As can be seen in FIG. 3B, the ILM boundary on the inner side of the RNFL is detected but no boundary is detected on the outer left side since the RNFL is not visible on this (temporal) side for this particular scan, whereas the RNFL is bright and clearly visible on the right (nasal) side of the scan (see FIGS. 3A and 3B). FIG. 3C shows the manually corrected outer boundary of the IPL (outlined in yellow) using the "Small Peak" corrective function of the manual correction software tool which removes the overshoots or undershoots in the individual boundaries.

These are also parts of a boundary that form a straight line segment but are incorrectly detected as a peak or an elevated or depressed line segment by the automated segmentation algorithm. This detection error is classified as a linear offset. To resolve this class of error, the user has to manually select two points to draw a straight line segment on the specific boundary containing the offset. For example, a straight line segment was manually drawn to correct the linear offset in the outer boundary of the outer plexiform layer (OPL, see the boundary outlined in green in FIG. 3E. FIG. 3F shows the manual corrections for the inner and outer boundaries of the inner nuclear layer (INL, outlined in yellow and cyan, respectively) which had segmentation errors as a result of curve offsets (see FIG. 3A). Curve offset is a term given to the curved portion of a boundary that has not been recognized as a curve, instead, has been incorrectly segmented as an elevated or depressed curve. Curve offsets have been rectified using a function based on a customized contour model which was originally introduced to identify non-convex shapes in OCT images. This function allows the user to select multiple closely spaced points that will be joined to trace a curve and remove the offset. FIG. 3F shows the result of the "Curve Plotting" function applied to correct the inner and outer boundaries of the INL (outlined in yellow and cyan, respectively).

Additionally, an OCTRIMA predefined control is also in place for the inner retinal layers (RNFL, ganglion cell and inner plexiform layer complex (GCL+IPL) and INL) and outer plexiform layer (OPL) in a 1.5 mm diameter zone in the fovea, where retinal reflections are minimally visible. The control forces the ILM, the inner and outer side of the GCL+IPL complex, and the outer side of the INL and OPL to be coincident in this region (see FIG. 3A). Sometimes, small peaks appear at the periphery of this controlled foveal region. In such a case, it appears that the coincident layers deviate from the true foveal visible boundary and need to be corrected so that they overlap in the periphery of the controlled foveal region. Thus, the "Overlap" function of the manual correction software tool is useful to rectify the segmentation at the fovea (see FIG. 3D).

OCTRIMA thickness maps for the overall macula and each intraretinal layer obtained from the patient image data shown in FIGS. 3A-3F are as follows. The ETDRS-like regions are based on nine sectional thickness values in three concentric circles obtained from interpolation of the six linear scans, with diameters of 1, 3 and 6 mm. These maps are obtained according to the standards set by the ETDRS similarly to the Stratus OCT analysis software and can be easily exported to a PDF document along with the numerical results in tabulated format. The output data includes three main quantitative measures: thickness, volume and reflectance. The sectional measurements in the retinal thickness map are calculated from the averaged data from the six individual scans. The norm used in OCTRIMA was obtained from 74 healthy eyes (35±13 yr).

Figure 6B:
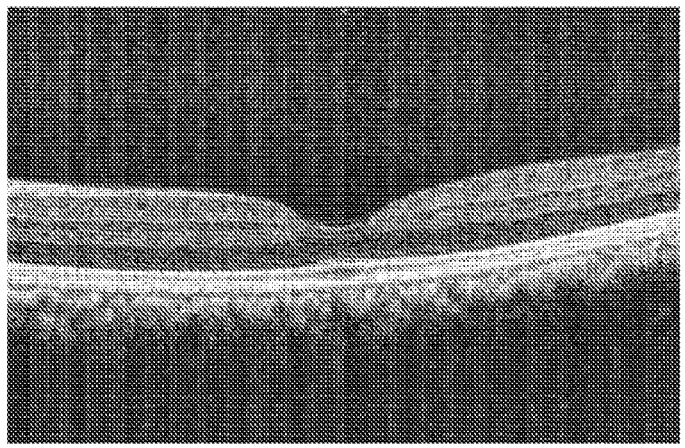
FIG. 6B shows the OCTRIMA segmentation results for an OCT image obtained with the Bioptigen Spectral Domain ophthalmic imaging system.

Neovascular Age-Related Macular Degeneration:

It is well known that the current standard algorithms for obtaining the retinal thickness and volume information are error-prone when used to evaluate edematous retina and are unable to independently assess fluid under the retina and the retinal pigment epithelium. Even when the current algorithm accurately identifies the appropriate boundaries, the retinal volume and thickness calculations only take into account the entire area between the outer reflective band (retinal pigment epithelial layer) and the inner retinal surface. Thus, the algorithms are unable to independently assess the area and volume of the fluid filled cystic areas within and under the retina that represents leakage from choroidal neovascularization (CNV). However, OCTRIMA allows the user to trace the internal boundary of visible nonconvex shaped structures such as intraretinal and subretinal fluid-filled regions, if present and visible on the OCT B-scan. To quantify the area of these fluid-filled regions, an active contour model was used to outline these regions. Common errors occur in retinal boundary detection by the Stratus OCT software, for example, in scans obtained from a patient with neovascular age-related macular degeneration. In neovascular AMD, the fluid accumulation usually can be identified within the retina, under the retina, and under the RPE layer. In this case, peripheral and pericentral fluid-filled regions were observed in the OCT B-scans at presentation. Note that the Stratus algorithm erroneously detected the border of the innermost hyperreflective band in four of the six radial line scans. In addition, the fluid-filled region is included as part of the retinal structure for the thickness calculation. As a result, the retina appears thickened in this patient. OCTRIMA was able to correctly detect the boundaries of the retinal structure and the fluid-filled regions (see, FIG. 6A).

Figure 6C:
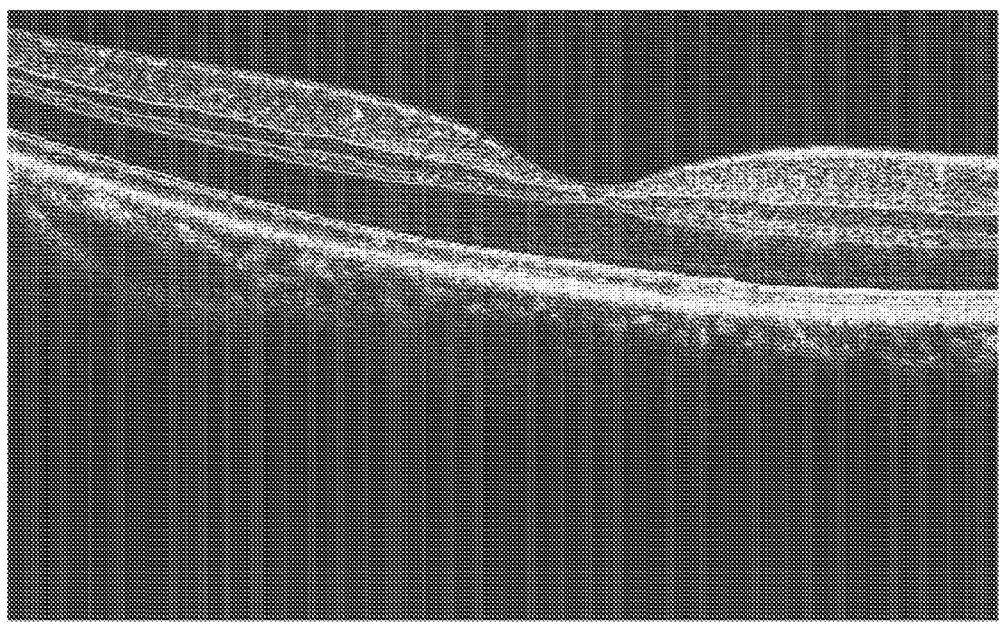
FIG. 6C shows the OCTRIMA segmentation results for an OCT image obtained with the custom developed FD-OCT adapted from our anterior segment OCT system.
Figures 7A, 7B:
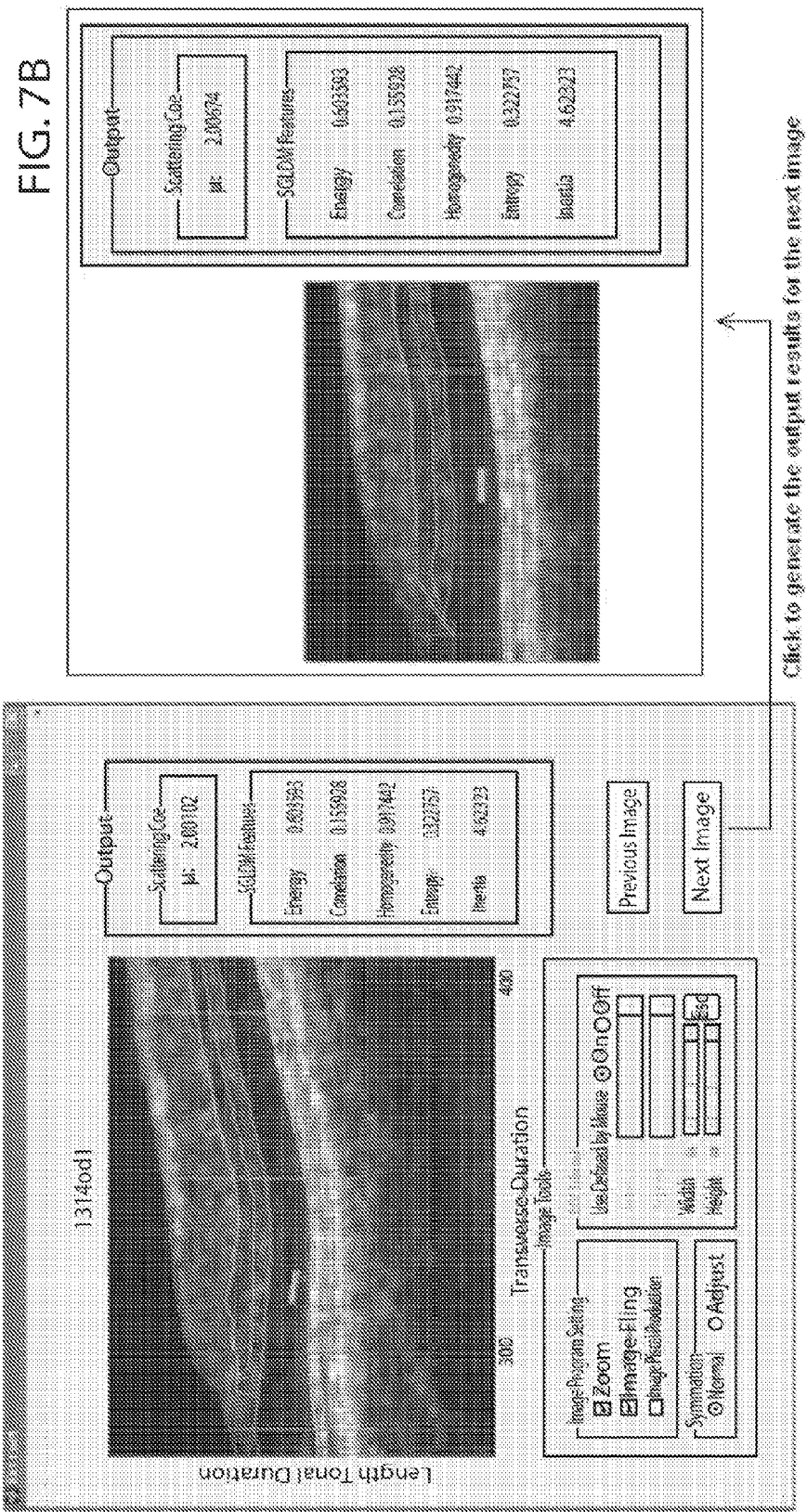
FIGS. 7A, 7B are photographs showing a graphical user interface (GUI) screenshot.
Figure 8:
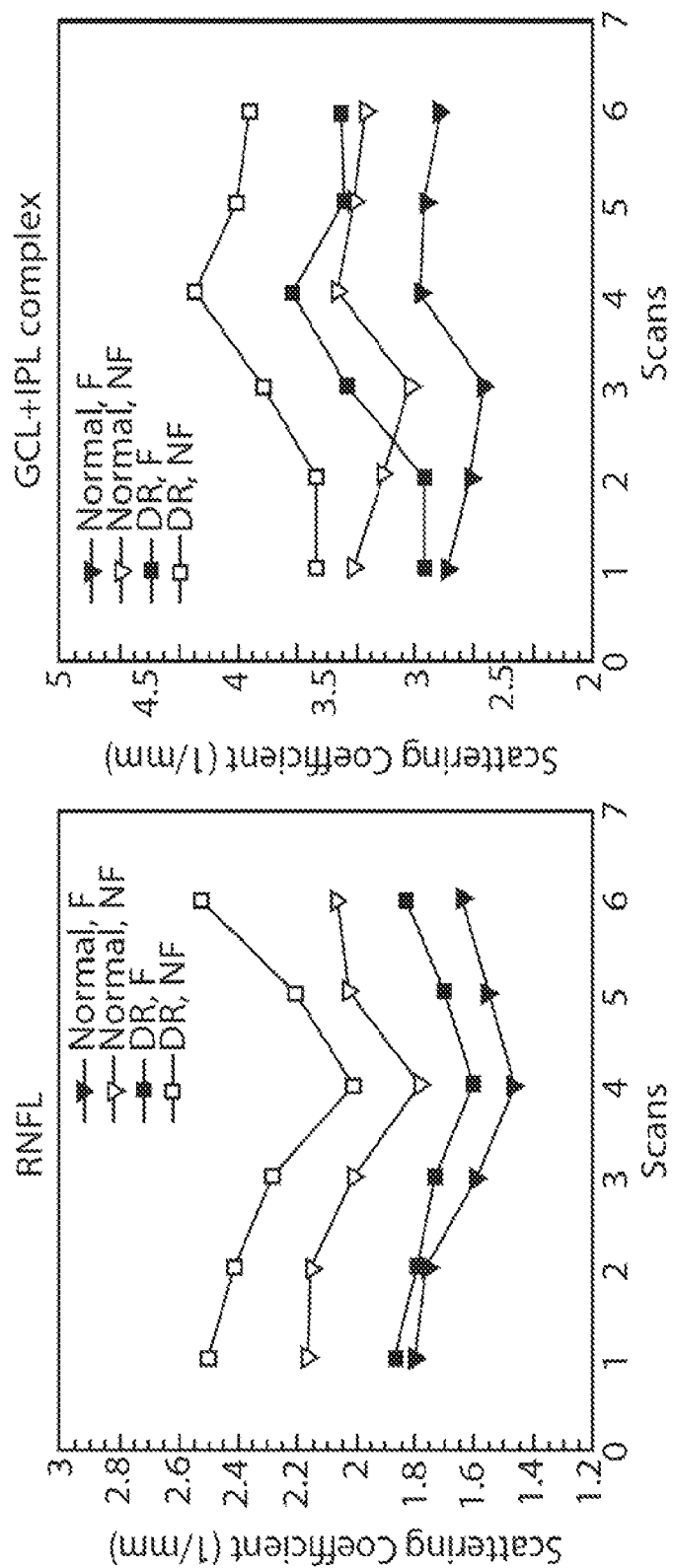
FIG. 8 shows the averaged scattering coefficient results per scan obtained for the RNFL and the GCL+IPL complex before (NF: non filtering) and after speckle denoising (F: filtering). OCT raw data from normal healthy eyes and eyes with minimal diabetic retinopathy (DR) were used. Higher values are obtained for the scattering coefficient when speckle noise is not removed.

Advanced OCT Imaging Systems:

Although the OCTRIMA quantitative analysis of Stratus OCT images described in this study is potentially useful, new OCT technologies, such as spectral domain, ultrahigh resolution and adaptive optics based OCT technology, are likely to partially afford better solutions to the limitation of existing OCT software by providing images with higher resolution along with a dense map of the retina with precise registration and localization. However, automatic segmentation algorithms for OCT data have tendency to give erroneous segmentation results especially in pathological cases, which is actually a result of the algorithm performance independently of how good the OCT image could be reproduced with a high level of detail. Consequently, in order to improve the practicability of OCT technology in ophthalmology, effective data processing requires robust and accurate segmentation algorithms integrated into intelligent software solutions (see, FIGS. 6B, 6C). In addition, computer-aided detection and diagnosis based on automatic/semiautomatic robust algorithms will be essential in clinical studies where large datasets will be impractical for manual grading approaches.

Although cases studied were based on Stratus OCT images, the main purpose was to establish the feasibility of our quantitative methodology for OCT image analysis independent of the technology used. There is no doubt that if this methodology works well for Stratus OCT images, then it should perform better for FD-OCT images which have better resolution, and as such, ensure robust segmentation. To prove this, OCTRIMA segmentation was applied to raw images taken from FD-OCT devices. OCTRIMA segmentation results were obtained for an image obtained with the Bioptigen Spectral Domain Ophthalmic Imaging System (Bioptigen Inc, Research Triangle Park, N.C.). OCTRIMA segmentation results for an OCT image from a healthy eye obtained with a custom developed FD-OCT adapted from the anterior segment OCT system with ~3 μm axial resolution. The system configuration has been detailed elsewhere (Q. Chen, et al. Invest Ophthalmol Vis Sci 2009; 0:iovs 09-4389v1-iovs. 09-4389; J. Wang, et al. *Eye & Contact Lens;* 2: 44_49 (2009)). Significant improvement has been obtained for the delineation of the INL, OPL and OS/RPE junction in the advanced OCT images analyzed.

Discussion

The most difficult part of biomedical image analysis is unsupervised segmentation, i.e., the automated localization and delineation of coherent structures of interest. However, the OCT denoising-enhancing method and quantitative methodology could be used to automatically segment the retinal structure in both normal and pathological subjects. Although the OCTRIMA software was initially developed for the quantitative analysis of Stratus OCT images, it is also potentially useful for the analysis of new OCT technologies, such as spectral domain and ultrahigh resolution based OCT technology, which provide images with higher resolution along with a dense map of the retina.

In order to accurately diagnose, study, and treat retinal diseases such as diabetic retinopathy, glaucoma and age-related macular degeneration (AMD), researchers have begun developing OCT quantitative tools. OCTRIMA helps ophthalmologists to explore Stratus OCT data by providing visualization and analysis methods, in conjunction with a segmentation method for extracting retinal layers and other structures, such as intraretinal and subretinal fluid-filled regions. The user interface allows further processing, so that users can diagnose and evaluate disease progression. In addition, OCTRIMA provides a manual correction tool that facilitates the interaction with the automated segmentation results, enabling significant improvements of segmentation accuracy.

The system herein, works well at isolating most retinal layers and structures in normal healthy controls and patients with early retinopathy and diabetic diffuse macular edema. Accordingly, a more robust and localized quantification of the retinal structure can be achieved using OCTRIMA software. The total time required to preprocess and automatically segment an OCT image (B-scan) is 20 seconds on a computer with INTEL® CORE™ 2 Extreme CPU Q9300@2.53 GHz and 8 Gb. The inventors are currently improving the automated segmentation method to reduce the time needed to correct errors in segmentation. In the example above, a high degree of repeatability, reproducibility and reliability of the OCTRIMA software was obtained using data from ten control healthy eyes.

Conclusion:

The newly designed software package (OCTRIMA) is a robust and interactive computer aided retinal image analysis system for the assessment of retinal pathologies using Stratus OCT images. The user interaction with the software is mediated using a graphic user interface that offers various types of controls and menu options to facilitate a user-friendly environment to quantitatively assess the macula and the various cellular layers of the retina. The software implements a custom segmentation algorithm to accurately identify the boundaries of the intraretinal layers with minimized errors, which is functionally more efficient as compared to the commercial Stratus OCT software. Additionally, OCTRIMA offers a unique method to manually eliminate visible irregularities, if any, in the detected boundaries between the various cellular layers of the retina. This powerful capability ensures higher accuracy in the numerical data obtained from the measurements of the thickness and reflectance of each layer and the whole macula. Additional capabilities of the newly developed software include report generation for quantitative analysis of the macula and intraretinal layers per scan and per region.

OCTRIMA can also generate and display topographic maps for the thickness of each cellular layer of the retina, which provides a visual aid for better analysis of local structural changes, if any, in each ETDRS retinal region. Another potential advantage of OCTRIMA is the incorporation of a uniform method for reporting changes in thickness, which could be used as a framework for reporting treatment outcomes. Thus, OCTRIMA can be used to compare the efficacy of current and emerging therapies, as well as monitor the progression of disease in patients. Future work will include the adaptation of OCTRIMA into a more practical interface to handle the large quantities of measured raw data generated by the advanced OCT systems. In addition, the improvement of the compilation process to obtain high performance C++ source code without relying on external heavy-weight libraries will be also considered in the future development of OCT-RIMA. The current implementation of the software is a single user based design for executing the application on the local machine. However, a networked multi-user design would be possible with a JAVA implementation of OCTRIMA, accessible world-wide using the interne. Moreover, OCTRIMA's retinal thickness measurements could be used as a primary or secondary end point for clinical trials of therapeutic agents for retinal tissue alterations under investigation by pharmaceutical companies. OCTRIMA will help physicians and their patients better evaluate the efficacy of therapeutic intervention.

Example 11

Evaluating the Effect of Speckle Denoising on the Estimation of Optical Properties of Intraretinal Layers Using Optical Coherence Tomography Optical Coherence Tomography (OCT) is a rapidly emerging imaging technology that enables visualization of the cross sectional structure of the retina and anterior eye. OCT is usually employed for the measurement of retinal thickness. However, coherent reflected light carries more information characterizing the optical properties of tissue. Before the question of whether or not OCT can quantitatively measure the optical properties of retinal tissue can be answered affirmatively, better understanding and modeling of the OCT signal from the retinal structure is needed. The purpose of this study was to evaluate the effect of speckle denoising on the estimation of optical properties of the intraretinal layers on OCT image.

Methods:

Speckle-free test Stratus OCT images from normal (168 scans) and pathological eyes (42 scans) were obtained after applying median filtering. Since the speckle pattern becomes additive white noise after the log-transformation, a Gaussian distribution approach of the speckles was considered. Therefore, the experiments were conducted on the OCT test images at different levels of Gaussian additive noise (5%, 10%, and 15%). Automatic/semi-automatic layer segmentation was performed using a custom-built algorithm (OCTRIMA). Specifically, the RNFL, GCL+IPL, INL, OPL, ONL, IS/OS and RPE layer were extracted with OCTRIMA.

Relative light-backscattering of two particular layers characterized by low (ONL) and highlight-backscatter (IS/OS) were used in the scattering coefficient ($\mu_t$) analysis. These coefficients were calculated using a finite difference method assuming a single-scattering model. The $\mu_t$ was measured from the OCT signal by fitting a model relation to this signal from a ROI in an OCT image. To improve the numerical accuracy of the $\mu_t$, the lateral coordinates of the blood vessel shadows were first extracted by using a blood vessel shadowgram technique. Then, these shadows were removed in each OCT image before calculating $\mu_t$. The signal-to-mean square error ratio (S/MSE) and ratio measurements between the $\mu_t$ values obtained before and after noise removal were used in the quantitative analysis.

Results:

AS/MSE improvement of 3%, 8% and 21% was obtained for 5% (P5F), 10% (P10F) and 15% (P15F) noise level, respectively (see Table 13). The $\mu_t$ decreased for the ONL and increased for the IS/OS when the noise level was augmented from 5 to 15% in OCT data from pathological subjects. A similar trend for the IS/OS was observed in healthy eyes (see Table 14). Once the Gaussian additive noise was removed, the $\mu_t$ of the ONL increased in both normal and pathological OCT data. On the contrary, the $\mu_t$ of the IS/OS decreased (see Table 14).

TABLE 13

S/MSE results obtained for 5%, 10% and 15% Gaussian additive noise level before and after denoising. P5, P10 and P15 represents S/MSE values obtained when a 5%, 10% and 15% Gaussian additive noise was added to the OCT raw image after median filtering. In addition, P5F, P10F and P15F represents the values obtained after the speckle-free test OCT images corrupted with Gaussian additive noise were denoised. OCT data from pathological eyes were obtained from diabetic patients with early retinopathy.

| S/MSE | | P5 (mm$^{-1}$) | P5F (mm$^{-1}$) | P10 (mm$^{-1}$) | P10F (mm$^{-1}$) | P15 (mm$^{-1}$) | P15F (mm$^{-1}$) |
|---|---|---|---|---|---|---|---|
| Healthy | ONL | 1.61 | 1.70 | 1.57 | 1.69 | 1.40 | 1.67 |
| Eyes | IS/OS | 1.99 | 2.06 | 1.92 | 2.05 | 1.77 | 2.05 |
| Pathological | ONL | 0.87 | 0.89 | 0.79 | 0.88 | 0.66 | 0.86 |
| Eyes | IS/OS | 1.37 | 1.39 | 1.31 | 1.40 | 1.16 | 1.37 |

TABLE 14

Scattering coefficient results obtained with the finite difference method.

| Scattering Coefficient | | P5 (mm$^{-1}$) | P5F (mm$^{-1}$) | P10 (mm$^{-1}$) | P10F (mm$^{-1}$) | P15 (mm$^{-1}$) | P15F (mm$^{-1}$) | (P10F − P5F)/P5F (%) | (P15F − P10F)/P10F (%) |
|---|---|---|---|---|---|---|---|---|---|
| Healthy | ONL | 2.02 ± 0.17 | 2.24 ± 0.20 | 2.10 ± 0.15 | 2.23 ± 0.21 | 2.05 ± 0.23 | 2.10 ± 0.22 | −0.08 | −6.00 |
| Eyes | IS/OS | 6.89 ± 0.36 | 6.94 ± 0.70 | 7.86 ± 0.32 | 6.88 ± 0.69 | 8.32 ± 0.59 | 7.08 ± 0.57 | −0.85 | 2.87 |
| Pathological | ONL | 2.77 ± 0.15 | 2.98 ± 0.16 | 2.62 ± 0.14 | 2.82 ± 0.13 | 2.51 ± 0.22 | 2.79 ± 0.29 | −5.39 | −1.15 |
| Eyes | IS/OS | 7.76 ± 0.93 | 7.22 ± 1.07 | 8.11 ± 0.82 | 7.15 ± 1.12 | 8.43 ± 0.48 | 7.41 ± 0.91 | −0.92 | 3.55 |

Discussion:

Discrimination of different tissues based on differences in their scattering coefficient requires its accurate measurement from OCT data. In this study it was found that the scattering coefficients extracted from OCT images were more affected as the noise level increased. In addition, higher scattering coefficients were obtained for the pathological eyes independently of the noise level added to the OCT test images. The scattering coefficients obtained for the IS/OS were higher compared to the coefficients obtained for the low contrast layer (ONL).

It was also shown that it is possible to estimate the scattering coefficients of the intraretinal layers. Experiments are also being conducted to clearly show that the origin of the observed optical changes is the altered physiological state of the retina due to the progression of disease.

Conclusion:

Localized quantitative measurement of the scattering coefficient of the intraretinal layers can provide additional information and may improve the clinical value of OCT by allowing quantitative discrimination between healthy and diseased cellular layers of the retina.

Future studies using phantom models will be conducted to determine the feasibility and full capability of this methodology to better explore the variability of optical properties of the retinal tissue.

Example 12

Comparing Quantitative Measurements Obtained Using Stratus OCT and an OCT Retinal Image Analysis (OCTRIMA) Software The commercial time-domain Stratus OCT (Carl Zeiss Meditec, Dublin, Calif.) has a measurement capability limited to retinal thickness (RT) and cannot give quantitative information on intraretinal layers. In addition, Stratus OCT built-in algorithms identify the outer retinal boundary as the inner border of the RPE layer rather than identifying its outer border, which, probably corresponds to the true anatomic allocation of the outer boundary.

In an effort to provide additional retinal quantifications along with accurate automatic/semi-automatic detection, a software tool was developed for OCT retinal image analysis (OCTRIMA) which is an interactive, user-friendly standalone application for analyzing OCT retinal images. OCTRIMA calculates the RT as the distance between the ILM and the anterior boundary of the red reflective layer corresponding to the RPE-choriocapillaris complex. In this study, the volume and RT were compared and measured by both, OCTRIMA and Stratus OCT.

Methods:

Standard macular mapping by Stratus OCT were performed in ten healthy eyes from 5 normal subjects, ranging in age from 25 to 34 years (mean age 29 years). OCTRIMA's thickness measurements were obtained by calculating the thickness between ILM and RPE inner boundary whereas automated Stratus OCT results are currently calculated between ILM and ONL (outer boundary). Stratus OCT retinal thickness measurements were compared with the OCTRIMA's measurements in each of the nine ETDRS macular regions. Differences in the measurement of the macular volume were also calculated. Moreover, the OCTRIMA and Stratus OCT thickness calculations' agreement with measurements obtained with frequency-domain OCT systems was also evaluated.

Results:

Table 15 shows the comparison between Stratus OCT retinal thickness measurements and the OCTRIMA measurements obtained using the true anatomic location of the outer retinal boundary (i.e. RPE's inner boundary). Differences in the measurement of the total macular volume are also included and are expressed in cubic millimeters (mm$^3$).

| Retina Macular Regions | Stratus OCT (μm) | OCTRIMA (μm) | Mean Absolute Difference (μm) | Percent of the STRATUS OCT measurement (%) |
|---|---|---|---|---|
| Fovea | 184.50 | 215.09 | 30.59 | 16.58 |
| Superior Inner | 283.90 | 311.50 | 27.60 | 9.72 |
| Temporal Inner | 281.00 | 313.26 | 32.26 | 11.48 |
| Inferior Inner | 280.70 | 304.13 | 23.43 | 8.35 |
| Nasal Inner | 266.20 | 298.20 | 32.00 | 12.02 |
| Superior Outer | 243.30 | 272.49 | 29.19 | 12.00 |
| Temporal Outer | 259.00 | 281.49 | 22.49 | 8.68 |
| Inferior Outer | 232.30 | 250.71 | 18.41 | 7.92 |
| Nasal Outer | 224.40 | 248.80 | 24.40 | 10.87 |
| Mean | 250.59 | 277.30 | 26.71 | 10.85 |
| Range | (185-284) | (215-313) | (18-32) | (8-17) |
| Total macular volume (mm$^3$) | 6.99 | 7.68 | 0.69 | 9.93 |

Note that the mean difference for the foveal center (R1) included only 17% of the measured value obtained by the commercial Stratus system. The mean difference results for R2-R9 included 8-12% of the Stratus OCT measurements. Moreover, the mean difference between Stratus OCT retinal thickness measurements and OCTRIMA thickness measurements was 27 microns (range, 18-32 microns), or 11% of the measured Stratus OCT retinal thickness. Total macular volume, a measure derived from thickness in all datapoint of the macula, was 10% higher by OCTRIMA compared to Stratus OCT results, also supporting an average difference of 10% in thickness measurements.

Discussion:

After comparing Stratus OCT retinal thickness measurements with the measurements obtained using the true anatomic location of the outer retinal boundary (i.e. RPE's inner boundary), the mean thickness difference was 27 μm (ranged, 18-32 μm see Table 15). Similar results have been recently reported (mean=35.5 inn, range 27-45 μm) (Sadda et al., IOVS, 2007; 48: 839-848). Similar thickness differences have been found between Stratus OCT and FD-OCT systems, which use the same method of the OCTRIMA software to calculate the total retinal thickness.

This particular observation enhances the reliability of OCTRIMA software when compared to FD-OCT systems. Although, mean difference values per ETDRS region included only 8-17% of the measured total values obtained by the commercial Stratus OCT system, further investigations related to the reliability of the segmentation of the anatomically correct location of the RPE are required before clinicians can fully rely on this newly defined true retinal thickness.

Conclusions:

These results are comparable to those obtained using frequency-domain OCT systems which clearly demonstrates the reliability of OCTRIMA software. Hence, OCTRIMA is a good candidate for potential OCT based studies examining morphologic characteristics of changes in retinal structure.

Example 13

Different Trends Observed for Age-Related Changes of the Macula Affecting the Ganglion Cells and Retinal Pigment Epithelium Optical coherence tomography (OCT) is a noninvasive, noncontact diagnostic tool that can provide in vivo, real-timecross-sectional imaging of the retina. The commercial time-domain Stratus OCT (Carl Zeiss Meditec, Dublin, Calif.) provides images with 8-10-μm axial resolution and a maximum of 512 transverse×1024 axial datapoints per image acquired in 1.25 seconds. Cross-sectional OCT images of the retina have been found to correlate well with retinal histology.

In an effort to obtain quantitative data of intraretinal structures a software tool was developed for Stratus OCT retinal image analysis (OCTRIMA). OCTRIMA is able to minimize segmentation errors and give quantitative information of intraretinal structures. The software can distinguish 7 layers of the retina on OCT images based on their optical densities: the retinal nerve fiber layer (RNFL), the ganglion cell+inner plexiform layer complex (GCL+IPL), the inner nuclear layer (INL), the outer plexiform layer (OPL), the outer nuclear layer (ONL), the inner-outer segment border (IS/OS) and the retinal pigment epithelial layer (RPE).

The quantification of changes in macular thickness as well as thickness of each cellular layer of the retina is important as it provides useful information for detecting pathologic changes and diagnosing retinal diseases. However, proper diagnosis of ophthalmic diseases requires a substantive knowledge of the expected thickness of the macula and its layers. The retina undergoes several structural changes with aging. One of these processes is the thinning of the retina and retinal nerve fiber layer (RNFL) as described in histological studies. With the introduction of newer imaging methods, several studies have shown the thinning of peripapillary RNFL with age using OCT and there have been some studies observing total retinal thickness decrease. The cause of age-related nerve fiber loss is thought to be the apoptosis of retinal ganglion cells. The purpose of the present study was to describe age-related changes of the human macula in vivo using optical coherence tomography (OCT).

Methods:

A total of 29 right and 26 left eyes of 55 healthy volunteers were recruited in this prospective study. The age of the volunteers ranged from 21 to 88 years with a median of 42 years (mean age 45, 25 years). Thirty-nine women (71%) and 16 men (29%) participated. 14 subjects underwent uneventful phaco emulsification surgery with PCL implantation 6-12 months prior to enrollment (age range 72-88 years).

The inclusion criteria for all participants were: best-corrected Snellen visual acuity of 20/20, preoperative spherical and cylindrical correction within ±3.0 diopters (D). Exclusion criteria were treated glaucoma, any abnormalities of the disc or the retinal nerve fiber layer, particularly glaucoma-like cupping; family history of glaucoma or any other hereditary eye disease, IOP≥20 Hgmm in the history, any retinal disease, even AMD st.1; diabetes mellitus or other systemic disease possibly affecting the eye except controlled hypertension; history of intraocular surgery (or any kind of laser therapy including refractive surgery) in 6 months time before the examination. In patients in whom both eyes were eligible, the study eye was selected randomly.

All subjects underwent routine ophthalmic examination including best corrected visual acuity, assessment of intraocular pressure (IOP), slit lamp biomicroscopy and binocular ophthalmoscopy after pupil dilatation.

Optical coherence tomography scans were performed using Stratus OCT (Carl Zeiss Meditec, Inc., Dublin, Calif., USA). Before recording the OCT images each eye of each subject was dilated with tropicamide 0.5%. All scans used an internal fixation target and were performed by the same operator. Standard macular mapping with "Macular Thickness Map" protocol was used for all imaging in the study which consists of six evenly spaced radial line centered on the fovea, each having a 6 mm transverse length. Average thickness was extracted for all retinal layers.

Sigmoid and linear functions were fitted using the least squares regression technique to decide which model describes better the kinetics of retina layer thickness changes occurring with age. The models were compared using the residual standard errors (RSE), the Akaike Information Criterion (AIC) and the F test on residual sum of squares.

Results:

A decrease in thickness of RNFL was observed with age which was better described by a sigmoid model, however F-test was not significant. In the case of GCL+IPL a sigmoidal trend gave a significantly better fit for the observed thickness decrease with age. The thickness of the RPE layer showed a linear increase related to age, as only a linear model could be fitted (linear correlation r=0.36, p=0.006). All other layers did not show any significant age-related thickness changes (Table 16).

TABLE 16

Statistical results for the age-related trends in the various retinal layers of the macula.

| | Linear model | | Sigmoid model | | | |
|---|---|---|---|---|---|---|
| | RSE | AIC | RSE | AIC | F-test | P |
| RNFL | 2.556 | 265.26 | 2.508 | 261.05 | 2.03 | 0.14 |
| GCL + IPL | 4.968 | 338.37 | 4.703 | 330.24 | 4.06 | 0.023 |
| INL | | | No correlation | | | |
| OPL | | | | | | |
| ONL | | | | | | |
| RPE | | | Linear correlation | | | |
| Total Retina | 9.9 | 410.11 | 9.8 | 411.58 | — | |

RSE: residual standard errors, AIC: Akaike Information Criterion.

Conclusions:

These results indicate that age-related cellular changes of the macula may occur with different kinetics. The known decrease in the ganglion cell number (and thus GCL+IPL thickness) follows a sigmoidal trend, which is paralleled by a decrease in the nerve fiber layer following the same, although less evident trend. The data herein, provide proof that physiological apoptosis occurs in the retina with age.

The linear thickening of the RPE might be in correlation with described age-related histological changes of the Bruch membrane. This study demonstrates the different kinetics in the ageing retina observed in vivo with the help the custom-built OCTRIMA software.

Other Embodiments

It is to be understood that while the invention has been described in conjunction with the detailed description thereof, the foregoing description is intended to illustrate and not limit the scope of the invention. Other aspects, advantages, and modifications are within the scope of the following claims.

All references cited herein, are incorporated herein by reference. Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed is:

1. A method of predicting early diabetic retinopathy comprising:
  obtaining thickness values from optical coherence tomogram (OCT) data for a retina of a subject;
  detecting whether an abnormal pattern is present in the thickness values based on a comparison of the thickness values to a reference data set;
  upon detecting the abnormal pattern in the thickness values, predicting early diabetic retinopathy in the subject based on a weighted predictor function calculated by a processor as:

$$PEDR(M_D, M_C) = \min \sum_{i=1}^{N} w_i \times d(M_{Di}, M_{Ci})$$

wherein $w_i$ is a weight coefficient ($w_i \geq 0$, $i=1 \ldots N$), d is a distance function; $M_{Di}$, $M_{Ci}$ are measured values of criteria comprising thickness, reflectance, scattering coefficient, and texture measures for the retina of the subject and normal healthy subjects, respectively; N is the number of criteria considered in the analysis (N=4); and PEDR is a natural distance measure for similarity search where $w_i$ is the extent to which $M_{Di}$ is matched to $M_{Ci}$.

2. The method of claim 1, wherein the obtaining comprises computing at least one quantitative measure (QM) within a region of interest (ROI), wherein the reference data set comprises reference values for the at least one QM, and wherein the criteria further comprises values for the at least one QM.

3. The method of claim 2, wherein a first of the at least one QM is a normalized standard deviation in the ROI defined as a first quantitative measure (QM1):

$$QM = \frac{\sqrt{\frac{1}{N-1} \times \sum_{ROI_{high}} \sum_{ROI_{width}} (I(x,y) - \bar{I})^2}}{(I_{max} - I_{min})}$$

where (x, y) are location coordinates in the ROI, N is the number of pixels in the ROI, I(x,y) is the OCT signal as a function of location within the ROI, and $\bar{I}$ is the average OCT signal within the ROI.

4. The method of claim 2, wherein a second of the at least one QM comprises an integrated backscattered index as a second QM (QM2) defined as:

$$QM2 = \frac{1}{(x_r - x_l)} \frac{1}{(y_n - y_m)} \sum_{j=r}^{l} \sum_{i=n}^{m} |I(x_j, y_i)|$$

where (x, y) are location coordinates in the ROI, I(x,y) is the OCT signal as a function of location within the ROI, an ROI corresponds to an (n-m) segment in depth and an (r-l) segment in lateral displacement.

5. The method of claim 2, wherein an early diabetic retinopathy (EDR) index defined as a third QM (QM3):

$$QM3 = \frac{NMR}{NRS}$$

where NMR is the normalized mean reflectance and NRS is the normalized reflectance of saturation.

* * * * *